(12) United States Patent
Miller et al.

(10) Patent No.: US 11,014,891 B2
(45) Date of Patent: May 25, 2021

(54) REDUCTION-TRIGGERED ANTIBACTERIAL SIDEROMYCINS

(71) Applicant: UNIVERSITY OF NOTRE DAME DU LAC, Notre Dame, IN (US)

(72) Inventors: Marvin J. Miller, South Bend, IN (US); Cheng Ji, Buffalo Grove, IL (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 0 days.

(21) Appl. No.: 15/031,736

(22) PCT Filed: Oct. 23, 2014

(86) PCT No.: PCT/US2014/062069
§ 371 (c)(1),
(2) Date: Apr. 23, 2016

(87) PCT Pub. No.: WO2015/061630
PCT Pub. Date: Apr. 30, 2015

(65) Prior Publication Data
US 2016/0368878 A1 Dec. 22, 2016

Related U.S. Application Data

(60) Provisional application No. 61/894,770, filed on Oct. 23, 2013.

(51) Int. Cl.
| | | |
|---|---|---|
| *C07D 215/56* | (2006.01) |
| *C07D 209/14* | (2006.01) |
| *C07D 261/14* | (2006.01) |
| *C07D 501/00* | (2006.01) |
| *C07D 215/22* | (2006.01) |
| *C07D 413/12* | (2006.01) |
| *C07D 207/40* | (2006.01) |
| *C07D 413/14* | (2006.01) |
| *C07D 401/12* | (2006.01) |
| *C07D 263/34* | (2006.01) |
| *C07D 265/26* | (2006.01) |
| *A61K 47/54* | (2017.01) |

(52) U.S. Cl.
CPC .......... *C07D 215/56* (2013.01); *A61K 47/54* (2017.08); *A61K 47/559* (2017.08); *C07D 207/40* (2013.01); *C07D 209/14* (2013.01); *C07D 215/22* (2013.01); *C07D 261/14* (2013.01); *C07D 263/34* (2013.01); *C07D 265/26* (2013.01); *C07D 401/12* (2013.01); *C07D 413/12* (2013.01); *C07D 413/14* (2013.01); *C07D 501/00* (2013.01)

(58) Field of Classification Search
None
See application file for complete search history.

(56) References Cited

FOREIGN PATENT DOCUMENTS

WO WO2012167368 12/2012

OTHER PUBLICATIONS

Apr. 2013, Springer, Elizabeth, The Development and Syntheses of Nitroreductase Triggered Releasable Linkers for use in Siderophore Drug Conjugates, a Master of Science Dissertation, University Notre Dame, Apr. 2013.
May 1, 2015, International Search Report issued for PCT/US2014/062069.
May 1, 2015, Written Opinion issued for PCT/US2014/062069.
Apr. 26, 2016, International Preliminary Report on Patentability issued for PCT/US2014/062069.

*Primary Examiner* — Samantha L Shterengarts
(74) *Attorney, Agent, or Firm* — Law Office of John K. Pike, PLLC

(57) ABSTRACT

A compound is provided, comprising: an Fe(III)-binding or an Fe(III)-bound siderophore; one or more optional linker covalently bound to the siderophore; a drug; and an Fe(III) to Fe(II) reduction triggered linker bound to the drug and the linker or, if no linker is present, then bound to the drug and the siderophore. Compositions and methods including the compound are also provided.

17 Claims, 195 Drawing Sheets

Figure 8
Figure 8A
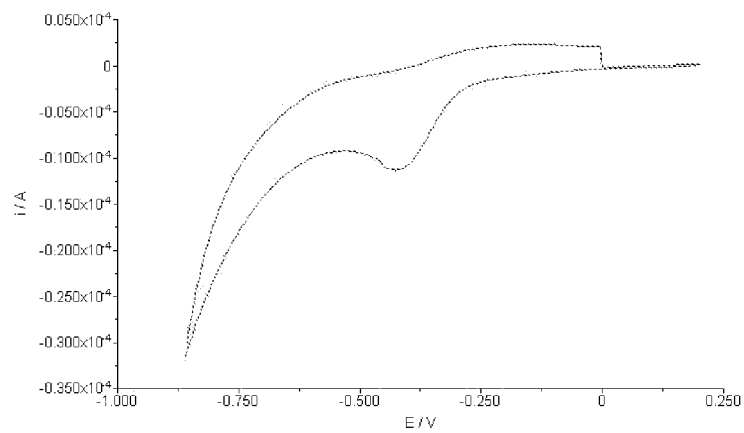
Figure 8B
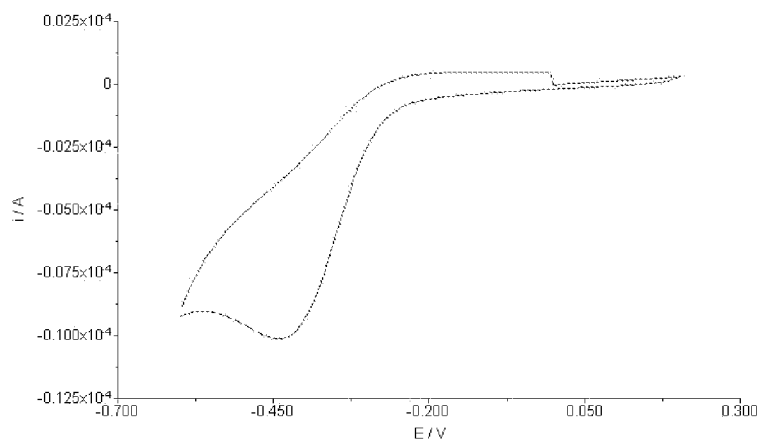

Comp 1

Comp 2
(R = H)

FIG. 12A

Table of examples of siderophores

FIG. 12B

| Compound ID / Batch ID / Source Lot No | Structure | Quantity (mg) | FW | Physical Form | Color | Salt Form | Source | Comments | Registration Date |
|---|---|---|---|---|---|---|---|---|---|
| ND-008785 / ND-008785.0002 / 9724034 | | 13000 | 734.58 | Solid | White | | HKI | 1997 Box-2 | 1/11/2009 |
| ND-009003 / ND-009003.0001 / 9824031 | | 4000 | 913.74 | Solid | White | | HKI | 1997 Box-2 | 1/11/2009 |
| ND-008721 / ND-008721.0001 / 95438 | | 2000 | 626.59 | Solid | White | | HKI | Yellow-1994-2000 | 1/11/2009 |

| ND-009003 | ND-009064 | ND-008894 | ND-009185 |
|---|---|---|---|
| ND-009003.0003 | ND-009064.0001 | ND-008894.0002 | ND-009185.0001 |
| 9824031 | 9824162 | 9824004 | 9824116 |
|  |  |  |  |
| 1500 | 2000 | 2000 | 2000 |
| 913.74 | 903.91 | 936.34 | 710.69 |
| Solid | Solid | Solid | Solid |
| Yellow | White | White | White |
| HKI | HKI | HKI | HKI |
| 1998 Box-1 | 1998 Box-3 | 1998 Box-1 | Yellow-1994-2000 |
| 1/11/2009 | 1/11/2009 | 1/11/2009 | 1/11/2009 |

| ND-008896 | ND-008756 | ND-008721 | ND-009016 |
|---|---|---|---|
| ND-008896.0002 | ND-008756.0001 | ND-008721.0002 | ND-009016.0001 |
| 9824006 | 9724007 | 9543B | 9624116 |
|  |  |  |  |
| 1000 | 1000 | 1000 | 1500 |
| 915.92 | 283.24 | 626.59 | 248.23 |
| Solid | Solid | Solid | Solid |
| White | White | Yellow | White |
| HK1 | HK1 | HK1 | HK1 |
| 1998 Box-1 | 1997 Box-1 | 1996 Box | 1998 Box-3 |
| 1/11/2009 | 1/11/2009 | 1/11/2009 | 1/11/2009 |

FIG. 12E

| ND-009176 | ND-009176.0002 | 9924116 | [structure] | 1000 | 917.93 | Solid | White | HK1 | 1999 Box-1 | 1/11/2009 |
|---|---|---|---|---|---|---|---|---|---|---|
| ND-009178 | ND-009178.0002 | 9924118 | [structure] | 1000 | 148.11 | Solid | White | HK1 | 1999 Box-1 | 1/11/2009 |
| ND-009189 | ND-009189.0001 | 9924130 | [structure] | 1000 | 933.93 | Solid | White | HK1 | 1999 Box-1 | 1/11/2009 |
| ND-008787 | ND-008787.0002 | 9524025 | [structure] | 700 | 357.31 | Solid | White | HK1 | Yellow-1994-2000 | 1/11/2009 |

FIG. 12F

| ND-008863 | ND-009099 | ND-009100 | ND-009101 |
|---|---|---|---|
| ND-008863.0001 | ND-009099.0002 | ND-009100.0002 | ND-009101.0002 |
| 9724108 | 9924035 | 9924036 | 9924037 |
| | | | |
| 600 | 600 | 600 | 600 |
| 901.89 | 1288.3 | 1304.3 | 1288.3 |
| Solid | Solid | Solid | Solid |
| White | White | White | White |
| HKI | HKI | HKI | HKI |
| 1997 Box-2 | 1999 Box-2 | 1999 Box-2 | 1999 Box-2 |
| 1/11/2009 | 1/11/2009 | 1/11/2009 | 1/11/2009 |

| ND-008758 | ND-008681 | ND-008847 | ND-008780 |
|---|---|---|---|
| ND-008758.0001 | ND-008681.0001 | ND-008847.0001 | ND-008780.0001 |
| 9724009 | 954324 | 9724094 | 9724029 |
|  |  |  |  |
| 500 | 500 | 500 | 500 |
| 299.24 | 640.66 | 666.98 | 309.23 |
| Solid | Solid | Solid | Solid |
| White | White | White | White |
| HK1 | HK1 | HK1 | HK1 |
| 1997 Box-1 | 1996 Box | Yellow-1994-2000 | Yellow-1994-2000 |
| 1/11/2009 | 1/11/2009 | 1/11/2009 | 1/11/2009 |

| ND-008791 | ND-008796 | ND-008806 | ND-008840 |
|---|---|---|---|
| ND-008791.0001 | ND-008796.0001 | ND-008806.0001 | ND-008840.0002 |
| 9724039 | 9724045 | 9724062 | 9724090 |
|  |  |  |  |
| 500 | 500 | 500 | 500 |
| 662.6 | 391.72 | 574.54 | 1288.1 |
| Solid | Solid | Solid | Solid |
| White | Tan | White | White |
| HK1 | HK1 | HK1 | HK1 |
| 1997 Box-1 | 1997 Box-1 | 1997 Box-1 | 1997 Box-2 |
| 1/11/2009 | 1/11/2009 | 1/11/2009 | 1/11/2009 |

| ND-008732 | ND-009236 | ND-008872 | ND-008859 |
|---|---|---|---|
| ND-008732.0001 | ND-009236.0001 | ND-008872.0001 | ND-008859.0001 |
| 9624046 | 10024035 | 9724116 | 9724107 |
|  |  |  |  |
| 500 | 500 | 500 | 500 |
| 284.27 | 662.64 | 743.07 | 738.05 |
| Solid | Solid | Solid | Solid |
| White | White | White | White |
| HK1 | HK1 | HK1 | HK1 |
| 1999 Box-1 | 1998 Box-3 | 1997 Box-2 | 1997 Box-2 |
| 1/11/2009 | 1/11/2009 | 1/11/2009 | 1/11/2009 |

| ND-009102 | ND-009091 | ND-009166 | ND-009163 |
|---|---|---|---|
| ND-009102.0001 | ND-009091.0002 | ND-009166.0002 | ND-009163.0002 |
| 9924038 | 9924025 | 9924106 | 9924103 |
|  |  |  |  |
| 500 | 500 | 500 | 500 |
| 618.5 | 934.89 | 256.75 | 228.7 |
| Solid | Solid | Solid | Solid |
| White | White | White | White |
| HKI | HKI | HKI | HKI |
| 1999 Box-2 | 1999 Box-2 | 1999 Box-1 | 1999 Box-1 |
| 1/11/2009 | 1/11/2009 | 1/11/2009 | 1/11/2009 |

FIG. 12L

| ND-008696 | ND-008696.0001 | 9524021 | [structure] | 400 | 309.27 | Solid | White | HK1 | Yellow-1994-2000 | 1/11/2009 |
| ND-009251 | ND-009251.0001 | 10024049 | [structure] | 400 | 692.67 | Solid | White | HK1 | Yellow-1994-2000 | 1/11/2009 |
| ND-008757 | ND-008757.0001 | 9724008 | [structure] | 400 | 221.17 | Solid | White | HK1 | 1997 Box-1 | 1/11/2009 |
| ND-008768 | ND-008768.0001 | 9724019 | [structure] | 400 | 403.34 | Solid | White | HK1 | 1997 Box-1 | 1/11/2009 |

| ND-008770 | ND-008770.0001 | 9724021 |  | 400 | 862.6 | Solid | White | HKI | 1997 Box-1 | 1/11/2009 |
|---|---|---|---|---|---|---|---|---|---|---|
| ND-008773 | ND-008773.0001 | 9724024 |  | 400 | 444.35 | Solid | Tan | HKI | 1997 Box-1 | 1/11/2009 |
| ND-008788 | ND-008788.0001 | 9724036 |  | 400 | 939.83 | Solid | White | HKI | 1997 Box-1 | 1/11/2009 |
| ND-008802 | ND-008802.0001 | 9724058 |  | 400 | 357.27 | Solid | White | HKI | 1997 Box-1 | 1/11/2009 |

| ND-008847 | ND-008847.0004 | 9724094 |  | 400 | 666.98 | Solid | White | HKI | 1997 Box-2 | 1/11/2009 |
|---|---|---|---|---|---|---|---|---|---|---|
| ND-008848 | ND-008848.0002 | 9724095 |  | 400 | 703.61 | Solid | White | HKI | 1997 Box-2 | 1/11/2009 |
| ND-008893 | ND-008893.0002 | 9824003 |  | 400 | 659.06 | Solid | White | HKI | 1998 Box-1 | 1/11/2009 |
| ND-008936 | ND-008936.0001 | 9824037 |  | 400 | 727.69 | Solid | White | HKI | 1998 Box-1 | 1/11/2009 |

FIG. 12O

| ND-008729 | ND-008715 | ND-009262 | ND-008965 |
|---|---|---|---|
| ND-008729.0001 | ND-008715.0001 | ND-009262.0001 | ND-008965.0002 |
| 9624024 | 9624011 | 10024061 | 9624066 |
| (structure) | (structure) | (structure) | (structure) |
| 400 | 400 | 400 | 400 |
| 710.69 | 366.28 | 890.91 | 716.67 |
| Solid | Solid | Solid | Solid |
| White | White | White | White |
| HK1 | HK1 | HK1 | HK1 |
| 1989 Box-1 | 1999 Box-1 | 1998 Box-3 | 1998 Box-1 |
| 1/11/2009 | 1/11/2009 | 1/11/2009 | 1/11/2009 |

| ND-008749 | ND-008749.0001 | 9624055 |  | 400 | 862.6 | Solid | White | HK1 | 1999 Box-1 | 1/11/2009 |
|---|---|---|---|---|---|---|---|---|---|---|
| ND-009170 | ND-009170.0002 | 9924110 |  | 400 | 917.93 | Solid | White | HK1 | 1999 Box-1 | 1/11/2009 |
| ND-009171 | ND-009171.0002 | 9924111 |  | 400 | 1248.3 | Solid | White | HK1 | 1999 Box-1 | 1/11/2009 |
| ND-009177 | ND-009177.0002 | 9924117 |  | 400 | 1234.3 | Solid | White | HK1 | 1999 Box-1 | 1/11/2009 |

FIG. 12Q

| ND-009079 | ND-009090 | ND-009098 | ND-009124 |
|---|---|---|---|
| ND-009079.0002 | ND-009090.0002 | ND-009098.0002 | ND-009124.0002 |
| 9924013 | 9924024 | 9924033 | 9924059 |
| (structure) | (structure) | (structure) | (structure) |
| 400 | 400 | 400 | 400 |
| 758.73 | 676.67 | 934.89 | 880.76 |
| Solid | Solid | Solid | Solid |
| White | White | Tan | White |
| HK1 | HK1 | HK1 | HK1 |
| 1999 Box-2 | 1999 Box-2 | 1999 Box-2 | 1999 Box-2 |
| 1/11/2009 | 1/11/2009 | 1/11/2009 | 1/11/2009 |

| ND-008963 | ND-009080 | ND-009105 | ND-008769 |
|---|---|---|---|
| ND-008963.0001 | ND-009080.0001 | ND-009105.0001 | ND-008769.0001 |
| 9924064 | 9924014 | 9924034 | 9724020 |
|  |  |  |  |
| 350 | 300 | 300 | 300 |
| 739.11 | 749.72 | 298.64 | 756.71 |
| Solid | Solid | Solid | Solid |
| White | White | White | White |
| HKI | HKI | HKI | HKI |
| 1998 Box-1 | Yellow-1994-2000 | Yellow-1994-2000 | 1997 Box-1 |
| 1/11/2009 | 1/11/2009 | 1/11/2009 | 1/11/2009 |

FIG. 12S

| ND-008795 | ND-008795.0002 | 9724044 | [structure] | 300 | 373.27 | Solid | White | HKI | 1997 Box-1 | 1/11/2009 |
| --- | --- | --- | --- | --- | --- | --- | --- | --- | --- | --- |
| ND-008795 | ND-008795.0003 | 9724044 | [structure] | 300 | 373.27 | Solid | White | HKI | 1997 Box-1 | 1/11/2009 |
| ND-008800 | ND-008800.0001 | 9724049 | [structure] | 300 | 470.43 | Solid | White | HKI | 1997 Box-1 | 1/11/2009 |
| ND-008807 | ND-008807.0001 | 9724063 | [structure] | 300 | 449.36 | Solid | White | HKI | 1997 Box-1 | 1/11/2009 |

| ND-008835 | ND-008814 | ND-008849 | ND-008809 |
|---|---|---|---|
| ND-008835.0001 | ND-008814.0001 | ND-008849.0001 | ND-008809.0001 |
| 9724082 | 9724070 | 9724096 | 9724065 |
|  |  |  |  |
| 300 | 300 | 300 | 300 |
| 457.39 | 357.27 | 724.03 | 745.09 |
| Solid | Solid | Solid | Solid |
| White | White | White | White |
| HKI | HKI | HKI | HKI |
| 1997 Box-2 | 1997 Box-2 | 1997 Box-1 | 1997 Box-1 |
| 1/11/2009 | 1/11/2009 | 1/11/2009 | 1/11/2009 |

FIG. 12U

| ND-008851 | ND-008870 | ND-008869 | ND-008873 |
|---|---|---|---|
| ND-008851.0002 | ND-008870.0001 | ND-008869.0001 | ND-008873.0001 |
| 9724088 | 9724114 | 9724113 | 9724117 |
| (structure) | (structure) | (structure) | (structure) |
| 300 | 300 | 300 | 300 |
| 754.7 | 1085.9 | 699.02 | 763.49 |
| Solid | Solid | Solid | Solid |
| White | White | White | White |
| HKI | HKI | HKI | HKI |
| 1997 Box-2 | 1997 Box-2 | 1997 Box-2 | 1997 Box-2 |
| 1/11/2009 | 1/11/2009 | 1/11/2009 | 1/11/2009 |

| ND-008876 | ND-008929 | ND-008935 | ND-008941 |
|---|---|---|---|
| ND-008876.0001 | ND-008929.0002 | ND-008935.0001 | ND-008941.0001 |
| 9724120 | 9824030 | 9824036 | 9824042 |
|  |  |  |  |
| 300 | 300 | 300 | 300 |
| 745.04 | 623.69 | 1039.9 | 737.53 |
| Solid | Solid | Solid | Solid |
| White | White | White | White |
| HKI | HKI | HKI | HKI |
| 1997 Box-2 | 1998 Box-1 | 1998 Box-1 | 1998 Box-1 |
| 1/11/2009 | 1/11/2009 | 1/11/2009 | 1/11/2009 |

FIG. 12W

| ND-008942 | ND-008942.0002 | 9024043 | [structure] | 300 | 539.53 | Solid | White | HKI | 1998 Box-1 | 1/11/2009 |
|---|---|---|---|---|---|---|---|---|---|---|
| ND-009029 | ND-009029.0001 | 9024129 | [structure] | 300 | 572.43 | Solid | White | HKI | 1998 Box-3 | 1/11/2009 |
| ND-009242 | ND-009242.0001 | 10024042 | [structure] | 300 | 265.35 | Oil | White | HKI | 1998 Box-3 | 1/11/2009 |
| ND-009243 | ND-009243.0001 | 10024043 | [structure] | 300 | 222.28 | Solid | Yellow | HKI | 1998 Box-3 | 1/11/2009 |

| ND-008730 | ND-008764 | ND-009076 | ND-008730 |
|---|---|---|---|
| ND-008767.0001 | ND-008764.0001 | ND-009076.0002 | ND-008730.0001 |
| 9724018 | 9724015 | 9924010 | 9624042 |
|  |  |  |  |
| 250 | 250 | 380 | 300 |
| 591.52 | 724.67 | 834.78 | 357.27 |
| Solid | Solid | Solid | Solid |
| White | Yellow | White | White |
| HKI | HKI | HKI | HKI |
| 1997 Box-1 | 1997 Box-1 | 1999 Box-2 | 1999 Box-1 |
| 1/11/2009 | 1/11/2009 | 1/11/2009 | 1/11/2009 |

| ND-008794 | ND-008794.0001 | 9724042 |  | 250 | 282.25 | Solid | White | HK1 | 1997 Box-1 | 1/11/2009 |
|---|---|---|---|---|---|---|---|---|---|---|
| ND-008851 | ND-008851.0001 | 9724098 |  | 250 | 754.7 | Solid | White | HK1 | 1997 Box-1 | 1/11/2009 |
| ND-008856 | ND-008856.0001 | 9724103 |  | 250 | 660.63 | Solid | White | HK1 | 1997 Box-2 | 1/11/2009 |
| ND-008865 | ND-008865.0001 | 9724110 |  | 250 | 922.31 | Solid | White | HK1 | 1997 Box-2 | 1/11/2009 |

| ND-008787 | ND-008728 | ND-009272 | ND-008918 |
|---|---|---|---|
| ND-008787.0001 | ND-008728.0001 | ND-009272.0001 | ND-008918.0002 |
| 9524025 | 9624022 | 10024008 | 9624019 |
|  |  |  |  |
| 200 | 250 | 250 | 250 |
| 357.31 | 662.64 | 646.55 | 436.17 |
| Solid | Solid | Solid | Solid |
| White | White | White | White |
| HK1 | HK1 | HK1 | HK1 |
| Yellow-1994-2000 | 1999 Box-1 | 1998 Box-3 | 1998 Box-1 |
| 1/11/2009 | 1/11/2009 | 1/11/2009 | 1/11/2009 |

FIG. 12AA

| ND-008737 | ND-008795 | ND-008979 | ND-008986 |
|---|---|---|---|
| ND-008737.0001 | ND-008795.0001 | ND-008979.0001 | ND-008986.0001 |
| 9624034 | 9724044 | 9824060 | 9824087 |
| (structure) | (structure) | (structure) | (structure) |
| 200 | 200 | 200 | 200 |
| 208.17 | 373.27 | 791.75 | 864.8 |
| Solid | Solid | Solid | Solid |
| White | White | White | Yellow |
| HKI | HKI | HKI | HKI |
| Yellow-1994-2000 | Yellow-1994-2000 | Yellow-1994-2000 | Yellow-1994-2000 |
| 1/11/2009 | 1/11/2009 | 1/11/2009 | 1/11/2009 |

| ND-008995 | ND-008995.0001 | 9824099 |  | 200 | 188.57 | Solid | White | HKI | Yellow-1994-2000 | 1/11/2009 |
|---|---|---|---|---|---|---|---|---|---|---|
| ND-009093 | ND-009093.0001 | 9924027 |  | 200 | 273.24 | Solid | White | HKI | Yellow-1994-2000 | 1/11/2009 |
| ND-009270 | ND-009270.0001 | 10024067 |  | 200 | 889.88 | Solid | White | HKI | Yellow-1994-2000 | 1/11/2009 |
| ND-009221 | ND-009221.0002 | 9924153 |  | 200 | 939.92 | Solid | White | HKI | 1986 Box | 1/11/2009 |

FIG. 12AC

| | | | | | | |
|---|---|---|---|---|---|---|
| ND-008759 | ND-008759.0001 | 9724010 | | 200 371.3 Solid White | HKI 1997 Box-1 1/11/2009 | |
| ND-008760 | ND-008760.0001 | 9724011 | | 200 724.67 Solid White | HKI 1997 Box-1 1/11/2009 | |
| ND-008761 | ND-008761.0001 | 9724012 | | 200 710.64 Solid White | HKI 1997 Box-1 1/11/2009 | |
| ND-008762 | ND-008762.0001 | 9724013 | | 200 529.45 Solid White | HKI 1997 Box-1 1/11/2009 | |

FIG. 12AD

| ND-008765 | | |
|---|---|---|
| ND-008765.0001 | | |
| 9724016 | | |
| 200 | | |
| 591.52 | | |
| Solid | | |
| White | | |
| HKI | | |
| 1997 Box-1 | | |
| 1/11/2009 | | |

| ND-008778 |
|---|
| ND-008778.0001 |
| 9724027 |
| 200 |
| 403.34 |
| Solid |
| White |
| HKI |
| 1997 Box-1 |
| 1/11/2009 |

| ND-008790 |
|---|
| ND-008790.0001 |
| 9724038 |
| 200 |
| 945.79 |
| Solid |
| White |
| HKI |
| 1997 Box-1 |
| 1/11/2009 |

| ND-008799 |
|---|
| ND-008799.0001 |
| 9724048 |
| 200 |
| 502.43 |
| Solid |
| Brown |
| HKI |
| 1997 Box-1 |
| 1/11/2009 |

| ND-008836 | ND-008838 | ND-008846 | ND-008852 |
|---|---|---|---|
| ND-008836.0001 | ND-008838.0001 | ND-008846.0002 | ND-008852.0002 |
| 9724086 | 9724088 | 9724093 | 9724099 |
|  |  |  |  |
| 200 | 200 | 200 | 200 |
| 810.76 | 653.64 | 646.56 | 775.11 |
| Solid | Solid | Solid | Solid |
| White | Yellow | White | White |
| HKI | HKI | HKI | HKI |
| 1997 Box-2 | 1997 Box-2 | 1997 Box-2 | 1997 Box-2 |
| 1/11/2009 | 1/11/2009 | 1/11/2009 | 1/11/2009 |

FIG. 12AF

| ND-008928 | ND-008923 | ND-008912 | ND-008892 |
|---|---|---|---|
| ND-008928.0001 | ND-008923.0002 | ND-008912.0001 | ND-008892.0001 |
| 9824029 | 9824024 | 9824013 | 9824002 |
| | | | |
| 200 | 200 | 200 | 200 |
| 807.94 | 774.75 | 907.83 | 1305.7 |
| Solid | Solid | Solid | Solid |
| White | White | White | White |
| HKI | HKI | HKI | HKI |
| 1998 Box-1 | 1998 Box-1 | 1998 Box-1 | 1998 Box-1 |
| 1/11/2009 | 1/11/2009 | 1/11/2009 | 1/11/2009 |

FIG. 12AG

| ND-008952 | ND-008945 | ND-008944 | ND-008939 |
|---|---|---|---|
| ND-008952.0002 | ND-008945.0001 | ND-008944.0001 | ND-008939.0001 |
| 9824053 | 9824046 | 9824045 | 9824040 |
| | | | |
| 200 | 200 | 200 | 200 |
| 713.67 | 747.77 | 767.56 | 883.67 |
| Solid | Solid | Solid | Solid |
| White | White | White | White |
| HKI | HKI | HKI | HKI |
| 1998 Box-1 | 1998 Box-1 | 1998 Box-1 | 1998 Box-1 |
| 1/11/2009 | 1/11/2009 | 1/11/2009 | 1/11/2009 |

| ND-008954 | ND-009042 | ND-009063 | ND-009065 |
|---|---|---|---|
| ND-008954.0002 | ND-009042.0001 | ND-009063.0001 | ND-009065.0001 |
| 9824055 | 9824142 | 9824161 | 9824163 |
|  |  |  |  |
| 200 | 200 | 200 | 200 |
| 674.63 | 572.43 | 1081.1 | 1061.7 |
| Solid | Solid | Solid | Solid |
| White | White | White | White |
| HKI | HKI | HKI | HKI |
| 1998 Box-1 | 1998 Box-3 | 1998 Box-3 | 1998 Box-3 |
| 1/11/2009 | 1/11/2009 | 1/11/2009 | 1/11/2009 |

| ND-008727 | ND-009259 | ND-009239 | ND-009249 |
|---|---|---|---|
| ND-008727.0001 | ND-009259.0001 | ND-009239.0002 | ND-009249.0001 |
| 9624020 | 10024058 | 10024038 | 10024006 |
|  |  |  |  |
| 200 | 200 | 200 | 200 |
| 586.46 | 722.69 | 662.64 | 940.9 |
| Solid | Solid | Solid | Solid |
| White | White | White | White |
| HKI | HKI | HKI | HKI |
| 1999 Box-1 | 1998 Box-3 | 1998 Box-3 | 1998 Box-3 |
| 1/11/2009 | 1/11/2009 | 1/11/2009 | 1/11/2009 |

FIG. 12AJ

| ND-008736 | ND-008736.0001 | 9624033 | [structure] | 200 | 344.32 | Solid | White | HK1 | 1999 Box-1 | 1/11/2009 |
|---|---|---|---|---|---|---|---|---|---|---|
| ND-008738 | ND-008738.0001 | 9624035 | [structure] | 200 | 284.27 | Solid | White | HK1 | 1999 Box-1 | 1/11/2009 |
| ND-008735 | ND-008735.0001 | 9624049 | [structure] | 200 | 300.27 | Solid | White | HK1 | 1999 Box-1 | 1/11/2009 |
| ND-009127 | ND-009127.0002 | 9624062 | [structure] | 200 | 309.27 | Solid | White | HK1 | 1999 Box-1 | 1/11/2009 |

| ND-009128 | ND-009128.0002 | 9924063 |  | 200 | 1293.4 | Solid | White | HKI | 1999 Box-1 | 1/11/2009 |
| --- | --- | --- | --- | --- | --- | --- | --- | --- | --- | --- |
| ND-009140 | ND-009140.0002 | 9924082 |  | 200 | 1189.1 | Solid | White | HKI | 1999 Box-1 | 1/11/2009 |
| ND-009145 | ND-009145.0002 | 9924087 |  | 200 | 333.38 | Solid | White | HKI | 1999 Box-1 | 1/11/2009 |
| ND-009152 | ND-009152.0002 | 9924092 |  | 200 | 1016.1 | Solid | White | HKI | 1999 Box-1 | 1/11/2009 |

| ND-009071 | ND-009069 | ND-009068 | ND-009168 |
|---|---|---|---|
| ND-009071.0002 | ND-009069.0002 | ND-009068.0001 | ND-009168.0002 |
| 9924005 | 9924003 | 9924002 | 9924108 |
|  |  |  |  |
| 200 | 200 | 200 | 200 |
| 758.73 | 1090.1 | 903.82 | 1072.8 |
| Solid | Solid | Solid | Solid |
| White | White | White | White |
| HKI | HKI | HKI | HKI |
| 1999 Box-2 | 1999 Box-2 | 1999 Box-2 | 1999 Box-1 |
| 1/11/2009 | 1/11/2009 | 1/11/2009 | 1/11/2009 |

| ND-009115 | | | | | | | |
|---|---|---|---|---|---|---|---|
| ND-009115.0002 |  | 200 | 424.36 | Solid | Brown | HKI | 1999 Box-2 |
| 9924050 | | | | | | | 1/11/2009 |
| ND-009121 | | | | | | | |
| ND-009121.0002 |  | 200 | 767.8 | Solid | Tan | HKI | 1999 Box-2 |
| 9924056 | | | | | | | 1/11/2009 |
| ND-009004 | | | | | | | |
| ND-009004.0001 |  | 150 | 317.09 | Solid | White | HKI | Yellow-1994-2000 |
| 9824103 | | | | | | | 1/11/2009 |
| ND-008766 | | | | | | | |
| ND-008766.0001 |  | 150 | 724.67 | Solid | White | HKI | 1997 Box-1 |
| 9724017 | | | | | | | 1/11/2009 |

FIG. 12AN

| ND-008813 | ND-008812 | ND-008848 | ND-008842 |
|---|---|---|---|
| ND-008813.0001 | ND-008812.0001 | ND-008848.0001 | ND-008842.0001 |
| 9724069 | 9724068 | 9724095 | 9724092 |
| | | | |
| 150 | 150 | 150 | 150 |
| 770.69 | 710.64 | 703.61 | 991.99 |
| Solid | Solid | Solid | Solid |
| White | White | White | White |
| HKI | HKI | HKI | HKI |
| 1997 Box-2 | 1997 Box-2 | 1997 Box-1 | 1997 Box-1 |
| 1/11/2009 | 1/11/2009 | 1/11/2009 | 1/11/2009 |

| | | | | | | | |
|---|---|---|---|---|---|---|---|
| ND-008837 | ND-008837.0001 | 9724087 |  | 150 | 710.64 | Solid | White | HK1 | 1997 Box-2 | 1/11/2009 |
| ND-008839 | ND-008839.0002 | 9724089 |  | 150 | 678.6 | Solid | White | HK1 | 1997 Box-2 | 1/11/2009 |
| ND-008875 | ND-008875.0001 | 9724119 |  | 150 | 964.19 | Solid | White | HK1 | 1997 Box-2 | 1/11/2009 |
| ND-008890 | ND-008890.0001 | 9724132 |  | 150 | 604.54 | Solid | White | HK1 | 1997 Box-2 | 1/11/2009 |

FIG. 12AP

| ND-008933 | ND-008946 | ND-008947 | ND-008951 |
|---|---|---|---|
| ND-008933.0001 | ND-008946.0001 | ND-008947.0002 | ND-008951.0002 |
| 9824034 | 9824047 | 9824048 | 9824052 |
| | | | |
| 150 | 150 | 150 | 150 |
| 804.82 | 933.93 | 850.84 | 919.91 |
| Solid | Solid | Solid | Solid |
| White | White | White | White |
| HK1 | HK1 | HK1 | HK1 |
| 1998 Box-1 | 1998 Box-1 | 1998 Box-1 | 1998 Box-1 |
| 1/11/2009 | 1/11/2009 | 1/11/2009 | 1/11/2009 |

FIG. 12AQ

| ND-008967 | ND-008964 | ND-008962 | ND-008959 |
|---|---|---|---|
| ND-008967.0002 | ND-008964.0002 | ND-008962.0002 | ND-008959.0002 |
| 9824068 | 9824065 | 9824063 | 9824060 |
| | | | |
| 150 | 150 | 150 | 150 |
| 853.64 | 1347.7 | 1329.3 | 1381.5 |
| Solid | Solid | Solid | Solid |
| White | White | White | White |
| HKI | HKI | HKI | HKI |
| 1998 Box-1 | 1998 Box-1 | 1998 Box-1 | 1998 Box-1 |
| 1/11/2009 | 1/11/2009 | 1/11/2009 | 1/11/2009 |

| ND-008974 | ND-008973 | ND-008972 | ND-008967 |
|---|---|---|---|
| ND-008974.0002 | ND-008973.0002 | ND-008972.0002 | ND-008967.0003 |
| 9824075 | 9824074 | 9824073 | 9824068 |
|  |  |  |  |
| 150 | 150 | 150 | 150 |
| 804.78 | 1345.3 | 788.78 | 853.64 |
| Solid | Solid | Solid | Solid |
| White | White | White | White |
| HKI | HKI | HKI | HKI |
| 1998 Box-1 | 1998 Box-1 | 1998 Box-1 | 1998 Box-1 |
| 1/11/2009 | 1/11/2009 | 1/11/2009 | 1/11/2009 |

FIG. 12AS

| ND-008976 | ND-009041 | ND-009129 | ND-009222 |
|---|---|---|---|
| ND-008976.0002 | ND-009041.0001 | ND-009129.0002 | ND-009222.0001 |
| 9824077 | 9824141 | 9824064 | 9824155 |
| (structure) | (structure) | (structure) | (structure) |
| 150 | 150 | 150 | 149 |
| 904.89 | 758.73 | 719.43 | 955.91 |
| Solid | Solid | Solid | Solid |
| White | White | White | White |
| HKI | HKI | HKI | HKI |
| 1998 Box-1 | 1998 Box-3 | 1999 Box-1 | 1996 Box |
| 1/11/2009 | 1/11/2009 | 1/11/2009 | 1/11/2009 |

FIG. 12AT

| ND-009047 | ND-009228 | ND-008985 | ND-009221 |
|---|---|---|---|
| ND-009047.0001 | ND-009228.0002 | ND-008985.0002 | ND-009221.0001 |
| 9524026 | 10024027 | 9524086 | 9924154 |
| (structure) | (structure) | (structure) | (structure) |
| 100 | 130 | 140 | 148 |
| 357.31 | 1189.1 | 658.63 | 939.92 |
| Solid | Solid | Solid | Solid |
| White | White | White | White |
| HKI | HKI | HKI | HKI |
| Yellow-1994-2000 | 1998 Box-3 | 1998 Box-1 | 1996 Box |
| 1/11/2009 | 1/11/2009 | 1/11/2009 | 1/11/2009 |

FIG. 12AU

| ND-008702 | ND-008931 | ND-008983 | ND-009161 |
|---|---|---|---|
| ND-008702.0001 | ND-008931.0001 | ND-008983.0001 | ND-009161.0001 |
| 9824071 | 9824032 | 9824084 | 9824101 |
| [structure] | [structure] | [structure] | [structure] |
| 100 | 100 | 100 | 100 |
| 586.54 | 823.67 | 395.33 | 586.54 |
| Oil | Solid | Solid | Solid |
| White | White | White | White |
| HKI | HKI | HKI | HKI |
| Yellow-1994-2000 | Yellow-1994-2000 | Yellow-1994-2000 | Yellow-1994-2000 |
| 1/11/2009 | 1/11/2009 | 1/11/2009 | 1/11/2009 |

FIG. 12AV

| ND-008775 | ND-008763 | ND-009188 | ND-009229 |
|---|---|---|---|
| ND-008775.0001 | ND-008763.0001 | ND-009188.0001 | ND-009229.0001 |
| 9724025 | 9724014 | 9924129 | 10024028 |
| *(chemical structure)* | *(chemical structure)* | *(chemical structure)* | *(chemical structure)* |
| 100 | 100 | 100 | 100 |
| 356.29 | 371.3 | 1202.2 | 890.91 |
| Solid | Solid | Solid | Solid |
| White | White | White | White |
| HKI | HKI | HKI | HKI |
| 1997 Box-1 | 1997 Box-1 | 1996 Box | Yellow-1994-2000 |
| 1/11/2009 | 1/11/2009 | 1/11/2009 | 1/11/2009 |

FIG. 12AW

| ND-008782 | ND-008782.0001 | 9724031 | [structure] | 100 | 592.42 | Solid | Tan | HKI | 1997 Box-1 | 1/11/2009 |
| ND-008783 | ND-008783.0001 | 9724032 | [structure] | 100 | 367.26 | Solid | White | HKI | 1997 Box-1 | 1/11/2009 |
| ND-008784 | ND-008784.0001 | 9724033 | [structure] | 100 | 706.52 | Solid | White | HKI | 1997 Box-1 | 1/11/2009 |
| ND-008803 | ND-008803.0001 | 9724059 | [structure] | 100 | 417.32 | Solid | Brown | HKI | 1997 Box-1 | 1/11/2009 |

FIG. 12AX

| ND-008805 | ND-008805.0001 | 9724061 | [structure: bromo-trihydroxy benzylidene hydrazide with hydroxyphenyl] | 100 | 351.15 | Solid | White | HK1 | 1997 Box-1 | 1/11/2009 |
|---|---|---|---|---|---|---|---|---|---|---|
| ND-008846 | ND-008846.0001 | 9724093 | [structure] | 100 | 646.56 | Solid | White | HK1 | 1997 Box-1 | 1/11/2009 |
| ND-008852 | ND-008852.0001 | 9724099 | [structure] | 100 | 775.11 | Solid | White | HK1 | 1997 Box-1 | 1/11/2009 |
| ND-008843 | ND-008843.0001 | 9724085 | [structure] | 100 | 933.95 | Solid | Yellow | HK1 | 1997 Box-2 | 1/11/2009 |

FIG. 12AY

| ND-008841 | ND-008853 | ND-008854 | ND-008885 |
|---|---|---|---|
| ND-008841.0001 | ND-008853.0002 | ND-008854.0002 | ND-008885.0001 |
| 9724091 | 9724100 | 9724101 | 9724129 |
| | | | |
| 100 | 100 | 100 | 100 |
| 1265.3 | 716.07 | 672.04 | 544.49 |
| Solid | Solid | Solid | Solid |
| White | White | Yellow | White |
| HKI | HKI | HKI | HKI |
| 1997 Box-2 | 1997 Box-2 | 1997 Box-2 | 1997 Box-2 |
| 1/11/2009 | 1/11/2009 | 1/11/2009 | 1/11/2009 |

| ND-008922 | ND-008910 | ND-008908 | ND-008895 |
|---|---|---|---|
| ND-008922.0002 | ND-008910.0002 | ND-008908.0001 | ND-008895.0002 |
| 9824023 | 9824011 | 9824009 | 9824005 |
|  |  |  |  |
| 100 | 100 | 100 | 100 |
| 816.79 | 1034 | 756.78 | 589.53 |
| Solid | Solid | Solid | Solid |
| Yellow | White | White | White |
| HKI | HKI | HKI | HKI |
| 1998 Box-1 | 1998 Box-1 | 1998 Box-1 | 1998 Box-1 |
| 1/11/2009 | 1/11/2009 | 1/11/2009 | 1/11/2009 |

FIG. 12AAA

| ND-008926 | ND-008927 | ND-008940 | ND-008955 |
|---|---|---|---|
| ND-008926.0001 | ND-008927.0001 | ND-008940.0001 | ND-008955.0002 |
| 9824027 | 9824028 | 9824041 | 9824056 |
| | | | |
| 100 | 100 | 100 | 100 |
| 839.22 | 596.52 | 707.11 | 755.93 |
| Solid | Solid | Solid | Solid |
| White | White | White | White |
| HKI | HKI | HKI | HKI |
| 1998 Box-1 | 1998 Box-1 | 1998 Box-1 | 1998 Box-1 |
| 1/11/2009 | 1/11/2009 | 1/11/2009 | 1/11/2009 |

FIG. 12AAB

| ND-008969 | ND-008970 | ND-008971 | ND-008975 |
|---|---|---|---|
| ND-008969.0002 | ND-008970.0002 | ND-008971.0002 | ND-008975.0002 |
| 9824070 | 9824071 | 9824072 | 9824076 |
| | | | |
| 100 | 100 | 100 | 100 |
| 1445.4 | 873.83 | 807.1B | 807.1B |
| Solid | Solid | Solid | Solid |
| White | White | White | White |
| HK1 | HK1 | HK1 | HK1 |
| 1998 Box-1 | 1998 Box-1 | 1998 Box-1 | 1998 Box-1 |
| 1/11/2009 | 1/11/2009 | 1/11/2009 | 1/11/2009 |

FIG. 12AAC

| ND-008977 | ND-008984 | ND-008987 | ND-009005 |
|---|---|---|---|
| ND-008977.0002 | ND-008984.0002 | ND-008987.0002 | ND-009005.0002 |
| 9824078 | 9824085 | 9824088 | 9824106 |
| (structure) | (structure) | (structure) | (structure) |
| 100 | 100 | 100 | 100 |
| 753.53 | 631.66 | 799.76 | 317.09 |
| Solid | Solid | Solid | Solid |
| White | White | White | Brown |
| HKI | HKI | HKI | HKI |
| 1998 Box-1 | 1998 Box-1 | 1998 Box-1 | 1998 Box-3 |
| 1/11/2009 | 1/11/2009 | 1/11/2009 | 1/11/2009 |

FIG. 12AAD

| ND-009006 | | | | |
|---|---|---|---|---|
| ND-009006.0303 | | | | |
| 9824108 | | | | |
| 100 | 572.52 | Solid | White | HKI | 1998 Box-3 | 1/11/2009 |

| ND-009028 | | | | |
|---|---|---|---|---|
| ND-009028.0001 | | | | |
| 9824128 | | | | |
| 100 | 366.37 | Solid | White | HKI | 1998 Box-3 | 1/11/2009 |

| ND-009035 | | | | |
|---|---|---|---|---|
| ND-009035.0901 | | | | |
| 9824135 | | | | |
| 100 | 271.35 | Solid | White | HKI | 1998 Box-3 | 1/11/2009 |

| ND-009036 | | | | |
|---|---|---|---|---|
| ND-009036.0001 | | | | |
| 9824136 | | | | |
| 100 | 749.72 | Solid | White | HKI | 1998 Box-3 | 1/11/2009 |

FIG. 12AAE

| ND-009056 | ND-009060 | ND-009229 | ND-009250 |
|---|---|---|---|
| ND-009056.0001 | ND-009060.0001 | ND-009229.0003 | ND-009250.0002 |
| 9824153 | 9824157 | 10024028 | 10024048 |
| (structure) | (structure) | (structure) | (structure) |
| 100 | 100 | 100 | 100 |
| 693.65 | 716.65 | 890.91 | 1520.5 |
| Solid | Solid | Solid | Solid |
| White | Brown | White | White |
| HKI | HKI | HKI | HKI |
| 1998 Box-3 | 1998 Box-3 | 1998 Box-3 | 1998 Box-3 |
| 1/11/2009 | 1/11/2009 | 1/11/2009 | 1/11/2009 |

FIG. 12AAF

| ND-008726 | ND-008720 | ND-008716 | ND-009265 |
|---|---|---|---|
| ND-008726.0001 | ND-008720.0001 | ND-008716.0001 | ND-009265.0002 |
| 9624021 | 9624015 | 9624010 | 10024064 |
| [structure] | [structure] | [structure] | [structure] |
| 100 | 100 | 100 | 100 |
| 664.57 | 642.59 | 408.36 | 1257.3 |
| Solid | Solid | Solid | Solid |
| White | White | White | White |
| HKI | HKI | HKI | HKI |
| 1999 Box-1 | 1999 Box-1 | 1999 Box-1 | 1998 Box-3 |
| 1/11/2009 | 1/11/2009 | 1/11/2009 | 1/11/2009 |

FIG. 12AAG
| ND-008739 | ND-008739.0001 | 9624036 | 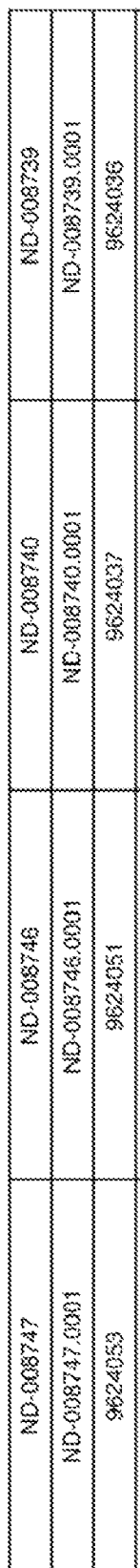 | 100 | 719.65 | Solid | White | HKI | 1999 Box-1 | 1/11/2009 |
| --- | --- | --- | --- | --- | --- | --- | --- | --- | --- | --- |
| ND-008740 | ND-008740.0001 | 9624037 | 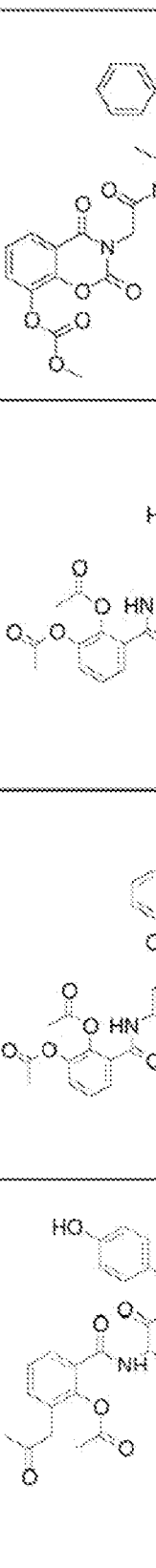 | 100 | 592.51 | Solid | White | HKI | 1999 Box-1 | 1/11/2009 |
| ND-008746 | ND-008746.0001 | 9624051 | 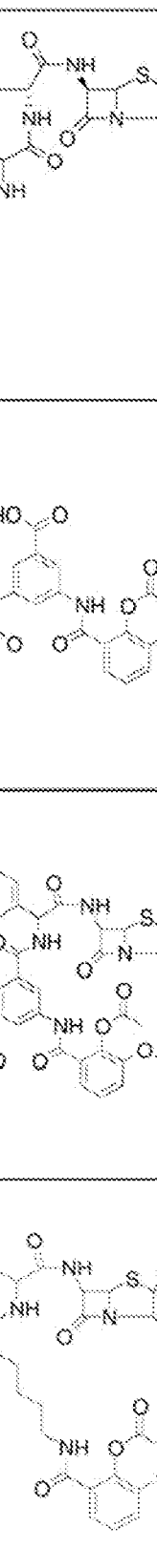 | 100 | 923.9 | Solid | White | HKI | 1999 Box-1 | 1/11/2009 |
| ND-008747 | ND-008747.0001 | 9624053 | 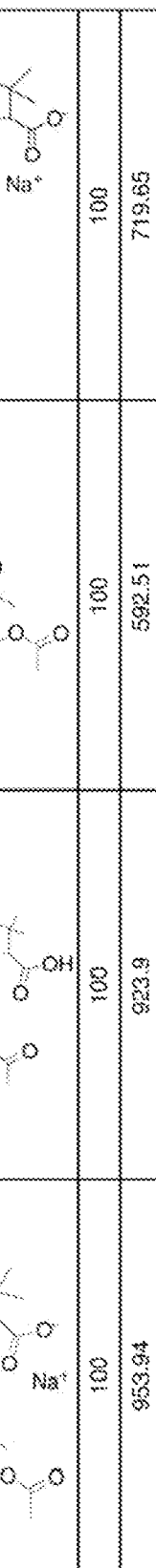 | 100 | 953.94 | Solid | White | HKI | 1999 Box-1 | 1/11/2009 |

FIG. 12AAH
| | | | | | | | |
|---|---|---|---|---|---|---|---|
| ND-009130 | ND-009130.0002 | 9924065 | 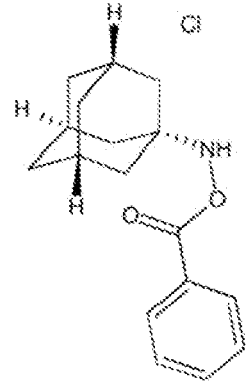 | 100 | 305.81 | Solid | White | HKI | 1999 Box-1 | 1/11/2009 |
| ND-009133 | ND-009133.0002 | 9924066 | 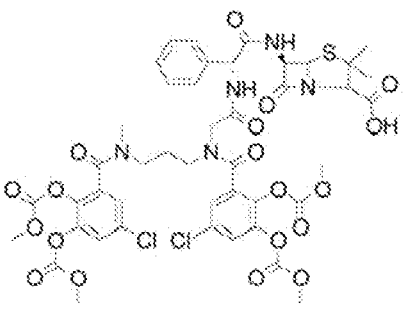 | 100 | 1050.8 | Solid | White | HKI | 1999 Box-1 | 1/11/2009 |
| ND-009136 | ND-009136.0002 | 9924069 | 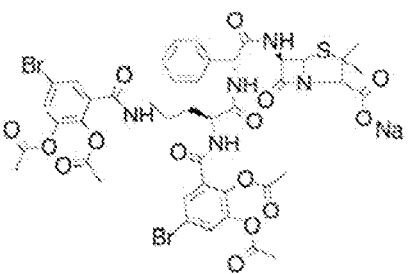 | 100 | 1083.7 | Solid | White | HKI | 1999 Box-1 | 1/11/2009 |
| ND-009137 | ND-009137.0001 | 9924070 | 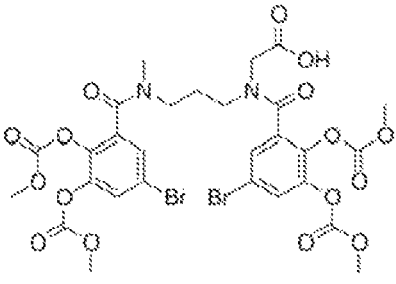 | 100 | 808.33 | Solid | White | HKI | 1999 Box-1 | 1/11/2009 |

FIG. 12AAI

| | | | | | | |
|---|---|---|---|---|---|---|
| ND-009141 | ND-009141.0002 | 99240083 | [structure] | 100 | 556.59 | Solid | White | HK1 | 1999 Box-1 | 1/11/2009 |
| ND-009143 | ND-009143.0002 | 99240085 | [structure] | 100 | 1073.1 | Solid | White | HK1 | 1999 Box-1 | 1/11/2009 |
| ND-009172 | ND-009172.0002 | 99240112 | [structure] | 100 | 1361.5 | Solid | White | HK1 | 1999 Box-1 | 1/11/2009 |
| ND-009190 | ND-009190.0002 | 99240131 | [structure] | 100 | 1119.7 | Solid | White | HK1 | 1999 Box-1 | 1/11/2009 |

FIG. 12AAJ

| ND-009195 | ND-009195.0002 | 9924141 | [structure] | 100 | 1262.4 | Solid | White | HK1 | 1999 Box-1 | 1/11/2009 |
| ND-009197 | ND-009197.0001 | 9924143 | [structure] | 100 | 554.55 | Solid | Brown | HK1 | 1999 Box-1 | 1/11/2009 |
| ND-008942 | ND-008942.0003 | 9824043 | [structure] | 100 | 539.53 | Solid | White | HK1 | 1999 Box-2 | 1/11/2009 |
| ND-009067 | ND-009067.0003 | 9924001 | [structure] | 100 | 903.82 | Solid | White | HK1 | 1999 Box-2 | 1/11/2009 |

FIG. 12AAK
| ND-009081 | ND-009084 | ND-009086 | ND-009089 |
|---|---|---|---|
| ND-009081.0002 | ND-009084.0001 | ND-009086.0002 | ND-009089.0002 |
| 9924015 | 9924018 | 9924020 | 9924023 |
| 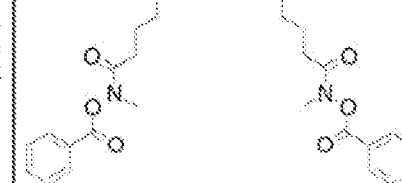 |  | 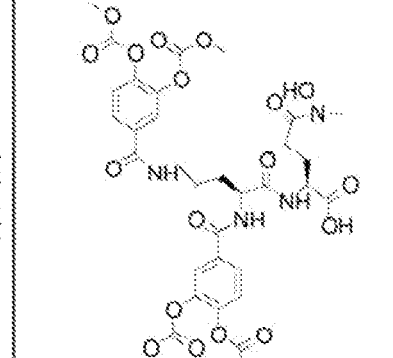 | 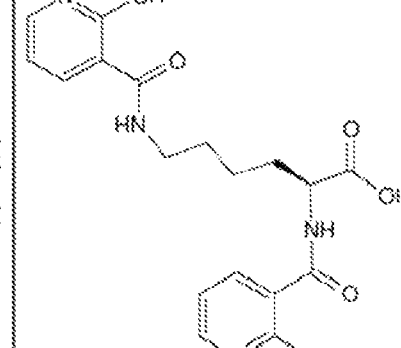 |
| 100 | 100 | 100 | 100 |
| 646.64 | 1166.2 | 794.67 | 388.37 |
| Solid | Solid | Solid | Solid |
| White | White | Tan | White |
| HKI | HKI | HKI | HKI |
| 1999 Box-2 | 1999 Box-2 | 1999 Box-2 | 1999 Box-2 |
| 1/11/2009 | 1/11/2009 | 1/11/2009 | 1/11/2009 |

FIG. 12AAL

| ND-009103 | ND-009113 | ND-009116 | ND-009117 |
|---|---|---|---|
| ND-009103.0002 | ND-009113.0002 | ND-009116.0001 | ND-009117.0002 |
| 9924039 | 9924048 | 9924051 | 9924052 |
| | | | |
| 100 | 100 | 100 | 100 |
| 650.54 | 682.67 | 654.62 | 1051.1 |
| Solid | Solid | Solid | Solid |
| White | White | Pink | White |
| HKI | HKI | HKI | HKI |
| 1999 Box-2 | 1999 Box-2 | 1999 Box-2 | 1999 Box-2 |
| 1/11/2009 | 1/11/2009 | 1/11/2009 | 1/11/2009 |

FIG. 12AAM
| ND-008982 | ND-008966 | ND-009122 | ND-009118 |
|---|---|---|---|
| ND-008982.0002 | ND-008966.0002 | ND-009122.0002 | ND-009118.0002 |
| 9824083 | 9824067 | 9824057 | 9824053 |
| 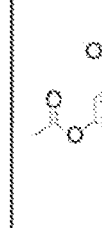 |  |  |  |
| 80 | 80 | 100 | 100 |
| 699.64 | 656.66 | 1238.2 | 1123.1 |
| Solid | Solid | Solid | Solid |
| White | White | White | White |
| HK1 | HK1 | HK1 | HK1 |
| 1998 Box-1 | 1998 Box-1 | 1999 Box-2 | 1999 Box-2 |
| 1/11/2009 | 1/11/2009 | 1/11/2009 | 1/11/2009 |

FIG. 12AAN
| ND-008691 | ND-008699 | ND-009052 | ND-009054 |
|---|---|---|---|
| ND-008691.0001 | ND-008699.0001 | ND-009052.0001 | ND-009054.0001 |
| 95428 | 94477 | 9824149 | 9824151 |
| 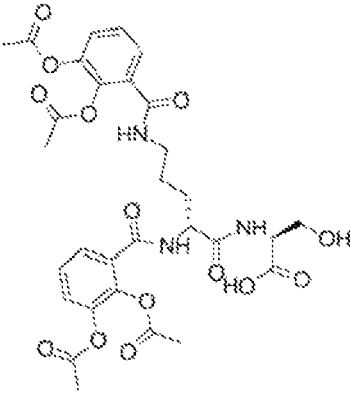 | 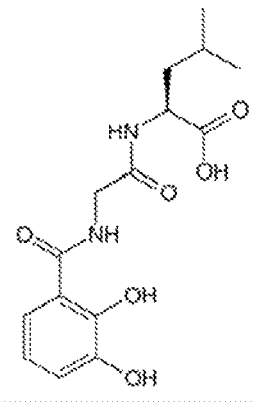 | 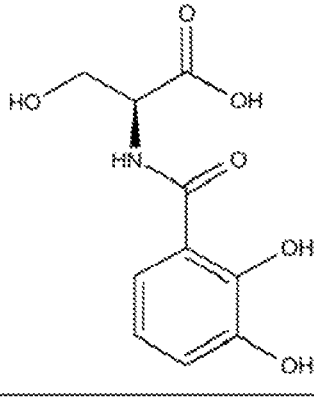 | 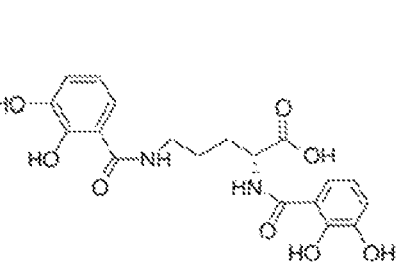 |
| 50 | 50 | 60 | 70 |
| 404.37 | 241.2 | 324.33 | 659.59 |
| Solid | Solid | Solid | Solid |
| White | White | Brown | Purple |
| HKI | HKI | HKI | HKI |
| Yellow-1994-2000 | Yellow-1994-2000 | 1998 Box-3 | 1998 Box-3 |
| 1/11/2009 | 1/11/2009 | 1/11/2009 | 1/11/2009 |

FIG. 12AAO
| ND-009239 | ND-009239.0001 | 10024038 |  | 50 | 662.64 | Solid | White | HKI | 1996 Box | 1/11/2009 |
| ND-009267 | ND-009267.0001 | 10024066 | 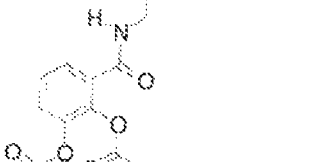 | 50 | 931.96 | Solid | White | HKI | 1996 Box | 1/11/2009 |
| ND-008780 | ND-008780.0002 | 9724029 | 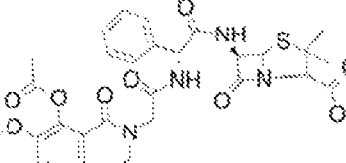 | 50 | 309.23 | Solid | White | HKI | 1997 Box-1 | 1/11/2009 |
| ND-008815 | ND-008815.0001 | 9724071 | 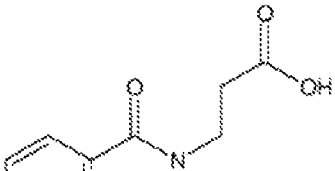 | 50 | 431.35 | Solid | Tan | HKI | 1997 Box-2 | 1/11/2009 |

FIG. 12AAP

| | | | |
|---|---|---|---|
| ND-008817<br>ND-008817.0001<br>9724073 | [structure] | 50<br>220.18<br>Solid<br>White | HKI<br>1997 Box-2<br>1/11/2009 |
| ND-008879<br>ND-008879.0001<br>9724122 | [structure] | 50<br>690.03<br>Solid<br>Yellow | HKI<br>1997 Box-2<br>1/11/2009 |
| ND-008883<br>ND-008883.0001<br>9724127 | [structure] | 50<br>575.5<br>Solid<br>White | HKI<br>1997 Box-2<br>1/11/2009 |
| ND-008886<br>ND-008886.0001<br>9724130 | [structure] | 50<br>841.71<br>Solid<br>White | HKI<br>1997 Box-2<br>1/11/2009 |

FIG. 12AAQ
| ND-008887 | ND-008887.0001 | 9724131 | 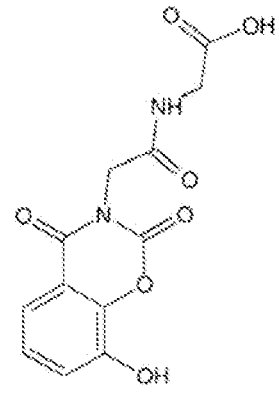 | 50 | 294.22 | Solid | White | HKI | 1997 Box-2 | 1/11/2009 |
|---|---|---|---|---|---|---|---|---|---|---|
| ND-008948 | ND-008948.0002 | 9824049 | 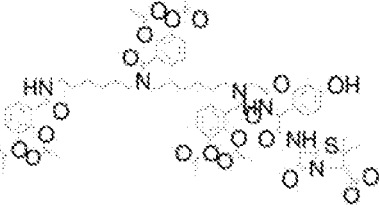 | 50 | 1281.3 | Solid | White | HKI | 1998 Box-1 | 1/11/2009 |
| ND-008949 | ND-008949.0002 | 9824050 | 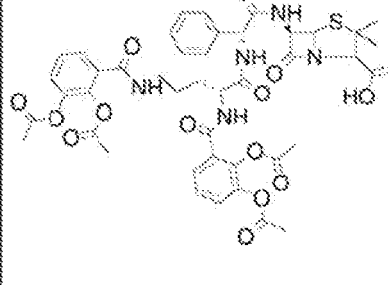 | 50 | 903.91 | Solid | White | HKI | 1998 Box-1 | 1/11/2009 |
| ND-008957 | ND-008957.0002 | 9824058 | | 50 | 1263.5 | Solid | White | HKI | 1998 Box-1 | 1/11/2009 |

FIG. 12AAR

| ND-008960 | ND-008981 | ND-009002 | ND-009001 |
|---|---|---|---|
| ND-008960.0002 | ND-008981.0002 | ND-009002.0002 | ND-009001.0002 |
| 9824061 | 9824082 | 9824104 | 9824105 |
| | | | |
| 50 | 50 | 50 | 50 |
| 1361.2 | 820.78 | 896.72 | 1228.1 |
| Solid | Solid | Solid | Solid |
| White | White | White | White |
| HKI | HKI | HKI | HKI |
| 1998 Box-1 | 1998 Box-1 | 1998 Box-3 | 1998 Box-3 |
| 1/11/2009 | 1/11/2009 | 1/11/2009 | 1/11/2009 |

FIG. 12AAS
| ND-009007 | ND-009007.0002 | 9824107 | 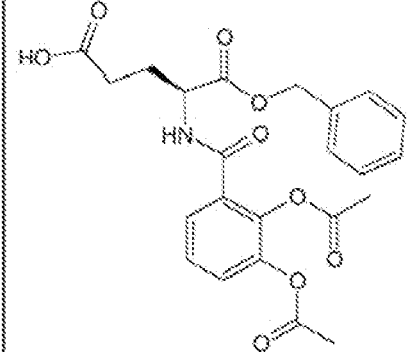 | 50 | 457.43 | Solid | White | HKI | 1998 Box-3 | 1/11/2009 |
|---|---|---|---|---|---|---|---|---|---|---|
| ND-009018 | ND-009018.0001 | 9824118 | 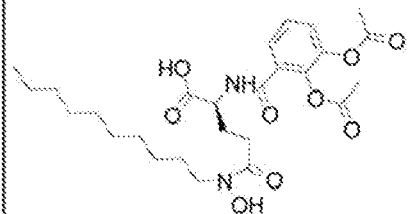 | 50 | 522.59 | Solid | Tan | HKI | 1998 Box-3 | 1/11/2009 |
| ND-009019 | ND-009019.0001 | 9824119 | 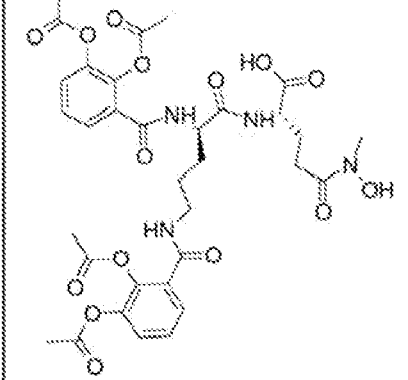 | 50 | 730.67 | Solid | Tan | HKI | 1998 Box-3 | 1/11/2009 |
| ND-009021 | ND-009021.0001 | 9824121 | 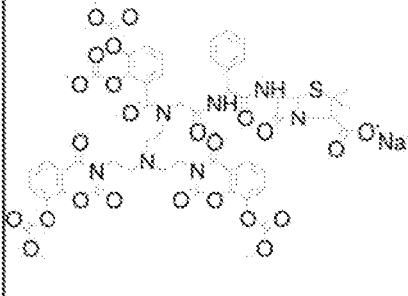 | 50 | 1250.1 | Solid | White | HKI | 1998 Box-3 | 1/11/2009 |

FIG. 12AAT
| ND-009059 | ND-009053 | ND-009034 | ND-009025 |
|---|---|---|---|
| ND-009059.0001 | ND-009053.0001 | ND-009034.0001 | ND-009025.0001 |
| 9824156 | 9824150 | 9824134 | 9824125 |
| 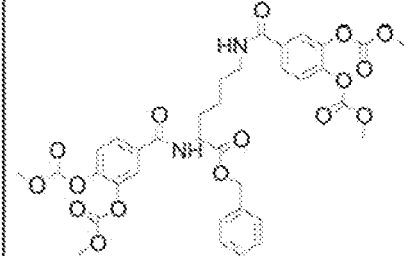 | 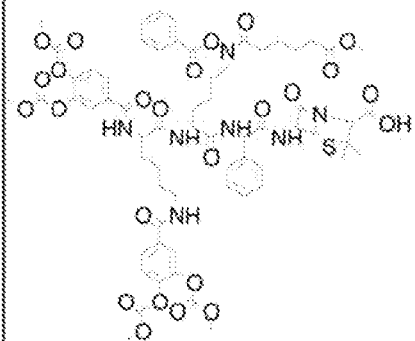 | 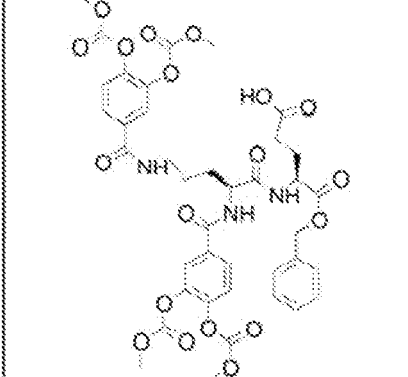 | 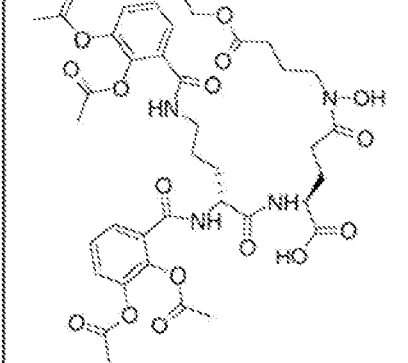 |
| 50 | 50 | 50 | 50 |
| 830.79 | 855.75 | 1372.4 | 740.66 |
| Solid | Solid | Solid | Solid |
| Brown | White | White | White |
| HKI | HKI | HKI | HKI |
| 1998 Box-3 | 1998 Box-3 | 1998 Box-3 | 1998 Box-3 |
| 1/11/2009 | 1/11/2009 | 1/11/2009 | 1/11/2009 |

FIG. 12AAU
| ND-009271 | ND-009271.0001 | 10024003 | 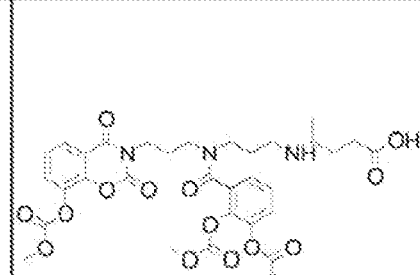 | 50 | 703.65 | Solid | White | HK1 | 1998 Box-3 | 1/11/2009 |
| ND-009235 | ND-009235.0003 | 10024034 | 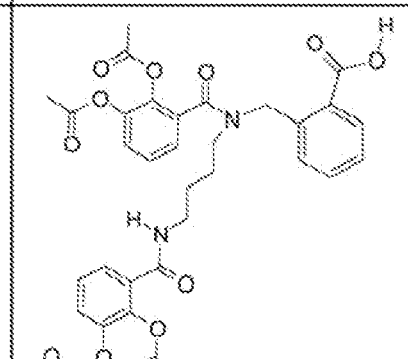 | 50 | 662.64 | Solid | White | HK1 | 1998 Box-3 | 1/11/2009 |
| ND-009267 | ND-009267.0002 | 10024066 | 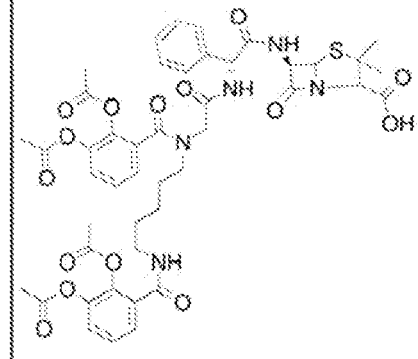 | 50 | 931.96 | Solid | White | HK1 | 1998 Box-3 | 1/11/2009 |
| ND-008717 | ND-008717.0001 | 9624012 | 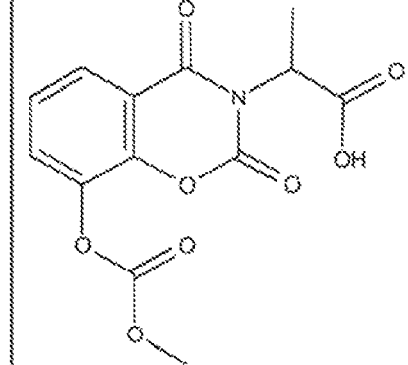 | 50 | 309.23 | Solid | White | HK1 | 1999 Box-1 | 1/11/2009 |

FIG. 12AAV

| ND-008718 | ND-008718.0001 | 9624013 | [structure] | 50 | 371.3 | Solid | White | HKI | 1999 Box-1 | 1/11/2009 |
|---|---|---|---|---|---|---|---|---|---|---|
| ND-008722 | ND-008722.0001 | 9624016 | [structure] | 50 | 698.65 | Solid | White | HKI | 1999 Box-1 | 1/11/2009 |
| ND-008723 | ND-008723.0001 | 9624018 | [structure] | 50 | 350.32 | Solid | White | HKI | 1999 Box-1 | 1/11/2009 |
| ND-008724 | ND-008724.0001 | 9624019 | [structure] | 50 | 308.24 | Solid | White | HKI | 1999 Box-1 | 1/11/2009 |

FIG. 12AAW

| ND-008742 | ND-008731 | ND-009138 | ND-009146 |
|---|---|---|---|
| ND-008742.0001 | ND-008731.0001 | ND-009138.0002 | ND-009146.0002 |
| 9624039 | 9624045 | 9924071 | 9924088 |
| (structure) | (structure) | (structure) | (structure) |
| 50 | 50 | 50 | 50 |
| 237.17 | 556.6 | 1139.7 | 902.9 |
| Solid | Solid | Solid | Solid |
| White | Tan | White | White |
| HKI | HKI | HKI | HKI |
| 1999 Box-1 | 1999 Box-1 | 1999 Box-1 | 1999 Box-1 |
| 1/11/2009 | 1/11/2009 | 1/11/2009 | 1/11/2009 |

FIG. 12AAX

| ND-009160 ND-009160.0002 9924100 | [structure] | 50 | 1048.1 | Solid | White | HK1 | 1999 Box-1 | 1/11/2009 |
|---|---|---|---|---|---|---|---|---|
| ND-009162 ND-009162.0002 9924102 | [structure] | 50 | 1021.9 | Solid | White | HK1 | 1999 Box-1 | 1/11/2009 |
| ND-009174 ND-009174.0002 9924114 | [structure: 2,4-dichloro-3,6-dihydroxybenzoic acid] | 50 | 223.01 | Solid | Yellow | HK1 | 1999 Box-1 | 1/11/2009 |
| ND-009175 ND-009175.0002 9924115 | [structure] | 50 | 1047.9 | Solid | White | HK1 | 1999 Box-1 | 1/11/2009 |

FIG. 12AAY
| ND-009180 | ND-009180.0002 | 9924120 | 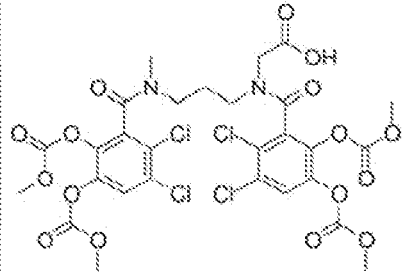 | 50 | 788.32 | Solid | White | HKI | 1999 Box-1 | 1/11/2009 |
| ND-009183 | ND-009183.0002 | 9924124 | 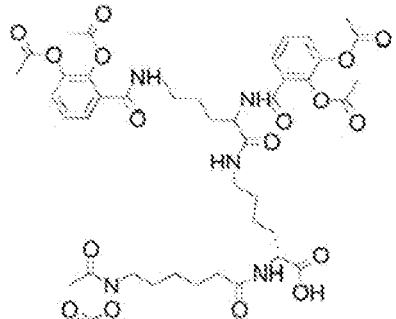 | 50 | 990.02 | Solid | Yellow | HKI | 1999 Box-1 | 1/11/2009 |
| ND-009186 | ND-009186.0002 | 9924127 | 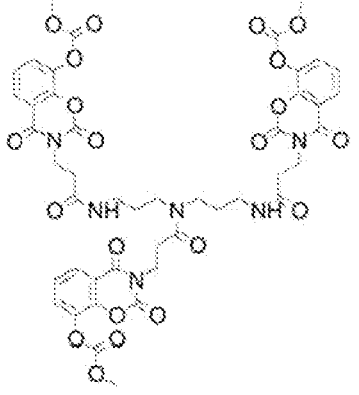 | 50 | 1004.9 | Solid | White | HKI | 1999 Box-1 | 1/11/2009 |
| ND-009191 | ND-009191.0003 | 9924132 | 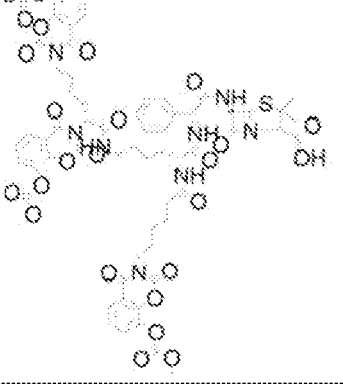 | 50 | 1379.3 | Solid | White | HKI | 1999 Box-1 | 1/11/2009 |

FIG. 12AAZ

| ND-009077 | ND-009072 | ND-009070 | ND-009196 |
|---|---|---|---|
| ND-009077.0002 | ND-009072.0002 | ND-009070.0002 | ND-009196.0003 |
| 9924011 | 9924006 | 9924004 | 9924142 |
| | | | |
| 50 | 50 | 50 | 50 |
| 438.43 | 151.16 | 686.66 | 1326.2 |
| Solid | Solid | Solid | Solid |
| Tan | White | White | White |
| HKI | HKI | HKI | HKI |
| 1999 Box-2 | 1999 Box-2 | 1999 Box-2 | 1999 Box-1 |
| 1/11/2009 | 1/11/2009 | 1/11/2009 | 1/11/2009 |

FIG. 12AAAA
| ND-009078 | ND-009079 | ND-009083 | ND-009085 |
|---|---|---|---|
| ND-009078.0002 | ND-009079.0003 | ND-009083.0002 | ND-009085.0001 |
| 9924012 | 9924013 | 9924017 | 9924019 |
| 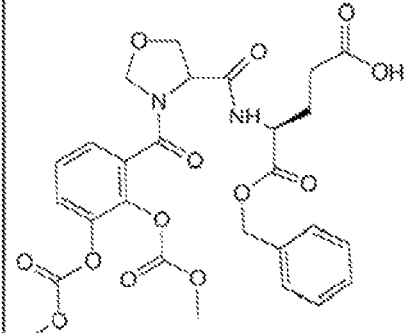 | 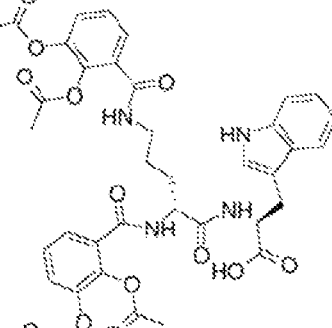 | 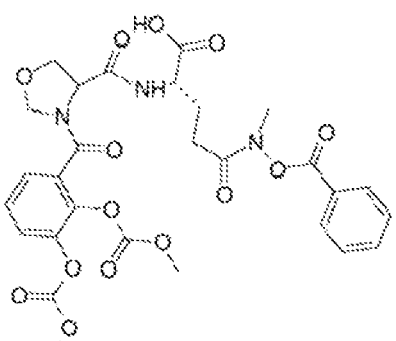 | 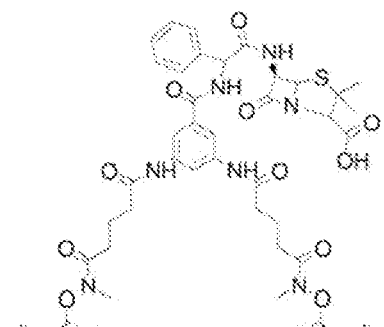 |
| 50 | 50 | 50 | 50 |
| 588.52 | 758.73 | 631.64 | 978.03 |
| Solid | Solid | Solid | Solid |
| Clear | White | White | White |
| HKI | HKI | HKI | HKI |
| 1999 Box-2 | 1999 Box-2 | 1999 Box-2 | 1999 Box-2 |
| 1/11/2009 | 1/11/2009 | 1/11/2009 | 1/11/2009 |

FIG. 12AAAB
| ND-009088 | ND-009108 | ND-009109 | ND-009119 |
|---|---|---|---|
| ND-009088.0002 | ND-009108.0002 | ND-009109.0002 | ND-009119.0002 |
| 9924022 | 9924043 | 9924044 | 9924054 |
| 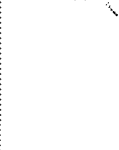 | 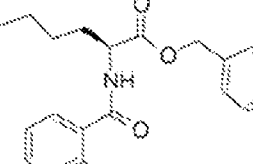 | 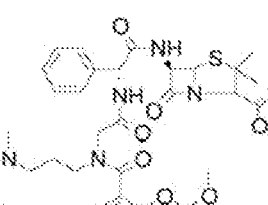 | 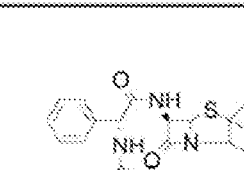 |
| 50 | 50 | 50 | 50 |
| 478.5 | 981.93 | 949.89 | 1320.4 |
| Solid | Solid | Solid | Solid |
| White | White | White | White |
| HK1 | HK1 | HK1 | HK1 |
| 1999 Box-2 | 1999 Box-2 | 1999 Box-2 | 1999 Box-2 |
| 1/11/2009 | 1/11/2009 | 1/11/2009 | 1/11/2009 |

FIG. 12AAAC
| ND-008911 | ND-009134 | ND-009123 | ND-009123 |
|---|---|---|---|
| ND-008911.0002 | ND-009134.0001 | ND-009123.0003 | ND-009123.0002 |
| 9924012 | 9924067 | 9924058 | 9924058 |
| 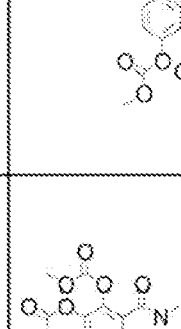 | 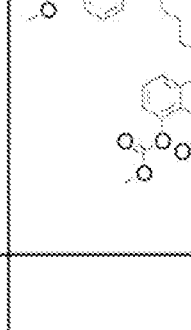 | 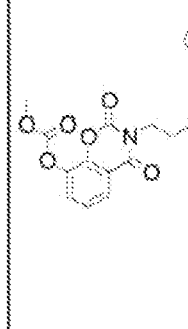 | 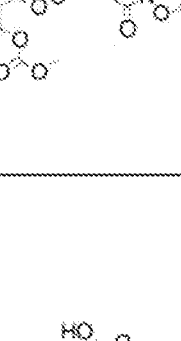 |
| 30 | 40 | 50 | 50 |
| 997.9 | 971.87 | 912.8 | 912.8 |
| Solid | Solid | Solid | Solid |
| White | White | White | White |
| HKI | HKI | HKI | HKI |
| 1998 Box-1 | 1996 Box | 1999 Box-2 | 1999 Box-2 |
| 1/11/2009 | 1/11/2009 | 1/11/2009 | 1/11/2009 |

FIG. 12AAAD

| | | | | | | | |
|---|---|---|---|---|---|---|---|
| ND-008950 | ND-008950.0002 | 98240051 | | 30 | 1020 | Solid White | HKI 1998 Box-1 1/11/2009 |
| ND-008953 | ND-008953.0003 | 98240054 | | 30 | 379.28 | Solid White | HKI 1998 Box-1 1/11/2009 |
| ND-008968 | ND-008968.0002 | 98240069 | | 30 | 457.39 | Solid Yellow | HKI 1998 Box-1 1/11/2009 |
| ND-009010 | ND-009010.0001 | 98240111 | | 30 | 730.31 | Solid White | HKI 1998 Box-3 1/11/2009 |

FIG. 12AAAE
| | | | |
|---|---|---|---|
| ND-009082 | ND-008677 | ND-009238 | ND-009043 |
| ND-009082.0002 | ND-008677.0002 | ND-009238.0002 | ND-009043.0001 |
| 9924016 | 10024013 | 10024037 | 9024143 |
| 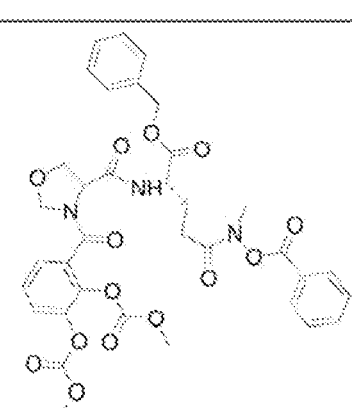 | 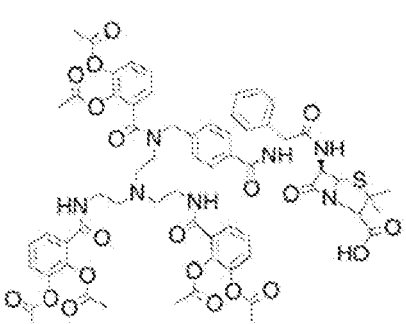 | 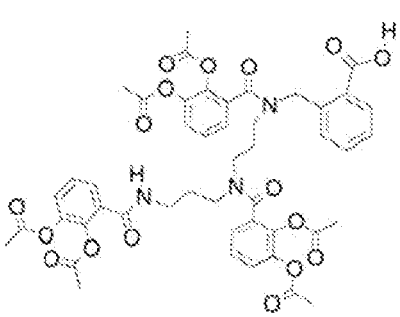 | 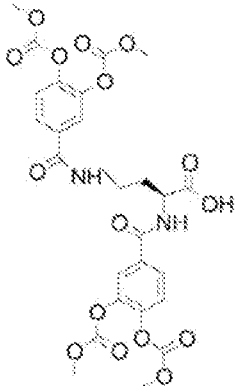 |
| 25 | 25 | 30 | 30 |
| 721.66 | 1272.3 | 925.89 | 636.52 |
| Solid | Solid | Solid | Solid |
| White | White | White | White |
| HKI | HKI | HKI | HKI |
| 1999 Box-2 | 1996 Box | 1998 Box-3 | 1998 Box-3 |
| 1/11/2009 | 1/11/2009 | 1/11/2009 | 1/11/2009 |

FIG. 12AAAF

| ND-008677 | ND-008677.0001 | 10024013 | [structure] | 20 | 1272.3 | solid | off white | HK1 | DMSO-1996 Box | 1/8/2009 |
|---|---|---|---|---|---|---|---|---|---|---|
| ND-009268 | ND-009268.0001 | 94431 | [structure] | 20 | Solid | White | | HK1 | Yellow-1994-2000 | 1/11/2009 |
| ND-009274 | ND-009274.0001 | 10024070 | [structure] | 20 | 572.52 | Solid | White | HK1 | Yellow-1994-2000 | 1/11/2009 |
| ND-009251 | ND-009251.0002 | 10024049 | [structure] | 20 | 692.67 | Solid | White | HK1 | Polyamine-1997-2000 | 1/11/2009 |

FIG. 12AAAG

| ND-008270 | ND-009266 | ND-008998 | ND-008789 |
|---|---|---|---|
| ND-009270.0002 | ND-009266.0001 | ND-008998.0001 | ND-008789.0001 |
| 10024067 | 10024065 | 9824102 | 9724037 |
| [structure] | [structure] | [structure] | [structure] |
| 20 | 20 | 20 | 20 |
| 889.88 | 903.91 | 1283.1 | 1087.9 |
| Solid | Solid | Solid | Solid |
| White | White | White | White |
| HKI | HKI | HKI | HKI |
| 1996 Box | 1996 Box | 1996 Box | 1996 Box |
| 1/11/2009 | 1/11/2009 | 1/11/2009 | 1/11/2009 |

FIG. 12AAAH

| ND-008847 | ND-008811 | ND-008785 | ND-008781 |
|---|---|---|---|
| ND-008847.0002 | ND-008811.0001 | ND-008785.0001 | ND-008781.0001 |
| 9724094 | 9724067 | 9724034 | 9724030 |
| | | | |
| 20 | 20 | 20 | 20 |
| 666.98 | 577.54 | 734.58 | 676.58 |
| Solid | Solid | Solid | Solid |
| White | Yellow | White | White |
| HK1 | HK1 | HK1 | HK1 |
| 1997 Box-1 | 1997 Box-1 | 1997 Box-1 | 1997 Box-1 |
| 1/11/2009 | 1/11/2009 | 1/11/2009 | 1/11/2009 |

FIG. 12AAAf
| ND-008882 | ND-008881 | ND-008834 | ND-008854 |
|---|---|---|---|
| ND-008882.0001 | ND-008881.0001 | ND-008834.0001 | ND-008854.0001 |
| 9724124 | 9724123 | 9724081 | 9724101 |
| 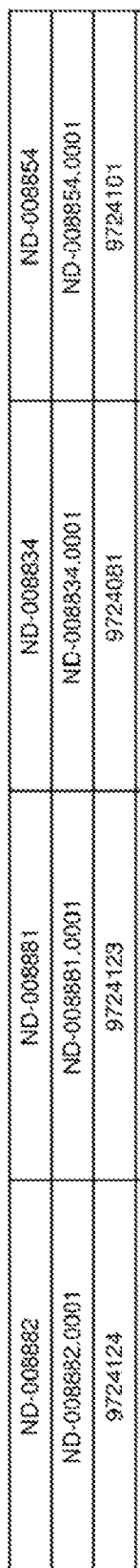 | 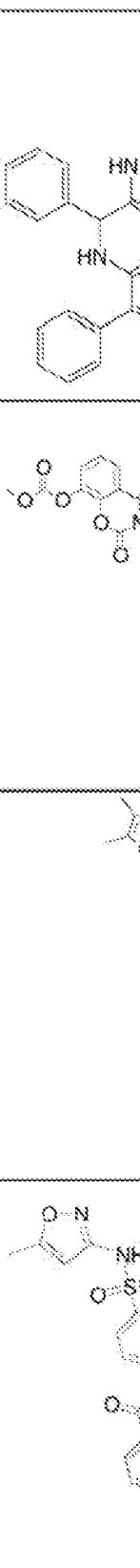 | 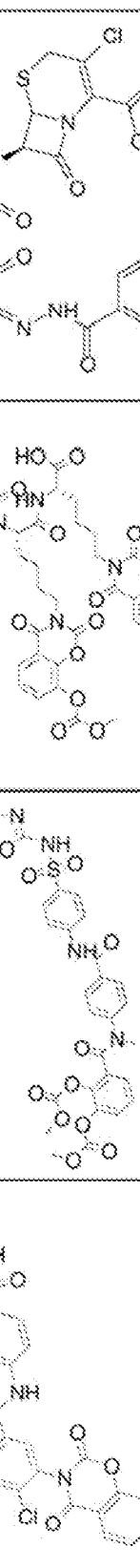 | 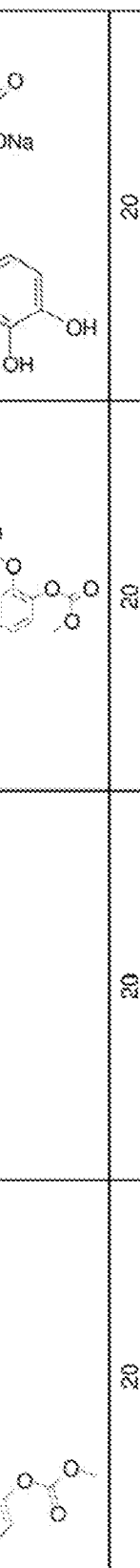 |
| 20 | 20 | 20 | 20 |
| 626.98 | 652.63 | 934.77 | 672.04 |
| Solid | Solid | Solid | Solid |
| White | White | White | White |
| HKI | HKI | HKI | HKI |
| 1997 Box-2 | 1997 Box-2 | 1997 Box-2 | 1997 Box-1 |
| 1/11/2009 | 1/11/2009 | 1/11/2009 | 1/11/2009 |

FIG. 12AAAJ
| ND-009066 | ND-009057 | ND-009003 | ND-008897 |
|---|---|---|---|
| ND-009066.0001 | ND-009057.0001 | ND-009003.0002 | ND-008897.0001 |
| 9824164 | 9824154 | 9824031 | 9824007 |
| 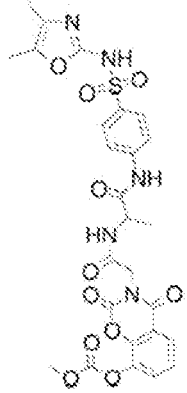 | 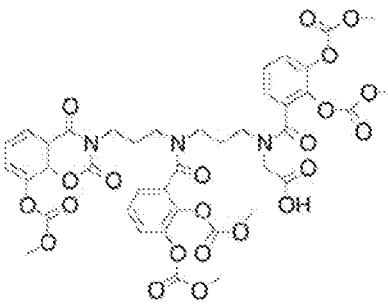 | 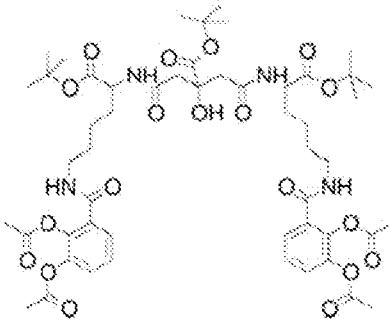 | 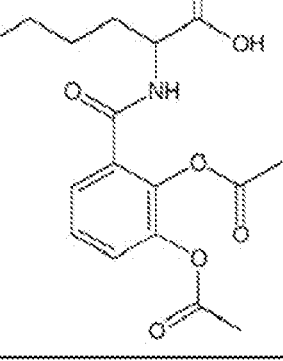 |
| 20 | 20 | 20 | 20 |
| 366.37 | 1057.1 | 913.74 | 615.57 |
| Oil | Solid | Solid | Solid |
| Black | Tan | White | White |
| HKI | HKI | HKI | HKI |
| 1998 Box-3 | 1998 Box-3 | 1998 Box-1 | 1998 Box-1 |
| 1/11/2009 | 1/11/2009 | 1/11/2009 | 1/11/2009 |

FIG. 12AAAK
| ND-009224 | ND-008719 | ND-008741 | ND-008743 |
|---|---|---|---|
| ND-009224.0002 | ND-008719.0001 | ND-008741.0001 | ND-008743.0001 |
| 10024023 | 9624014 | 9624038 | 9624040 |
| 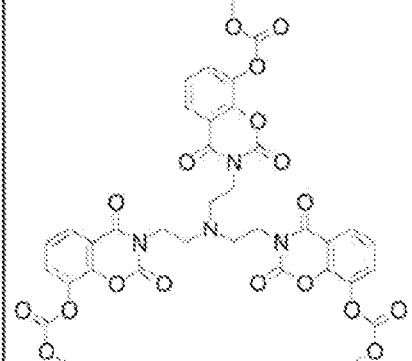 | 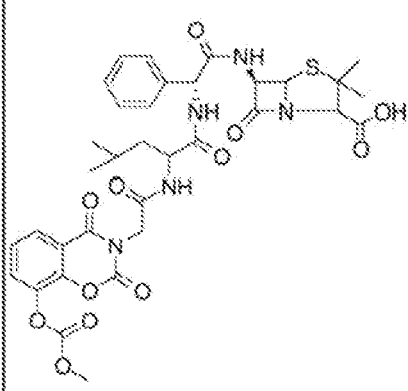 | 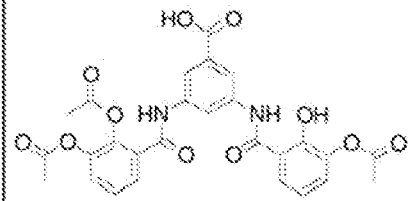 | 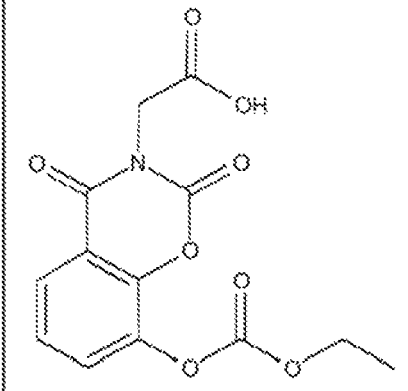 |
| 20 | 20 | 20 | 20 |
| 806.64 | 739.75 | 550.47 | 309.23 |
| Solid | Solid | Solid | Solid |
| White | White | Tan | White |
| HK1 | HK1 | HK1 | HK1 |
| 1998 Box-3 | 1999 Box-1 | 1999 Box-1 | 1999 Box-1 |
| 1/11/2009 | 1/11/2009 | 1/11/2009 | 1/11/2009 |

FIG. 12AAAL.

| ND-008745 | ND-008745.0001 | 9624050 | [structure] | 20 | 508.43 | Solid | Tan | HKI | 1999 Box-1 | 1/11/2009 |
|---|---|---|---|---|---|---|---|---|---|---|
| ND-009225 | ND-009225.0003 | 10024024 | [structure] | 20 | 977.79 | Solid | White | HKI | 1999 Box-2 | 1/11/2009 |
| ND-008913 | ND-008913.0001 | 9824014 | [structure] | 15 | 963.93 | Solid | Clear | HKI | Yellow-1994-2000 | 1/11/2009 |
| ND-009179 | ND-009179.0002 | 9824119 | [structure] | 15 | 339.08 | Solid | White | HKI | Yellow-1994-2000 | 1/11/2009 |

FIG. 12AAAM
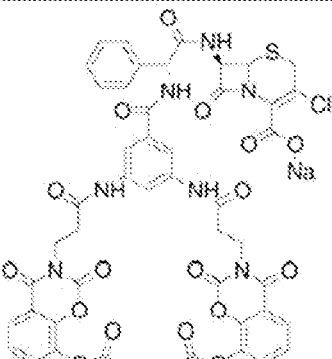

FIG. 12AAAN
| ND-008689 | ND-009155 | ND-009186 | ND-009187 |
|---|---|---|---|
| ND-008689.0001 | ND-009155.0001 | ND-009186.0001 | ND-009187.0001 |
| 95465 | 9924095 | 9924127 | 9924128 |
| 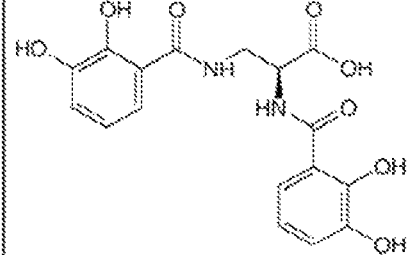 | 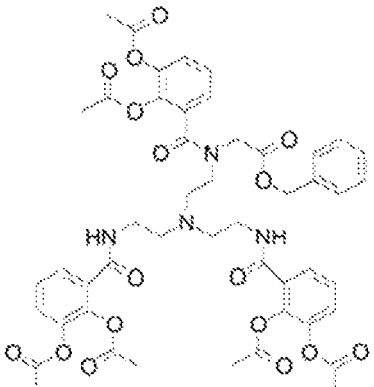 | 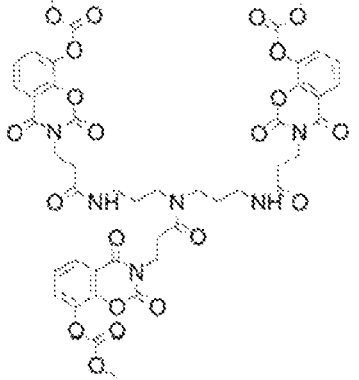 | 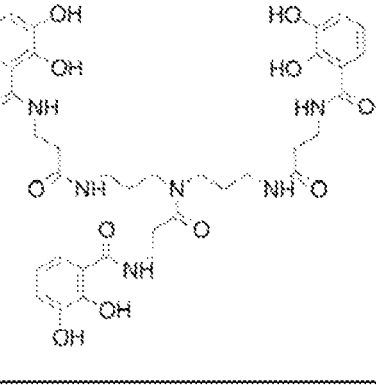 |
| 10 | 10 | 10 | 10 |
| 376.32 | 954.93 | 1004.9 | 752.77 |
| Solid | Solid | Solid | Solid |
| White | White | Tan | White |
| HKI | HKI | HKI | HKI |
| Yellow-1994-2000 | Yellow-1994-2000 | Yellow-1994-2000 | Yellow-1994-2000 |
| 1/11/2009 | 1/11/2009 | 1/11/2009 | 1/11/2009 |

FIG. 12AAAO

| ND-008894 | ND-008894.0001 | 9824004 | [structure] | 10 | 936.34 | Solid | White | HKI | Polyamine-1997-2000 | 1/11/2009 |
| --- | --- | --- | --- | --- | --- | --- | --- | --- | --- | --- |
| ND-008909 | ND-008909.0001 | 9824010 | [structure] | 10 | 787.75 | Solid | White | HKI | Polyamine-1997-2000 | 1/11/2009 |
| ND-008995 | ND-008995.0002 | 9824099 | [structure] | 10 | 188.57 | Solid | White | HKI | Polyamine-1997-2000 | 1/11/2009 |
| ND-009004 | ND-009004.0002 | 9824103 | [structure] | 10 | 317.09 | Solid | Tan | HKI | Polyamine-1997-2000 | 1/11/2009 |

FIG. 12AAAP

| ND-009277 | ND-009250 | ND-009229 | ND-009225 |
|---|---|---|---|
| ND-009277.0001 | ND-009250.0001 | ND-009229.0002 | ND-009225.0001 |
| 10024073 | 10024048 | 10024026 | 10024024 |
| (structure) | (structure) | (structure) | (structure) |
| 10 | 10 | 10 | 10 |
| 621.68 | 1520.5 | 890.91 | 977.79 |
| Solid | Solid | Solid | Solid |
| Tan | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAQ

| ND-008884 | ND-008826 | ND-009265 | ND-009235 |
|---|---|---|---|
| ND-008884.0001 | ND-008826.0001 | ND-009265.0001 | ND-009235.0001 |
| 9724128 | 95407 | 10024064 | 10024034 |
| | | | |
| 10 | 10 | 10 | 10 |
| 618.57 | 295.2 | 1257.3 | 662.64 |
| Solid | Solid | Solid | Solid |
| White | White | White | White |
| HKI | HKI | HKI | HKI |
| 1997 Box-2 | 1997 Box-1 | 1996 Box | 1996 Box |
| 1/11/2009 | 1/11/2009 | 1/11/2009 | 1/11/2009 |

FIG. 12AAAR
| ND-008909 | ND-009092 | ND-009097 | ND-009112 |
|---|---|---|---|
| ND-008909.0002 | ND-009092.0002 | ND-009097.0002 | ND-009112.0002 |
| 9924010 | 9924026 | 9924032 | 9924047 |
| 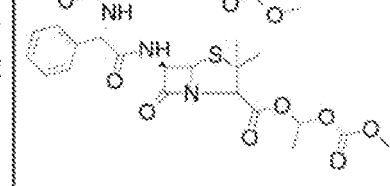 | 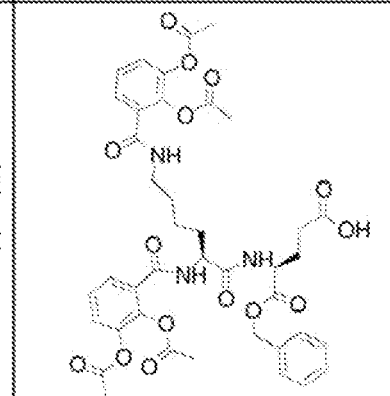 | 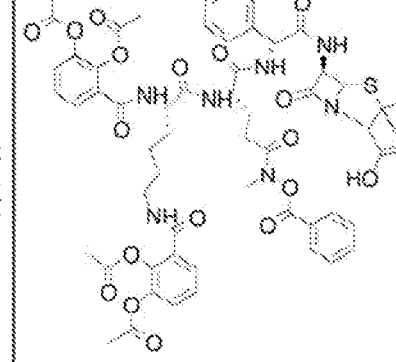 | 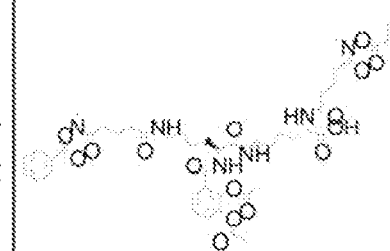 |
| 10 | 10 | 10 | 10 |
| 787.75 | 805.78 | 1180.2 | 989.03 |
| Solid | Solid | Solid | Solid |
| White | White | White | White |
| HKI | HKI | HKI | HKI |
| 1998 Box-1 | 1999 Box-2 | 1999 Box-2 | 1999 Box-2 |
| 1/11/2009 | 1/11/2009 | 1/11/2009 | 1/11/2009 |

FIG. 12AAAS
| ND-009017 | ND-008907 | ND-008943 | ND-009153 |
|---|---|---|---|
| ND-009017.0001 | ND-008907.0002 | ND-008943.0001 | ND-009153.0001 |
| 9824117 | 9824008 | 9824044 | 9824093 |
| 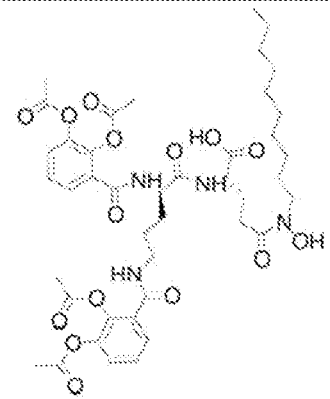 | 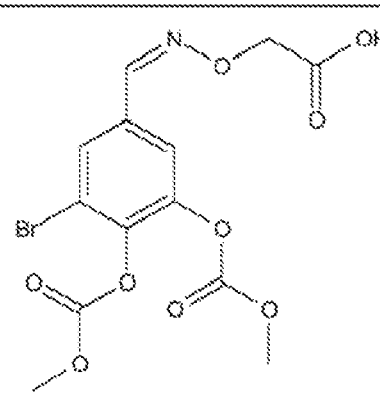 | 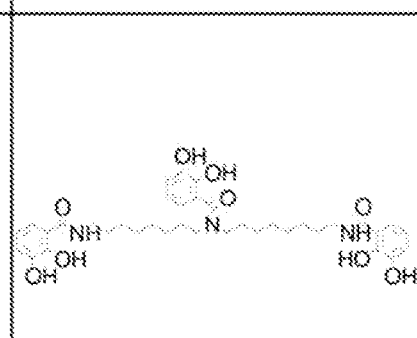 | 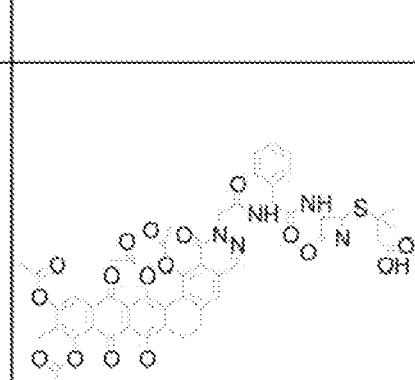 |
| 9.52 | 8 | 6 | 5 |
| 856.91 | 406.14 | 679.8 | 1044 |
| Solid | Solid | Solid | Solid |
| White | White | White | Orange |
| HKI | HKI | HKI | HKI |
| 1998 Box-2 | Polyamine-1997-2000 | 1998 Box-2 | 2000 Box-1 |
| 1/11/2009 | 1/11/2009 | 1/11/2009 | 1/9/2009 |

FIG. 12AAAT

| ND-009156 | ND-009154 | ND-009154 | ND-009153 |
|---|---|---|---|
| ND-009156.0001 | ND-009154.0002 | ND-009154.0001 | ND-009153.0002 |
| 9924096 | 9924094 | 9924094 | 9924093 |
| | | | |
| 5 | 5 | 5 | 5 |
| 1072.1 | 1060 | 1060 | 1044 |
| Solid | Solid | Solid | Solid |
| Orange | Orange | Orange | Orange |
| HKI | HKI | HKI | HKI |
| 2300 Box-1 | 2300 Box-1 | 2300 Box-1 | 2300 Box-1 |
| 1/9/2009 | 1/9/2009 | 1/9/2009 | 1/9/2009 |

FIG. 12AAAU
| ND-009157 | ND-009157.0001 | 9924097 | 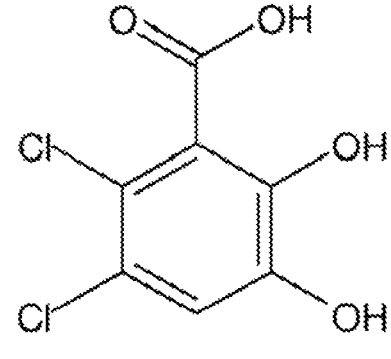 | 5 | 712.61 | Solid | Orange | HK1 | | 1/9/2009 |
|---|---|---|---|---|---|---|---|---|---|---|
| ND-009166 | ND-009166.0001 | 9924106 | 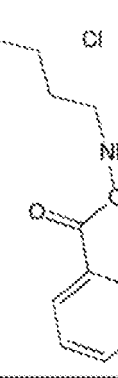 | 5 | 256.75 | Solid | Yellow | HK1 | 2000 Box-1 | 1/9/2009 |
| ND-009174 | ND-009174.0001 | 9924114 | 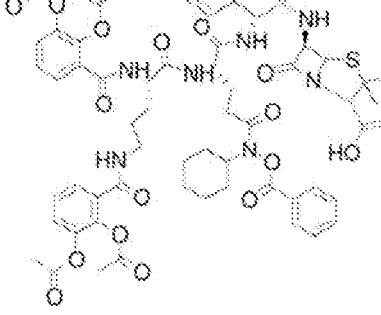 | 5 | 223.01 | Solid | White | HK1 | 2000 Box-1 | 1/9/2009 |
| ND-009177 | ND-009177.0001 | 9924117 | 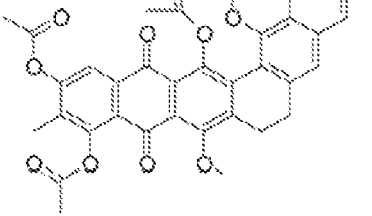 | 5 | 1234.3 | Solid | White | HK1 | | 1/9/2009 |

FIG. 12AAAV

| ND-009190 | ND-009190.0001 | 9924131 | (structure) | 5 | 1119.7 | Solid | White | HK1 | 2300 Box-1 | 1/9/2009 |
|---|---|---|---|---|---|---|---|---|---|---|
| ND-009191 | ND-009191.0001 | 9924132 | (structure) | 5 | 1379.3 | Solid | White | HK1 | 2300 Box-1 | 1/9/2009 |
| ND-009201 | ND-009201.0001 | 9924147 | (structure) | 5 | 223.25 | Solid | Tan | HK1 | | 1/9/2009 |
| ND-009202 | ND-009202.0001 | 9924148 | (structure) | 5 | 556.65 | Solid | Yellow | HK1 | 2300 Box-1 | 1/9/2009 |

FIG. 12AAAW

| ID | Sub-ID | Code | Structure | Val | MW | State | Color | Class | Group | Date |
|---|---|---|---|---|---|---|---|---|---|---|
| ND-008678 | ND-008678.0001 | 95420 | (structure) | 5 | 225.2 | Solid | White | HK1 | Yellow-1994-2000 | 1/11/2009 |
| ND-009165 | ND-009165.0001 | 9924105 | (structure) | 5 | 962.78 | Solid | White | HK1 | Yellow-1994-2000 | 1/11/2009 |
| ND-009185 | ND-009185.0002 | 9924126 | (structure) | 5 | 710.69 | Solid | White | HK1 | Yellow-1994-2000 | 1/11/2009 |
| ND-008910 | ND-008910.0001 | 9824011 | (structure) | 5 | 1034 | Solid | White | HK1 | Polyamine-1997-2000 | 1/11/2009 |

FIG. 12AAAX
| ND-008938 | ND-008938.0001 | 9824039 | 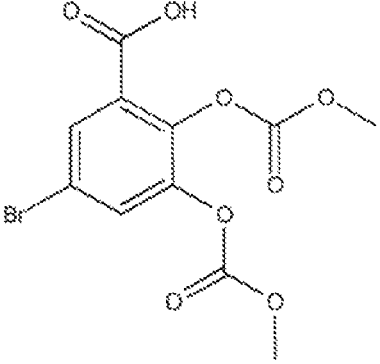 | 5 | 349.09 | Solid | White | HK1 | Polyamine-1997-2000 | 1/11/2009 |
|---|---|---|---|---|---|---|---|---|---|---|
| ND-008952 | ND-008952.0001 | 9824053 | 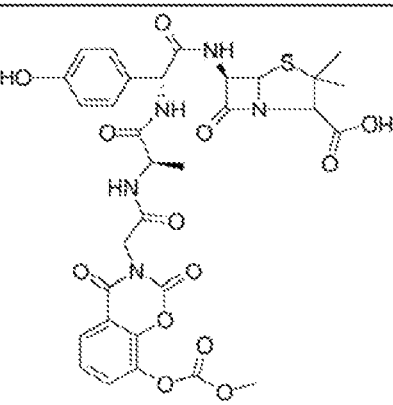 | 5 | 713.67 | Solid | White | HK1 | Polyamine-1997-2000 | 1/11/2009 |
| ND-008953 | ND-008953.0001 | 9824054 | 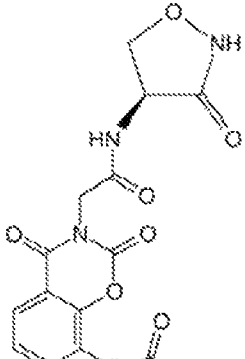 | 5 | 379.28 | Solid | White | HK1 | Polyamine-1997-2000 | 1/11/2009 |
| ND-008953 | ND-008953.0002 | 9824054 | 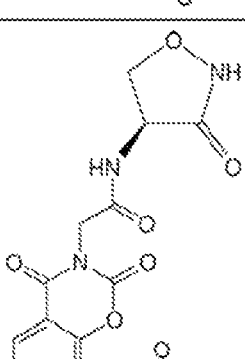 | 5 | 379.28 | Solid | White | HK1 | Polyamine-1997-2000 | 1/11/2009 |

FIG. 12AAAY

| ND-008955 | ND-008956 | ND-008957 | ND-008965 |
|---|---|---|---|
| ND-008955.0001 | ND-008956.0001 | ND-008957.0001 | ND-008965.0001 |
| 9824056 | 9824057 | 9824058 | 9824066 |
| (structure) | (structure) | (structure) | (structure) |
| 5 | 5 | 5 | 5 |
| 755.93 | 1235.3 | 1263.5 | 716.67 |
| Solid | Solid | Solid | Solid |
| White | Yellow | White | White |
| HK1 | HK1 | HK1 | HK1 |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAZ

| ND-008983 | ND-008976 | ND-008972 | ND-008969 |
|---|---|---|---|
| ND-008983.0002 | ND-008976.0001 | ND-008972.0001 | ND-008969.0001 |
| 9824084 | 9824077 | 9824073 | 9824070 |
| | | | |
| 5 | 5 | 5 | 5 |
| 385.33 | 904.89 | 788.78 | 1445.4 |
| Solid | Solid | Solid | Solid |
| Tan | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAA

| | | | |
|---|---|---|---|
| ND-008993 | ND-008994 | ND-009007 | ND-009006 |
| ND-008993.0001 | ND-008994.0001 | ND-009007.0001 | ND-009006.0001 |
| 9824095 | 9824098 | 9824107 | 9824108 |
| [structure] | [structure] | [structure] | [structure] |
| 5 | 5 | 5 | 5 |
| 1181.2 | 1179.1 | 457.43 | 572.52 |
| Solid | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAB

| ND-009006 | ND-009008 | ND-009009 | ND-009228 |
|---|---|---|---|
| ND-009006.0002 | ND-009008.0001 | ND-009009.0001 | ND-009228.0001 |
| 9824108 | 9824109 | 9824110 | 10024027 |
| | | | |
| 5 | 5 | 5 | 5 |
| 572.52 | 791.75 | 730.31 | 1189.1 |
| Solid | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAC

| | | | | | | | |
|---|---|---|---|---|---|---|---|
| ND-009234 | ND-009234.0001 | 10024033 | | 5 | 1178.2 | Solid | White | HK1 | Polyamine-1997-2000 | 1/11/2009 |
| ND-009235 | ND-009235.0002 | 10024034 | | 5 | 662.64 | Solid | White | HK1 | 1996 Box | 1/11/2009 |
| ND-009238 | ND-009238.0001 | 10024037 | | 5 | 925.89 | Solid | White | HK1 | 1996 Box | 1/11/2009 |
| ND-009240 | ND-009240.0001 | 10024040 | | 5 | 994.03 | Solid | White | HK1 | 1996 Box | 1/11/2009 |

FIG. 12AAAAD

| | ND-009171 | ND-009227 | ND-008841 | ND-008844 |
|---|---|---|---|---|
| | ND-009171.0001 | ND-009227.0001 | ND-008841.0002 | ND-008844.0001 |
| | 9924111 | 10024026 | 9724091 | 9724083 |
| Structure | (structure) | (structure) | (structure) | (structure) |
| | 4 | 5 | 5 | 5 |
| | 1248.3 | 1024.1 | 1288.3 | 1024.1 |
| | Solid | Solid | Solid | Solid |
| | White | White | White | White |
| | | | SODIUM SALT | |
| | HKI | HKI | HKI | HKI |
| | 2000 Box-1 | 1998 Box-3 | 1997 Box-2 | 1997 Box-2 |
| | 1/9/2009 | 1/11/2009 | 1/11/2009 | 1/11/2009 |

FIG. 12AAAAE
| ND-009172 | ND-009176 | ND-009212 | ND-009200 |
|---|---|---|---|
| ND-009172.0001 | ND-009176.0001 | ND-009212.0001 | ND-009200.0001 |
| 9924112 | 9924116 | 9924139 | 9924146 |
| 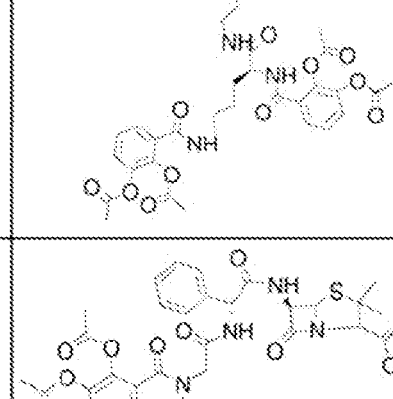 | 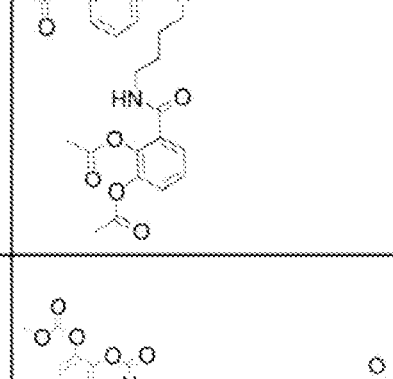 | 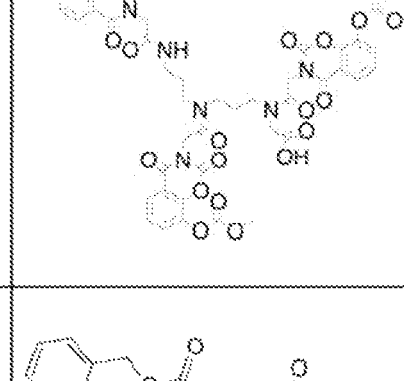 |  |
| 4 | 4 | 4 | 4 |
| 1361.5 | 917.93 | 1020.8 | 547.55 |
| Solid | Solid | Solid | Solid |
| White | White | White | White |
| HK1 | HK1 | HK1 | HK1 |
| 2300 Box-1 | 2300 Box-1 | 2300 Box-1 | 2300 Box-1 |
| 1/9/2009 | 1/9/2009 | 1/9/2009 | 1/9/2009 |

FIG. 12AAAAF

| ND-008975 | ND-008968 | ND-008963 | ND-008954 |
|---|---|---|---|
| ND-008975.0001 | ND-008968.0001 | ND-008963.0001 | ND-008954.0001 |
| 9824076 | 9824069 | 9824064 | 9824055 |
| (structure) | (structure) | (structure) | (structure) |
| 4 | 4 | 4 | 4 |
| 807.18 | 457.39 | 739.11 | 674.63 |
| Solid | Oil | Solid | Solid |
| White | Clear | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAG
| ND-008981 | ND-008991 | ND-008992 | ND-009005 |
|---|---|---|---|
| ND-008981.0001 | ND-008991.0001 | ND-008992.0001 | ND-009005.0001 |
| 9824082 | 9824093 | 9824094 | 9824106 |
|  |  | 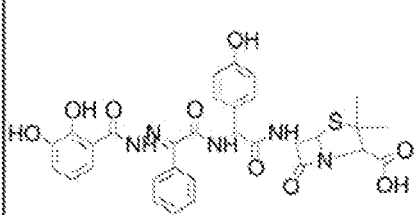 | 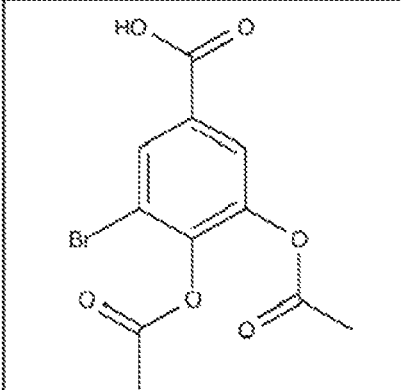 |
| 4 | 4 | 4 | 4 |
| 820.78 | 1284.6 | 647.66 | 317.09 |
| Solid | Solid | Solid | Solid |
| White | White | Tan | Brown |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAH
| ND-009121 | ND-009223 | ND-009278 | ND-008932 |
|---|---|---|---|
| ND-009121.0001 | ND-009223.0001 | ND-009278.0001 | ND-008932.0001 |
| 9924056 | 10024022 | 10024057 | 9824033 |
| 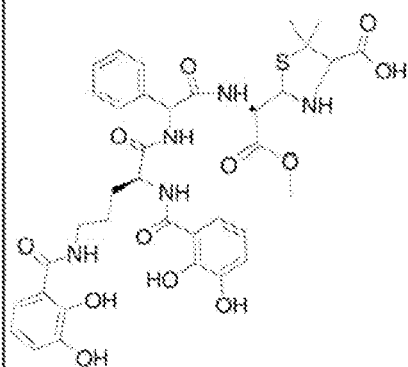 | 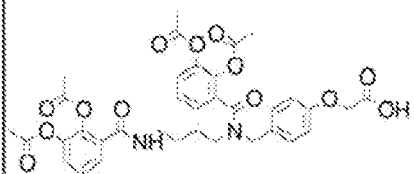 | 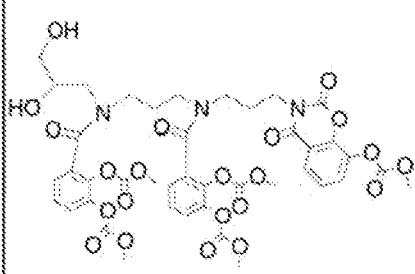 | 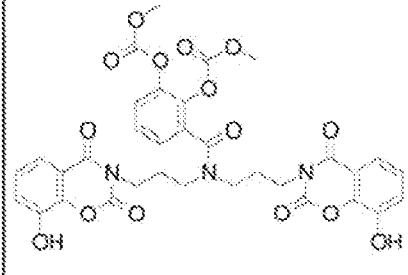 |
| 4 | 4 | 4 | 4 |
| 767.8 | 692.67 | 929.79 | 707.59 |
| Solid | Solid | Solid | Solid |
| White | White | White | White |
| HKI | HKI | HKI | HKI |
| Polyamine-1997-2000 | Polyamine-1997-2000 | Polyamine-1997-2000 | 1996 Box |
| 1/11/2009 | 1/11/2009 | 1/11/2009 | 1/11/2009 |

Figure 12:
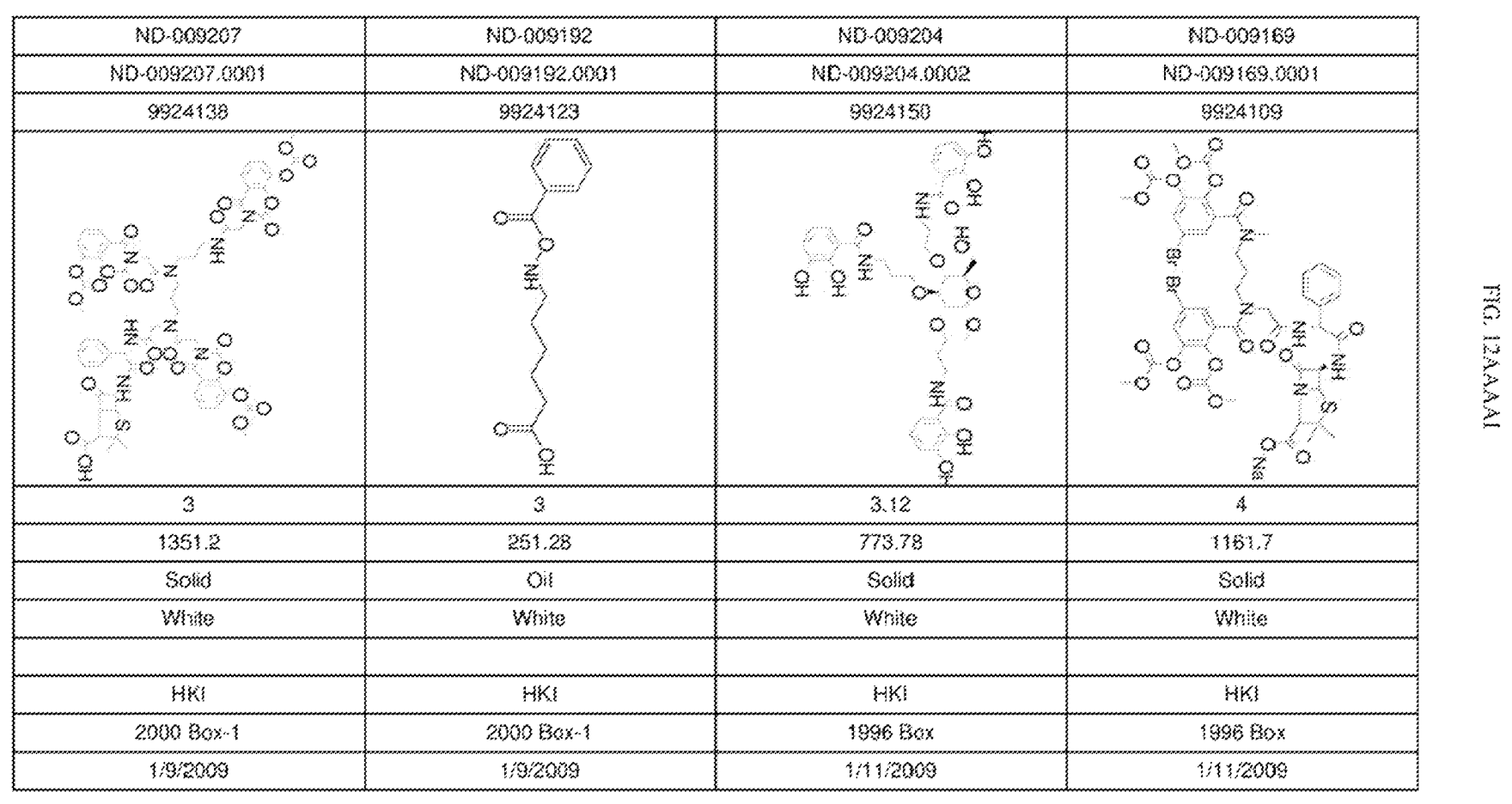

FIG. 12AAAAI

| | | | | | | | |
|---|---|---|---|---|---|---|---|
| ND-009169 | ND-009169.0301 | 9924109 | [structure] | 4 | 1161.7 | Solid | White | HK1 | 1996 Box | 1/11/2009 |
| ND-009204 | ND-009204.0002 | 9924150 | [structure] | 3.12 | 773.78 | Solid | White | HK1 | 1996 Box | 1/11/2009 |
| ND-009192 | ND-009192.0001 | 9924123 | [structure] | 3 | 251.28 | Oil | White | HK1 | 2000 Box-1 | 1/9/2009 |
| ND-009207 | ND-009207.0001 | 9924138 | [structure] | 3 | 1351.2 | Solid | White | HK1 | 2000 Box-1 | 1/9/2009 |

FIG. 12AAAAJ

| ND-008918 | ND-008911 | ND-009289 | ND-009226 |
|---|---|---|---|
| ND-008918.0001 | ND-008911.0001 | ND-009289.0001 | ND-009226.0001 |
| 9824019 | 9824012 | 10124001 | 10024025 |
| | | | |
| 3 | 3 | 3 | 3 |
| 436.17 | 997.9 | 917.93 | 725.7 |
| Solid | Solid | Solid | Solid |
| White | White | White | White |
| HKI | HKI | HKI | HKI |
| Polyamine-1997-2000 | Polyamine-1997-2000 | Yellow-1994-2000 | Yellow-1994-2000 |
| 1/11/2009 | 1/11/2009 | 1/11/2009 | 1/11/2009 |

FIG. 12AAAAK

| | ND-008996 | ND-008982 | ND-008970 | ND-008960 |
|---|---|---|---|---|
| | ND-008996.0001 | ND-008982.0001 | ND-008970.0001 | ND-008960.0001 |
| | 9824100 | 9824083 | 9824071 | 9824061 |
| | | | | |
| | 3 | 3 | 3 | 3 |
| | 329.65 | 699.64 | 873.83 | 1361.2 |
| | Solid | Solid | Solid | Solid |
| | White | White | White | White |
| | HKI | HKI | HKI | HKI |
| | Polyamine-1997-2000 | Polyamine-1997-2000 | Polyamine-1997-2000 | Polyamine-1997-2000 |
| | 1/11/2009 | 1/11/2009 | 1/11/2009 | 1/11/2009 |

FIG. 12AAAAL

| ND-008853 | ND-008839 | ND-008999 | ND-008997 |
|---|---|---|---|
| ND-008853.0001 | ND-008839.0001 | ND-008999.0001 | ND-008997.0001 |
| 9724100 | 9724099 | 9824096 | 9824101 |
| | | | |
| 3 | 3 | 3 | 3 |
| 716.07 | 678.6 | 1401.4 | 661.04 |
| Solid | Solid | Solid | Solid |
| White | White | White | White |
| HKI | HKI | HKI | HKI |
| 1997 Box-1 | 1997 Box-1 | 1996 Box | Polyamine-1997-2000 |
| 1/11/2009 | 1/11/2009 | 1/11/2009 | 1/11/2009 |

FIG. 12AAAAM

| ND-009141 | ND-009142 | ND-009146 | ND-009163 |
|---|---|---|---|
| ND-009141.0001 | ND-009142.0001 | ND-009146.0001 | ND-009163.0001 |
| 9924083 | 9924084 | 9924088 | 9924103 |
| (structure) | (structure) | (structure) | (structure) |
| 2 | 2 | 2 | 2 |
| 556.59 | 735.76 | 902.9 | 228.7 |
| Solid | Solid | Solid | Solid |
| White | White | White | White |
| HKI | HKI | HKI | HKI |
| 2300 Box-1 | 2300 Box-1 | 2300 Box-1 | 2300 Box-1 |
| 1/9/2009 | 1/9/2009 | 1/9/2009 | 1/9/2009 |

FIG. 12AAAAN
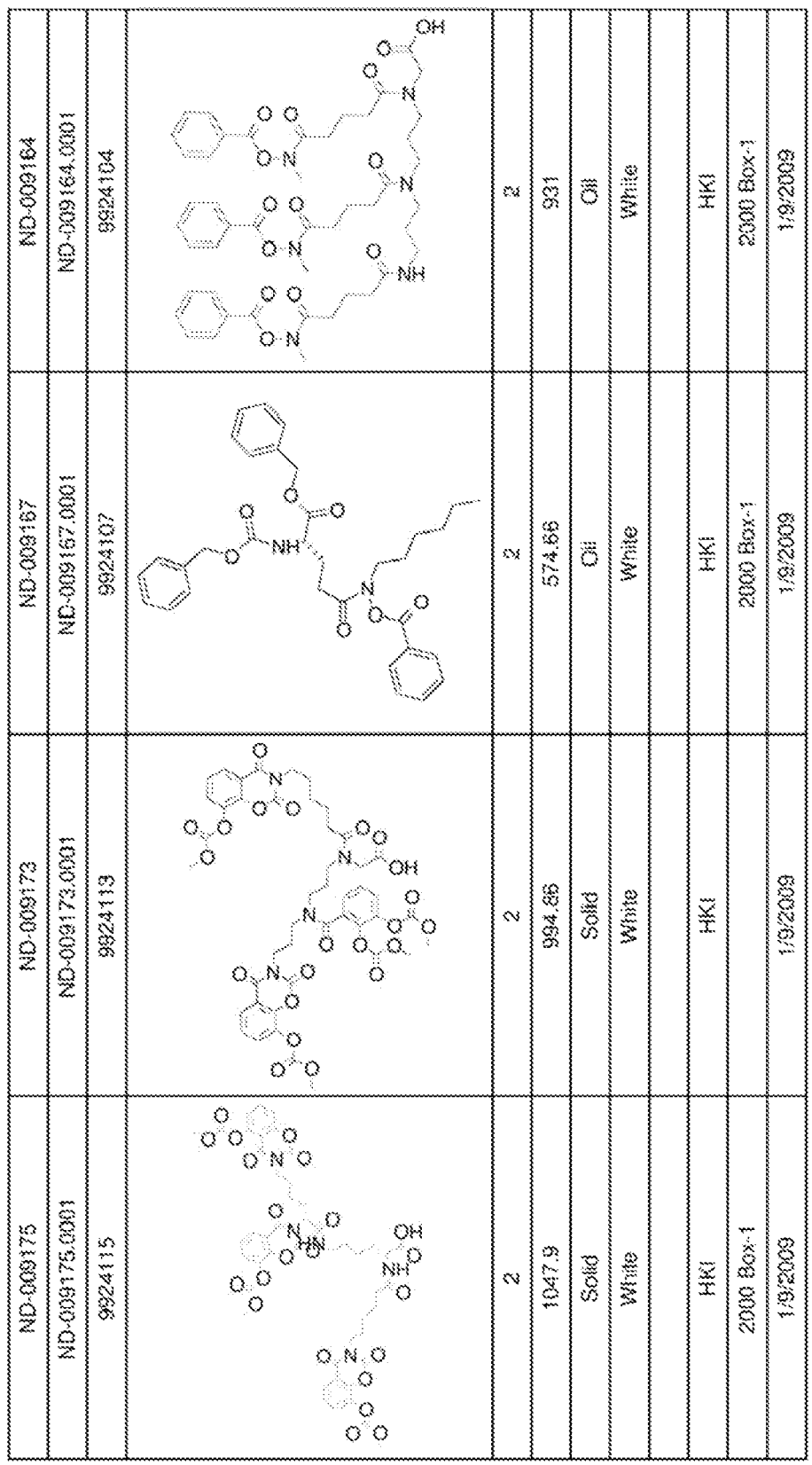

FIG. 12AAAAO
| | | | | |
|---|---|---|---|---|
| ND-009178 | ND-009193 | ND-009198 | ND-009199 | |
| ND-009178.0001 | ND-009193.0001 | ND-009198.0001 | ND-009199.0001 | |
| 9924118 | 9924124 | 9924144 | 9924145 | |
| 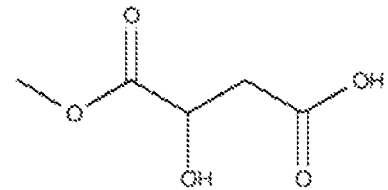 | 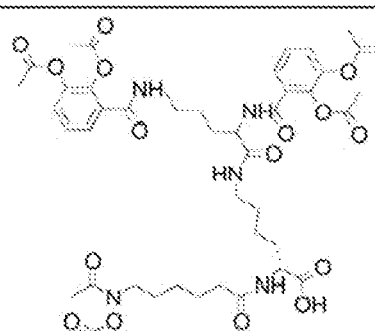 | 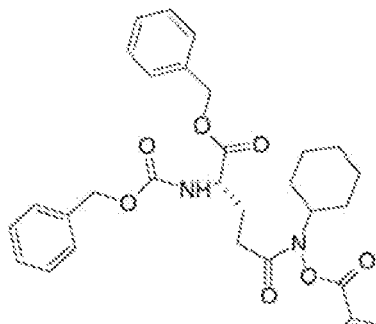 | 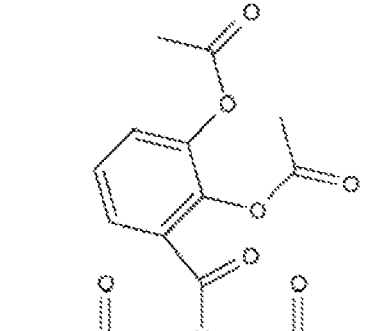 | |
| 2 | 2 | 2 | 2 | |
| 148.11 | 990.02 | 572.65 | 353.28 | |
| Oil | Solid | Oil | Solid | |
| White | White | Clear | Brown | |
| HKI | HKI | HKI | HKI | |
| 2300 Box-1 | | 2000 Box-1 | 2000 Box-1 | |
| 1/9/2009 | 1/9/2009 | 1/9/2009 | 1/9/2009 | |

FIG. 12AAAAP

| ND-008896 | ND-008893 | ND-008891 | ND-009204 |
|---|---|---|---|
| ND-008896.0001 | ND-008893.0001 | ND-008891.0001 | ND-009204.0001 |
| 9824006 | 9824003 | 9824001 | 9924150 |
| (structure) | (structure) | (structure) | (structure) |
| 2 | 2 | 2 | 2 |
| 915.92 | 659.06 | 1306.5 | 773.78 |
| Solid | Solid | Solid | Solid |
| White | Tan | White | White |
| HKI | HKI | HKI | HKI |
| Polyamine-1997-2000 | Polyamine-1997-2000 | Polyamine-1997-2000 | 2300 Box-1 |
| 1/11/2009 | 1/11/2009 | 1/11/2009 | 1/9/2009 |

FIG. 12AAAAQ

| ND-008947 | ND-008942 | ND-008919 | ND-008907 |
|---|---|---|---|
| ND-008947.0001 | ND-008942.0001 | ND-008919.0001 | ND-008907.0001 |
| 9824047 | 9824043 | 9824020 | 9824008 |
| (structure) | (structure) | (structure) | (structure) |
| 2 | 2 | 2 | 2 |
| 850.84 | 539.53 | 808.33 | 406.14 |
| Solid | Solid | Oil | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAR

| | | | |
|---|---|---|---|
| ND-008951 | ND-008950 | ND-008949 | ND-008948 |
| ND-008951.0001 | ND-008950.0001 | ND-008949.0001 | ND-008948.0001 |
| 9824052 | 9824051 | 9824050 | 9824049 |
| | | | |
| 2 | 2 | 2 | 2 |
| 919.91 | 1020 | 903.91 | 1281.3 |
| Solid | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAS

| ND-008961 | | | | | | |
|---|---|---|---|---|---|---|
| ND-008961.0001 | | | | | | |
| 9824062 | [structure] | 2 | 1261.1 | Solid | White | HKI | Polyamine-1997-2000 | 1/11/2009 |

| ND-008966 | | | | | | |
|---|---|---|---|---|---|---|
| ND-008966.0001 | | | | | | |
| 9824067 | [structure] | 2 | 656.66 | Solid | White | HKI | Polyamine-1997-2000 | 1/11/2009 |

| ND-008971 | | | | | | |
|---|---|---|---|---|---|---|
| ND-008971.0001 | | | | | | |
| 9824072 | [structure] | 2 | 807.18 | Solid | White | HKI | Polyamine-1997-2000 | 1/11/2009 |

| ND-008973 | | | | | | |
|---|---|---|---|---|---|---|
| ND-008973.0001 | | | | | | |
| 9824074 | [structure] | 2 | 1345.3 | Solid | White | HKI | Polyamine-1997-2000 | 1/11/2009 |

FIG. 12AAAAT
| ND-008987 | ND-008984 | ND-008979 | ND-008974 |
|---|---|---|---|
| ND-008987.0001 | ND-008984.0001 | ND-008979.0002 | ND-008974.0001 |
| 9824088 | 9824085 | 9824080 | 9824075 |
|  |  | 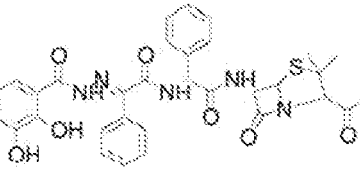 | 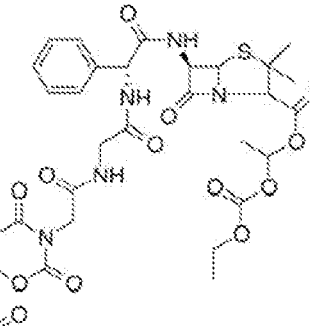 |
| 2 | 2 | 2 | 2 |
| 799.76 | 631.66 | 791.75 | 804.78 |
| Solid | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAU
| ND-008990 | ND-008990.0001 | 9824092 | 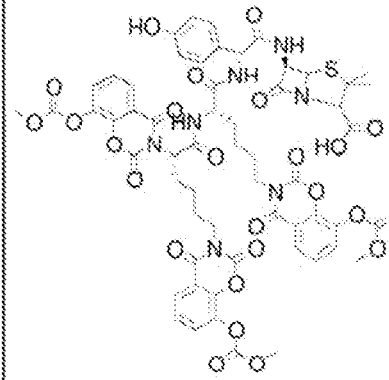 | 2 | 1282.2 | Solid | White | HKI | Polyamine-1997-2000 | 1/11/2009 |
| ND-009002 | ND-009002.0001 | 9824104 | 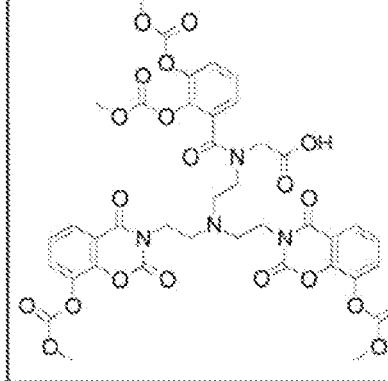 | 2 | 896.72 | Solid | White | HKI | Polyamine-1997-2000 | 1/11/2009 |
| ND-009120 | ND-009120.0001 | 9824055 | 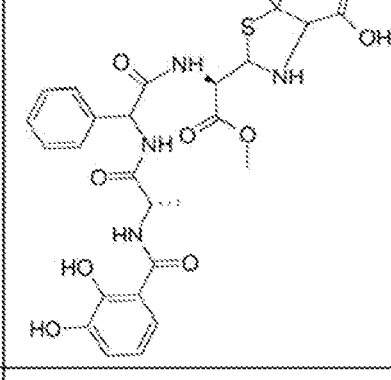 | 2 | 588.63 | Solid | White | HKI | Polyamine-1997-2000 | 1/11/2009 |
| ND-009138 | ND-009138.0001 | 9824071 | 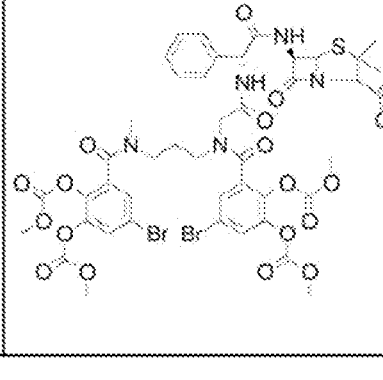 | 2 | 1139.7 | Solid | White | HKI | Polyamine-1997-2000 | 1/11/2009 |

FIG. 12AAAAV

| ND-009224 | ND-009211 | ND-009210 | ND-009209 |
|---|---|---|---|
| ND-009224.0001 | ND-009211.0001 | ND-009210.0001 | ND-009209.0001 |
| 10024023 | 9924081 | 9924080 | 9924079 |
| [structure] | [structure] | [structure] | [structure] |
| 2 | 2 | 2 | 2 |
| 806.64 | 1122 | 1364.3 | 944.93 |
| Solid | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAW
| ND-009254 | ND-009232 | ND-009231 | ND-009230 |
|---|---|---|---|
| ND-009254.0001 | ND-009232.0001 | ND-009231.0001 | ND-009230.0001 |
| 10024052 | 10024031 | 10024030 | 10024029 |
| 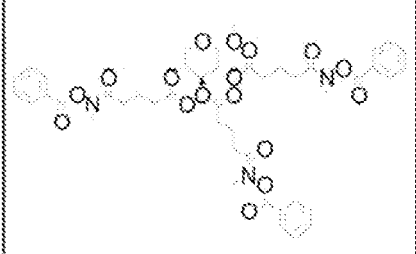 | 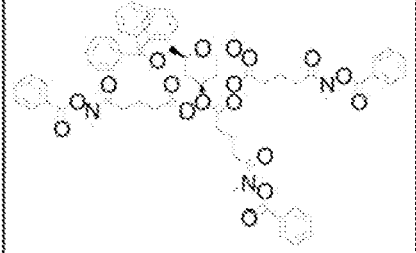 | 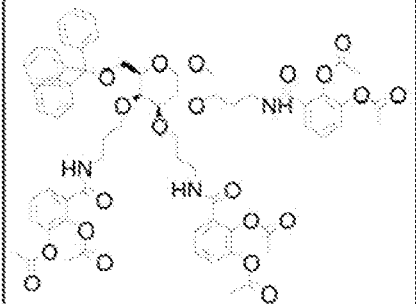 | 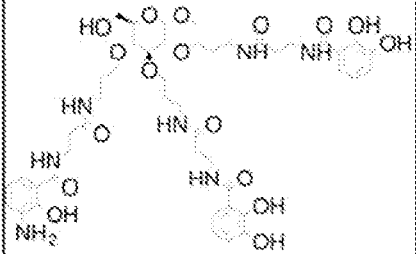 |
| 2 | 2 | 2 | 2 |
| 905.9 | 1178.2 | 1268.3 | 986.03 |
| Solid | Solid | Solid | Solid |
| White | White | White | Brown |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAX

| ND-008680 | ND-008680.0001 | 95440 | [structure] | 2 | 888.7 | Solid | Yellow | HK1 | 1996 Box | 1/11/2009 |
| --- | --- | --- | --- | --- | --- | --- | --- | --- | --- | --- |
| ND-009155 | ND-009155.0002 | 9924095 | [structure] | 2 | 954.93 | Solid | White | HK1 | 1996 Box | 1/11/2009 |
| ND-009245 | ND-009245.0001 | 10024044 | [structure] | 2 | 222.28 | Solid | White | HK1 | 1996 Box | 1/11/2009 |
| ND-008908 | ND-008908.0002 | 9824009 | [structure] | 2 | 756.78 | Solid | White | HK1 | 1998 Box-2 | 1/11/2009 |

FIG. 12AAAAY

| ND-008933 | ND-008933.0002 | 9824034 | [structure] | 2 | 804.82 | Solid | White | HK1 | 1998 Box-2 | 1/11/2009 |
| --- | --- | --- | --- | --- | --- | --- | --- | --- | --- | --- |
| ND-008934 | ND-008934.0002 | 9824035 | [structure] | 2 | 887.86 | Solid | White | HK1 | 1998 Box-2 | 1/11/2009 |
| ND-008936 | ND-008936.0002 | 9824037 | [structure] | 2 | 727.69 | Solid | White | HK1 | 1998 Box-2 | 1/11/2009 |
| ND-008940 | ND-008940.0002 | 9824041 | [structure] | 2 | 707.11 | Solid | White | HK1 | 1998 Box-2 | 1/11/2009 |

FIG. 12AAAAZ

| ND-008941 | ND-008946 | ND-009111 | ND-009111 |
|---|---|---|---|
| ND-008941.0002 | ND-008946.0002 | ND-009111.0001 | ND-009111.0002 |
| 9824042 | 9824048 | 9824046 | 9824046 |
| 2 | 2 | 2 | 2 |
| 737.53 | 933.93 | 682.67 | 682.67 |
| Solid | Solid | Solid | Solid |
| White | White | White | White |
| HKI | HKI | HKI | HKI |
| 1998 Box-2 | 1998 Box-2 | 1998 Box-2 | 1998 Box-2 |
| 1/11/2009 | 1/11/2009 | 1/11/2009 | 1/11/2009 |

FIG. 12AAAAAA

| ND-008934 | ND-008970 | ND-009129 | ND-009130 |
|---|---|---|---|
| ND-008934.0001 | ND-008970.0003 | ND-009129.0001 | ND-009130.0001 |
| 9924035 | 9924071 | 9924064 | 9924065 |
| | | | |
| 1.3 | 1.24 | 1 | 1 |
| 887.86 | 873.83 | 719.43 | 306.81 |
| Solid | Solid | Solid | Solid |
| White | White | White | White |
| HK1 | HK1 | HK1 | HK1 |
| 1998 Box-2 | 1998 Box-2 | 2000 Box-1 | 2000 Box-1 |
| 1/11/2009 | 1/11/2009 | 1/9/2009 | 1/9/2009 |

FIG. 12AAAAAB

| ND-009133 | ND-009135 | ND-009181 | ND-009183 |
|---|---|---|---|
| ND-009133.0001 | ND-009135.0001 | ND-009181.0001 | ND-009183.0001 |
| 9924066 | 9924068 | 9924074 | 9924076 |
| | | | |
| 1 | 1 | 1 | 1 |
| 1050.8 | 1003.9 | 1358.4 | 1439.3 |
| Solid | Solid | Solid | Solid |
| White | White | White | White |
| HKI | HKI | HKI | HKI |
| 2300 Box-1 | 2300 Box-1 | 2300 Box-1 | 2300 Box-1 |
| 1/9/2009 | 1/9/2009 | 1/9/2009 | 1/9/2009 |

FIG. 12AAAAAC
| ND-009145 | ND-009143 | ND-009208 | ND-009206 |
|---|---|---|---|
| ND-009145.0001 | ND-009143.0001 | ND-009208.0001 | ND-009206.0001 |
| 9924087 | 9924085 | 9924078 | 9924077 |
| 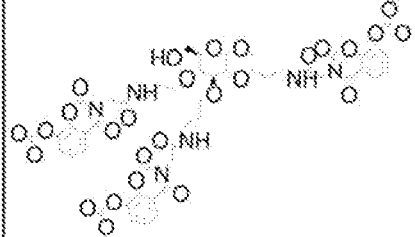 | 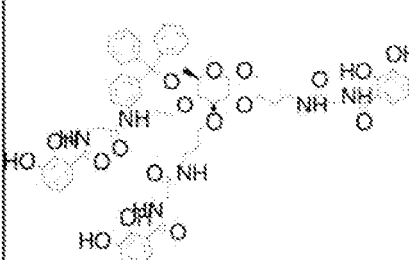 | 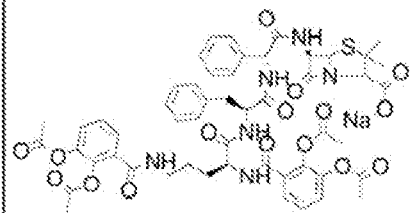 | 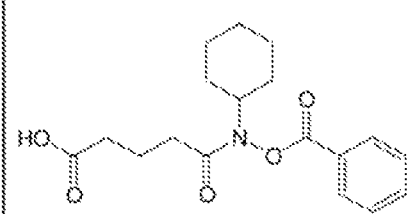 |
| 1 | 1 | 1 | 1 |
| 333.38 | 1073.1 | 1187.2 | 1197 |
| Solid | Solid | Solid | Solid |
| White | White | White | White |
| HKI | HKI | HKI | HKI |
| 2000 Box-1 | 2000 Box-1 | | 2000 Box-1 |
| 1/9/2009 | 1/9/2009 | 1/9/2009 | 1/9/2009 |

FIG. 12AAAAAD

| ND-009147 | ND-009152 | ND-009158 | ND-009159 |
|---|---|---|---|
| ND-009147.0001 | ND-009152.0001 | ND-009158.0001 | ND-009159.0001 |
| 9924089 | 9924092 | 9924098 | 9924099 |
| (structure) | (structure) | (structure) | (structure) |
| 1 | 1 | 1 | 1 |
| 916.92 | 1016.1 | 640.68 | 586.54 |
| Solid | Solid | Oil | Oil |
| White | White | White | White |
| HKI | HKI | HKI | HKI |
| 2000 Box-1 | 2000 Box-1 | 2000 Box-1 | 2000 Box-1 |
| 1/9/2009 | 1/9/2009 | 1/9/2009 | 1/9/2009 |

FIG. 12AAAAAE
| ND-009170 | ND-009168 | ND-009162 | ND-009160 |
|---|---|---|---|
| ND-009170.0001 | ND-009168.0001 | ND-009162.0001 | ND-009160.0001 |
| 9924110 | 9924108 | 9924102 | 9924100 |
| 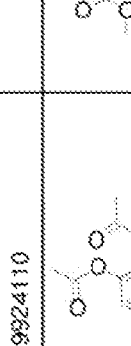 | 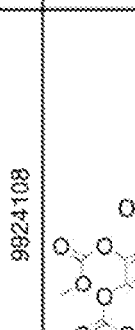 | 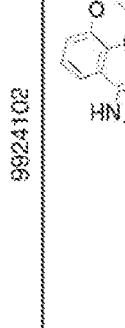 | 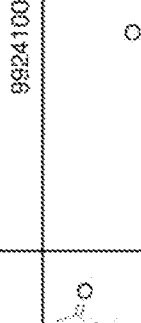 |
| 1 | 1 | 1 | 1 |
| 917.93 | 1072.8 | 1021.9 | 1048.1 |
| Solid | Solid | Oil | Solid |
| White | White | White | Clear |
| HK1 | HK1 | HK1 | HK1 |
| 2000 Box-1 | 2000 Box-1 | 2000 Box-1 | 2000 Box-1 |
| 1/9/2009 | 1/9/2009 | 1/9/2009 | 1/9/2009 |

FIG. 12AAAAAF

| ND-009179 | | 1 | 339.08 | Solid | Tan | HK1 | 2300 Box-1 | 1/9/2009 |
|---|---|---|---|---|---|---|---|---|
| ND-009179.0001 | | | | | | | | |
| 9924119 | | | | | | | | |

| ND-009180 | | 1 | 788.32 | Solid | White | HK1 | 2300 Box-1 | 1/9/2009 |
|---|---|---|---|---|---|---|---|---|
| ND-009180.0001 | | | | | | | | |
| 9924120 | | | | | | | | |

| ND-009195 | | 1 | 1262.4 | Solid | White | HK1 | 2300 Box-1 | 1/9/2009 |
|---|---|---|---|---|---|---|---|---|
| ND-009195.0001 | | | | | | | | |
| 9924141 | | | | | | | | |

| ND-009196 | | 1 | 1326.2 | Solid | White | HK1 | 2300 Box-1 | 1/9/2009 |
|---|---|---|---|---|---|---|---|---|
| ND-009196.0001 | | | | | | | | |
| 9924142 | | | | | | | | |

FIG. 12AAAAAG
| ND-008922 | ND-008895 | ND-008273 | ND-009205 |
|---|---|---|---|
| ND-008922.0001 | ND-008895.0001 | ND-008273.0001 | ND-009205.0001 |
| 9824023 | 9824005 | 10024068 | 9924151 |
|  |  | 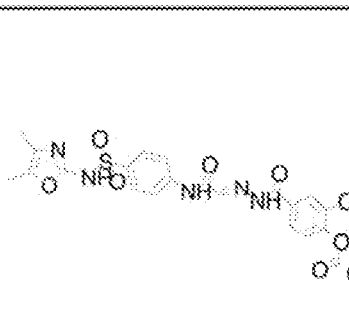 | 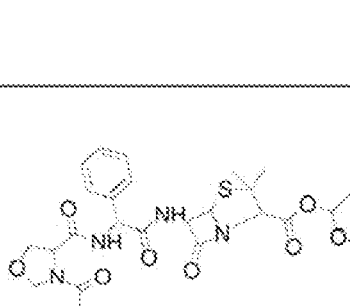 |
| 1 | 1 | 1 | 1 |
| 816.79 | 589.53 | 558.49 | 1229.3 |
| Solid | Solid | Solid | Solid |
| White | White | White | White |
| HKI | HKI | HKI | HKI |
| Polyamine-1997-2000 | Polyamine-1997-2000 | Yellow-1994-2000 | 2300 Box-1 |
| 1/11/2009 | 1/11/2009 | 1/11/2009 | 1/9/2009 |

FIG. 12AAAAAH
| ND-008962 | ND-008959 | ND-008958 | ND-008923 |
|---|---|---|---|
| ND-008962.0001 | ND-008959.0001 | ND-008958.0001 | ND-008923.0001 |
| 9824063 | 9824060 | 9824059 | 9824024 |
| 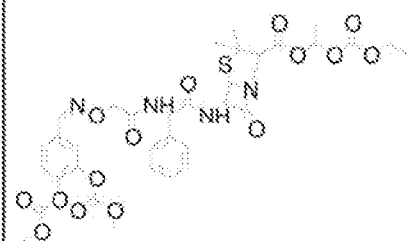 | 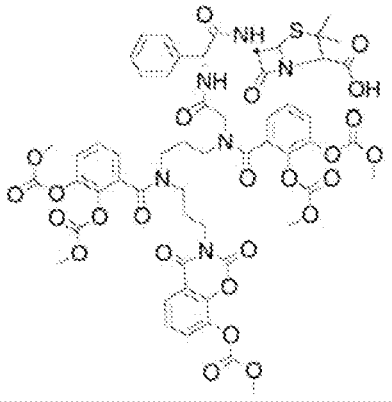 |  |  |
| 1 | 1 | 1 | 1 |
| 1329.3 | 1381.5 | 1245.1 | 774.75 |
| Solid | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAAI
| ND-008980 | ND-008977 | ND-008967 | ND-008964 |
|---|---|---|---|
| ND-008980.0001 | ND-008977.0001 | ND-008967.0001 | ND-008964.0001 |
| 9824081 | 9824078 | 9824068 | 9824065 |
| 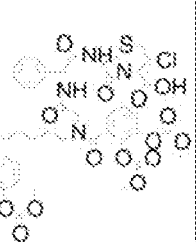 |  |  |  |
| 1 | 1 | 1 | 1 |
| 614.6 | 753.53 | 853.64 | 1347.7 |
| Oil | Solid | Solid | Solid |
| White | White | White | White |
| HKI | HKI | HKI | HKI |
| Polyamine-1997-2000 | Polyamine-1997-2000 | Polyamine-1997-2000 | Polyamine-1997-2000 |
| 1/11/2009 | 1/11/2009 | 1/11/2009 | 1/11/2009 |

FIG. 12AAAAAJ
| ND-008913 | ND-009226 | ND-009001 | ND-008985 |
|---|---|---|---|
| ND-008913.0002 | ND-009226.0002 | ND-009001.0001 | ND-008985.0001 |
| 9824014 | 10024025 | 9824105 | 9824086 |
| 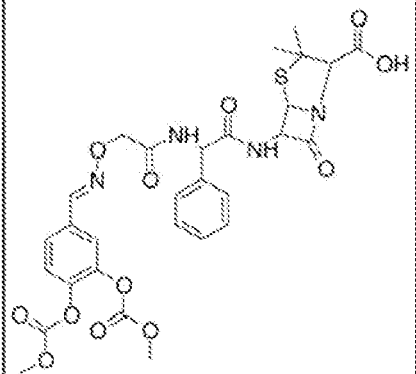 | 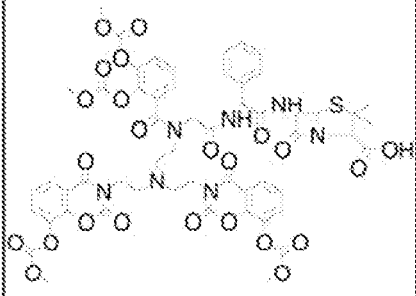 | 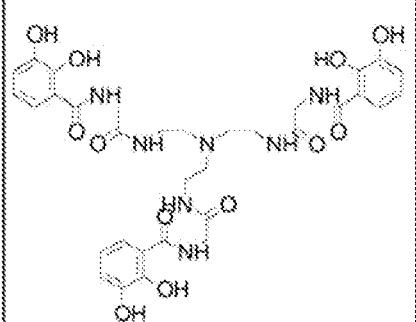 | 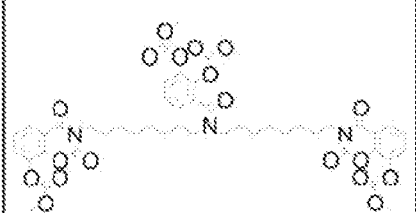 |
| 1 | 1 | 1 | 1 |
| 963.93 | 725.7 | 1228.1 | 658.63 |
| Solid | Solid | Solid | Solid |
| White | White | White | White |
| HKI | HKI | HKI | HKI |
| 1986 Box | Polyamine-1997-2000 | Polyamine-1997-2000 | Polyamine-1997-2000 |
| 1/11/2009 | 1/11/2009 | 1/11/2009 | 1/11/2009 |

FIG. 12AAAAAK

| | | | | | | | | |
|---|---|---|---|---|---|---|---|---|
| ND-008929 | ND-008929.0001 | 9824030 | (structure) | 1 | 623.69 | Solid | White | HK1 | 1996 Box | 1/11/2009 |
| ND-008986 | ND-008986.0002 | 9824037 | (structure) | 1 | 864.8 | Solid | White | HK1 | 1996 Box | 1/11/2009 |
| ND-008986 | ND-008986.0003 | 9824037 | (structure) | 1 | 864.8 | Solid | White | HK1 | 1996 Box | 1/11/2009 |
| ND-009000 | ND-009000.0001 | 9824090 | (structure) | 1 | 1054 | Solid | White | HK1 | 1996 Box | 1/11/2009 |

FIG. 12AAAAAL
| ND-009140 | ND-009140.0001 | 9924082 | 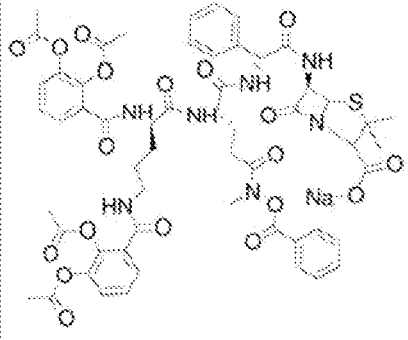 | 1 | 1188.1 | Solid | White | HKI | 1996 Box | 1/11/2009 |
|---|---|---|---|---|---|---|---|---|---|---|
| ND-009184 | ND-009184.0001 | 9924125 | 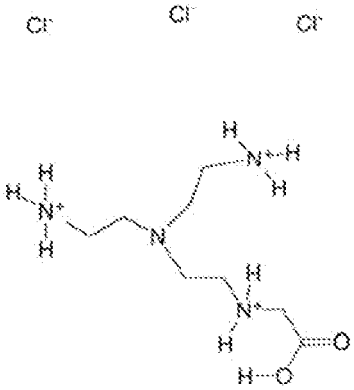 | 1 | 313.65 | Solid | White | HKI | 1996 Box | 1/11/2009 |
| ND-009191 | ND-009191.0002 | 9924132 | 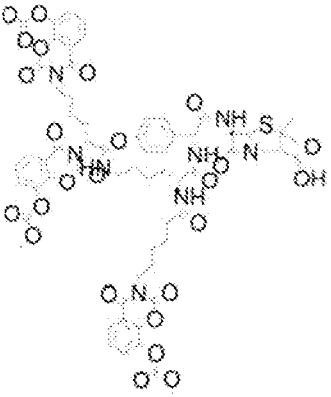 | 1 | 1379.3 | Solid | White | HKI | 1996 Box | 1/11/2009 |
| ND-009196 | ND-009196.0002 | 9924142 | 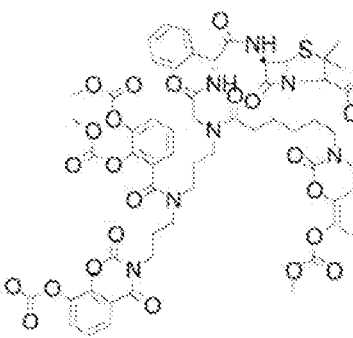 | 1 | 1326.2 | Oil | White | HKI | 1996 Box | 1/11/2009 |

FIG. 12AAAAAM
| ND-008810 | ND-008840 | ND-009067 | ND-009069 |
|---|---|---|---|
| ND-008810.0001 | ND-008840.0001 | ND-009067.0002 | ND-009069.0001 |
| 9924066 | 9924090 | 9924001 | 9924003 |
| 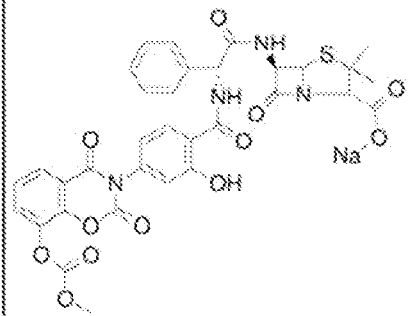 | 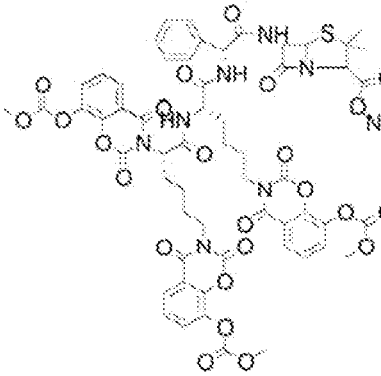 | 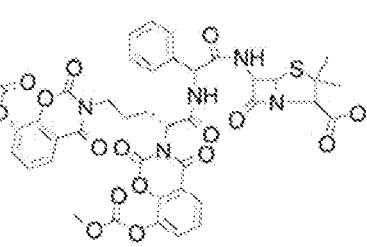 | 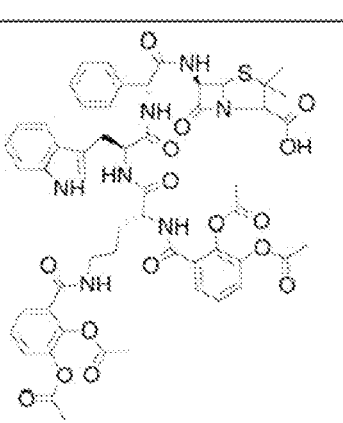 |
| 1 | 1 | 1 | 1 |
| 726.64 | 1289.1 | 903.82 | 1090.1 |
| Solid | Solid | Solid | Solid |
| White | White | White | White |
| HK1 | HK1 | HK1 | HK1 |
| 1997 Box-1 | 1997 Box-1 | 1998 Box-2 | 1998 Box-2 |
| 1/11/2009 | 1/11/2009 | 1/11/2009 | 1/11/2009 |

FIG. 12AAAAAN
| | | | | | | | |
|---|---|---|---|---|---|---|---|
| ND-009070 | ND-009070.0001 | 9924004 | 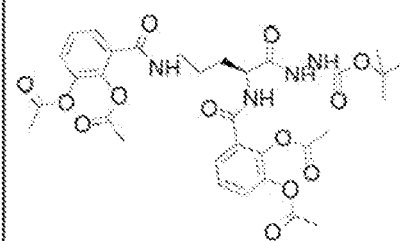 | 1 | 686.66 | Solid White | HK1 | 1998 Box-2 | 1/11/2009 |
| ND-009071 | ND-009071.0001 | 9924005 | 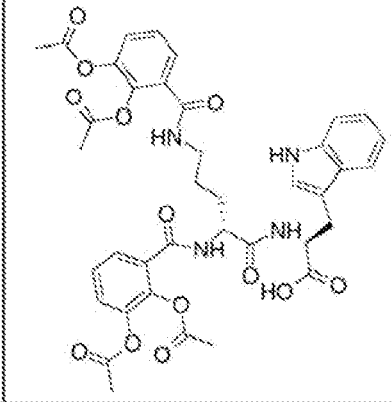 | 1 | 758.73 | Solid White | HK1 | 1998 Box-2 | 1/11/2009 |
| ND-009072 | ND-009072.0001 | 9924006 | 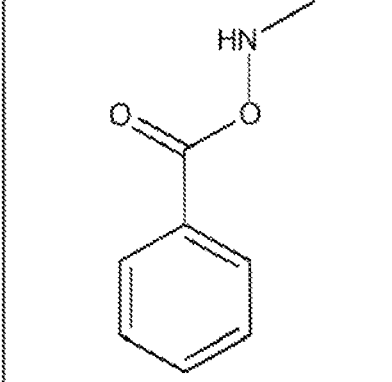 | 1 | 151.16 | Solid White | HK1 | 1998 Box-2 | 1/11/2009 |
| ND-009074 | ND-009074.0001 | 9924008 |  | 1 | 132.16 | Oil Yellow | HK1 | 1998 Box-2 | 1/11/2009 |

FIG. 12AAAAAO
| | | | | | | | | | |
|---|---|---|---|---|---|---|---|---|---|
| ND-009075 | ND-009075.0001 | 9924009 | 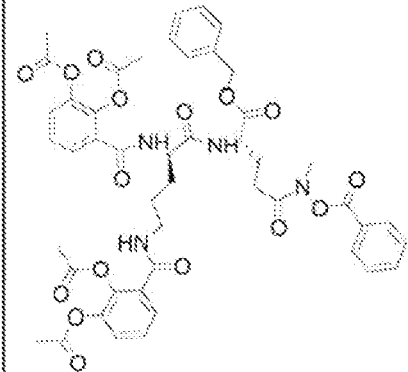 | 1 | 924.9 | Solid | White | HKI | 1998 Box-2 | 1/11/2009 |
| ND-009076 | ND-009076.0001 | 9924010 | 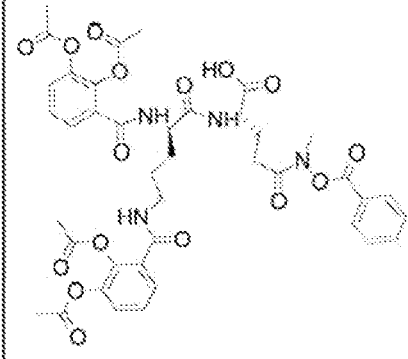 | 1 | 834.78 | Solid | Yellow | HKI | 1998 Box-2 | 1/11/2009 |
| ND-009077 | ND-009077.0001 | 9924011 | 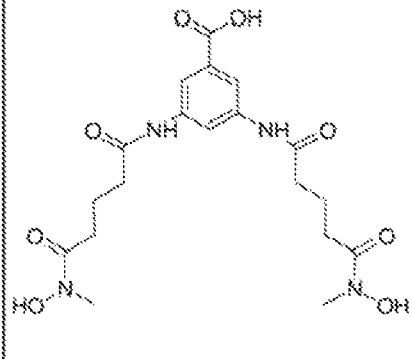 | 1 | 438.43 | Solid | Tan | HKI | 1998 Box-2 | 1/11/2009 |
| ND-009078 | ND-009078.0001 | 9924012 | 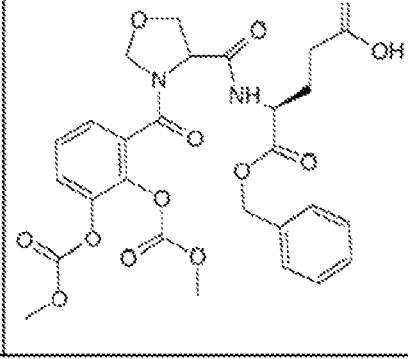 | 1 | 588.52 | Solid | White | HKI | 1998 Box-2 | 1/11/2009 |

FIG. 12AAAAAP

| | | | | | | | |
|---|---|---|---|---|---|---|---|
| ND-009079 | ND-009079.0001 | 9924013 | | 1 | 758.73 | Solid | White | HK1 | 1998 Box-2 | 1/11/2009 |
| ND-009080 | ND-009080.0002 | 9924014 | | 1 | 749.72 | Solid | White | HK1 | 1998 Box-2 | 1/11/2009 |
| ND-009081 | ND-009081.0001 | 9924015 | | 1 | 646.64 | Solid | White | HK1 | 1998 Box-2 | 1/11/2009 |
| ND-009082 | ND-009082.0001 | 9924016 | | 1 | 721.66 | Solid | White | HK1 | 1998 Box-2 | 1/11/2009 |

FIG. 12AAAAAQ

| ND-009083 | | | | | | | |
|---|---|---|---|---|---|---|---|
| ND-009083.0001 | | | | | | | |
| 9924017 | [structure] | 1 | 631.54 | Oil | Tan | HKI | 1998 Box-2 | 1/11/2009 |

| ND-009086 | | | | | | | |
|---|---|---|---|---|---|---|---|
| ND-009086.0001 | | | | | | | |
| 9924020 | [structure] | 1 | 794.67 | Solid | White | HKI | 1998 Box-2 | 1/11/2009 |

| ND-009087 | | | | | | | |
|---|---|---|---|---|---|---|---|
| ND-009087.0001 | | | | | | | |
| 9924021 | [structure] | 1 | 560.64 | Oil | Tan | HKI | 1998 Box-2 | 1/11/2009 |

| ND-009088 | | | | | | | |
|---|---|---|---|---|---|---|---|
| ND-009088.0001 | | | | | | | |
| 9924022 | [structure] | 1 | 478.5 | Solid | White | HKI | 1998 Box-2 | 1/11/2009 |

FIG. 12AAAAAR

| | | | | | | |
|---|---|---|---|---|---|---|
| ND-009089 | ND-009089.0001 | 9924023 | [structure] | 1 | 388.37 | Solid | White | HK1 | 1998 Box-2 | 1/11/2009 |
| ND-009090 | ND-009090.0001 | 9924024 | [structure] | 1 | 676.67 | Solid | White | HK1 | 1998 Box-2 | 1/11/2009 |
| ND-009091 | ND-009091.0001 | 9924025 | [structure] | 1 | 934.89 | Solid | White | HK1 | 1998 Box-2 | 1/11/2009 |
| ND-009092 | ND-009092.0001 | 9924026 | [structure] | 1 | 805.78 | Oil | White | HK1 | 1998 Box-2 | 1/11/2009 |

FIG. 12AAAAAS

| ND-009097 | | | | | | |
|---|---|---|---|---|---|---|
| ND-009097.0001 | | | | | | |
| 9924032 | [structure] | 1 | 1180.2 | Solid | White | HK1 | 1998 Box-2 | 1/11/2009 |

| ND-009098 | | | | | | |
|---|---|---|---|---|---|---|
| ND-009098.0001 | | | | | | |
| 9924033 | [structure] | 1 | 934.89 | Solid | White | HK1 | 1998 Box-2 | 1/11/2009 |

| ND-009099 | | | | | | |
|---|---|---|---|---|---|---|
| ND-009099.0001 | | | | | | |
| 9924035 | [structure] | 1 | 1283.3 | Solid | White | HK1 | 1998 Box-2 | 1/11/2009 |

| ND-009100 | | | | | | |
|---|---|---|---|---|---|---|
| ND-009100.0001 | | | | | | |
| 9924036 | [structure] | 1 | 1304.3 | Solid | White | HK1 | 1998 Box-2 | 1/11/2009 |

FIG. 12AAAAAT
| ND-009101 | ND-009103 | ND-009104 | ND-009107 |
|---|---|---|---|
| ND-009101.0001 | ND-009103.0001 | ND-009104.0001 | ND-009107.0001 |
| 9924037 | 9924039 | 9924040 | 9924042 |
| 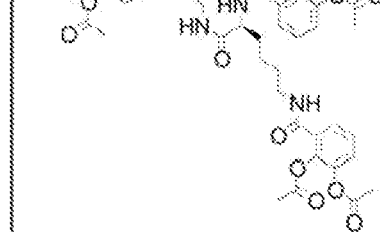 | 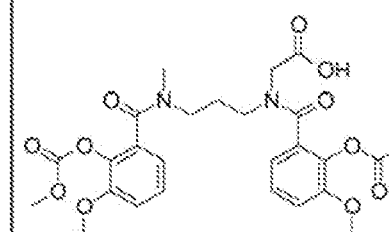 | 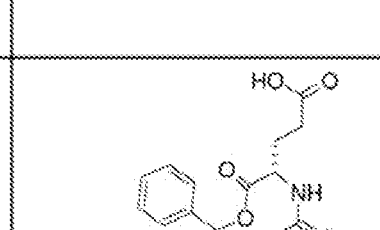 | 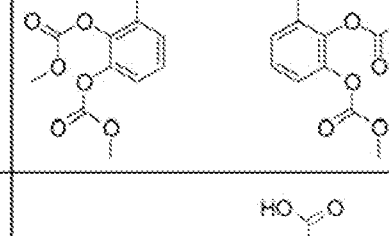 |
| 1 | 1 | 1 | 1 |
| 1288.3 | 650.54 | 869.78 | 837.74 |
| Solid | Solid | Solid | Solid |
| White | White | White | White |
| HK1 | HK1 | HK1 | HK1 |
| 1998 Box-2 | 1998 Box-2 | 1998 Box-2 | 1998 Box-2 |
| 1/11/2009 | 1/11/2009 | 1/11/2009 | 1/11/2009 |

FIG. 12AAAAAU

| ND-009108 | ND-009109 | ND-009110 | ND-009112 |
|---|---|---|---|
| ND-009108.0001 | ND-009109.0001 | ND-009110.0001 | ND-009112.0001 |
| 9924043 | 9924044 | 9924045 | 9924047 |
| | | | |
| 1 | 1 | 1 | 1 |
| 961.93 | 949.89 | 254.73 | 989.03 |
| Solid | Solid | Solid | Oil |
| White | White | White | Clear |
| HK1 | HK1 | HK1 | HK1 |
| 1998 Box-2 | 1998 Box-2 | 1998 Box-2 | 1998 Box-2 |
| 1/11/2009 | 1/11/2009 | 1/11/2009 | 1/11/2009 |

FIG. 12AAAAAV

| ND-009113 | ND-009113.0001 | 9924048 | [structure] | 1 | 682.67 | Solid | White | HK1 | 1998 Box-2 | 1/11/2009 |
| --- | --- | --- | --- | --- | --- | --- | --- | --- | --- | --- |
| ND-009115 | ND-009115.0001 | 9924050 | [structure] | 1 | 424.36 | Solid | Brown | HK1 | 1998 Box-2 | 1/11/2009 |
| ND-009117 | ND-009117.0001 | 9924052 | [structure] | 1 | 1051.1 | Solid | White | HK1 | 1998 Box-2 | 1/11/2009 |
| ND-009118 | ND-009118.0001 | 9924053 | [structure] | 1 | 1123.1 | Solid | White | HK1 | 1998 Box-2 | 1/11/2009 |

FIG. 12AAAAAW
| ND-009124 | ND-009123 | ND-009122 | ND-009119 |
|---|---|---|---|
| ND-009124.0001 | ND-009123.0001 | ND-009122.0001 | ND-009119.0001 |
| 9924059 | 9924058 | 9924057 | 9924054 |
| 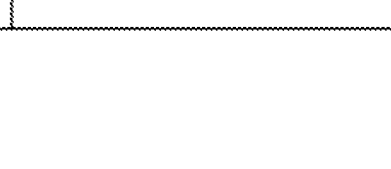 | 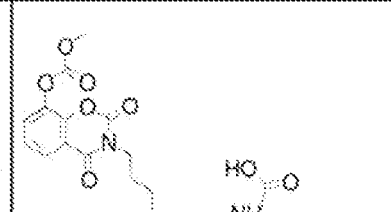 | 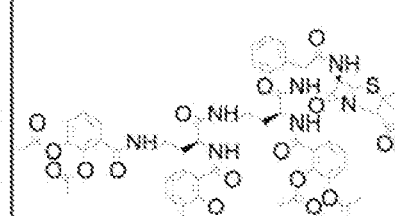 | 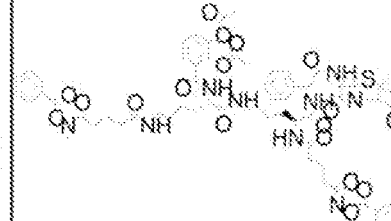 |
| 1 | 1 | 1 | 1 |
| 880.76 | 912.8 | 1238.2 | 1320.4 |
| Solid | Oil | Solid | Solid |
| White | Clear | White | White |
| HKI | HKI | HKI | HKI |
| 1998 Box-2 | 1998 Box-2 | 1998 Box-2 | 1998 Box-2 |
| 1/11/2009 | 1/11/2009 | 1/11/2009 | 1/11/2009 |

FIG. 12AAAAAX

| ND-009125 | ND-009125.0001 | 9924060 | [structure] | 1 | 961.96 | Oil | Clear | HK1 | 1998 Box-2 | 1/11/2009 |
| ND-009127 | ND-009127.0001 | 9924062 | [structure] | 1 | 309.27 | Solid | White | HK1 | 1998 Box-2 | 1/11/2009 |
| ND-009128 | ND-009128.0001 | 9924063 | [structure] | 1 | 1293.4 | Solid | White | HK1 | 1998 Box-2 | 1/11/2009 |
| ND-009136 | ND-009136.0001 | 9924069 | [structure] | 1 | 1083.7 | Solid | White | HK1 | 1998 Box-2 | 1/11/2009 |

FIG. 12AAAAAY

| ND-009114 | ND-009185 | ND-009067 | ND-009270 |
|---|---|---|---|
| ND-009114.0001 | ND-009185.0003 | ND-009067.0001 | ND-009270.0003 |
| 9924049 | 9924126 | 9924001 | 10024067 |
| (structure) | (structure) | (structure) | (structure) |
| 0.5 | 0.66 | 0.78 | 0.79 |
| 906.84 | 710.69 | 903.82 | 889.88 |
| Solid | Solid | Solid | Solid |
| White | White | White | White |
| HK1 | HK1 | HK1 | HK1 |
| 1998 Box-2 | 1998 Box | 1998 Box-2 | 1998 Box-2 |
| 1/11/2009 | 1/11/2009 | 1/11/2009 | 1/11/2009 |

FIG. 12AAAAAZ
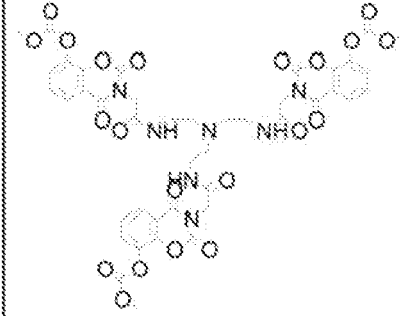

FIG. 12AAAAAAA
| Compound | Cpd Type | Structure | PaO1 | Pa KW799/wt | Pa KW799/61 |
|---|---|---|---|---|---|
| loracarbef | | | | >200μM | 50μM |
| Ampicillin | | | >200μM | >200μM | .39μM |
| cefaclor | | | >50μM | >50μM | >50μM |
| MG-112 | | 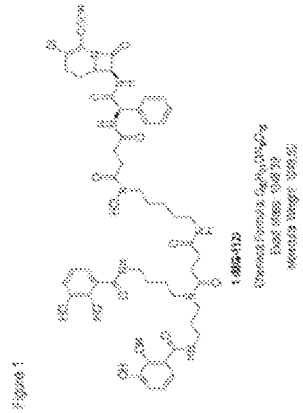 | >70μM | 70μM | .2μM |
| MG-115 | | 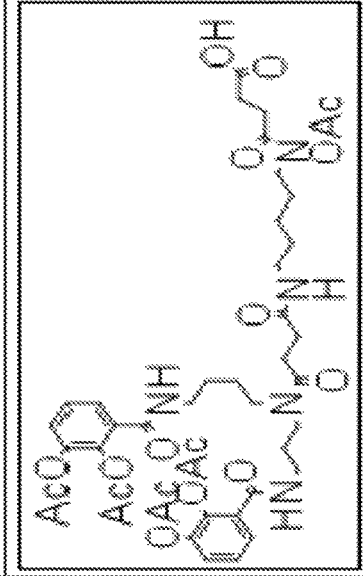 | | >200μM | >200μM |

FIG. 12AAAAAAB
| Compound | Cpd Type | Structure | PaO1 | Pa KW799/wt | Pa KW799/61 |
|---|---|---|---|---|---|
| MG-117a | | 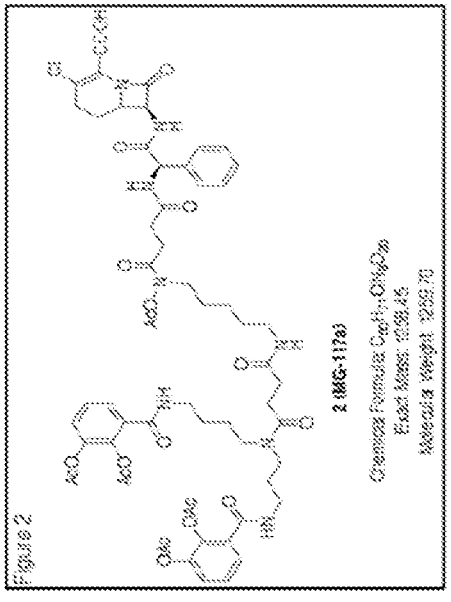 | >70µM | 70µM | .08µM |
| MG-121 (impure) | | 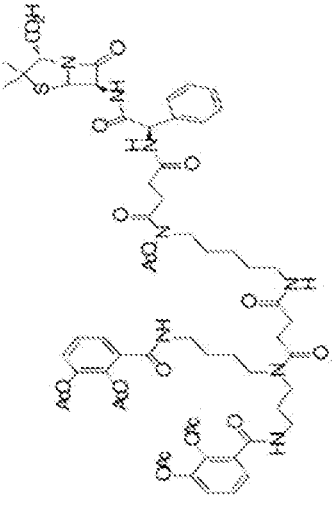 | <12.5µM & > 0.39µM- .55µM | 0.14µM- 0.2µM | .025µM |

FIG. 12AAAAAAC
| Compound | Cpd Type | Structure | PaO1 | Pa KW799/wt | Pa KW799/61 |
|---|---|---|---|---|---|
| MG-127 | | 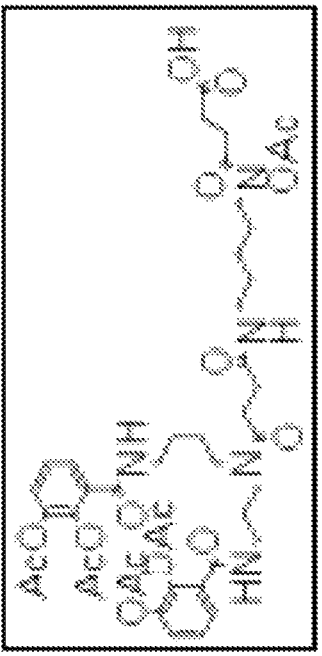 | | >200μM | >200μM |
| MG-185 | | 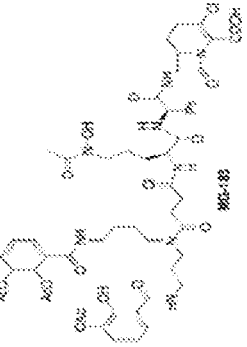 | >50μM | >50μM ??? 1.56M??? | 0.2μM |
| MG-186 | | 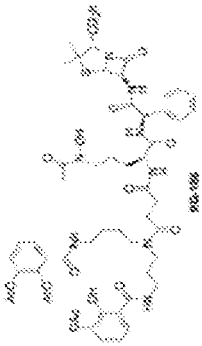 | <25μM and >0.2 0.4μM | <50μM & >0.1μM | 0.05μM |

FIG. 12AAAAAAD

| Compound | Cpd Type | Structure | PaO1 | Pa KW799/wt | Pa KW799/61 |
|---|---|---|---|---|---|
| MG-188 | | MG-188 (MG-172q) | >50μM | >50μM | 0.39μM |
| MG-189 | | MG-189 (MG-112) | >50μM | >50μM | 0.1μM |

FIG. 12AAAAAE

| Compound | Cpd Type | Structure | Pa01 | Pa KW799/wt | Pa KW799/61 |
|---|---|---|---|---|---|
| MG-216A | free acid | 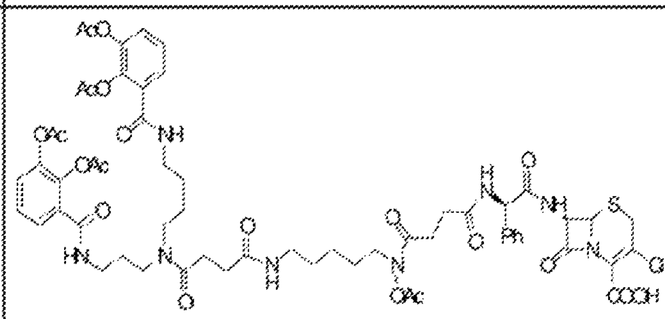 | >50μM | 0.39μM | |
| MG-216B | | 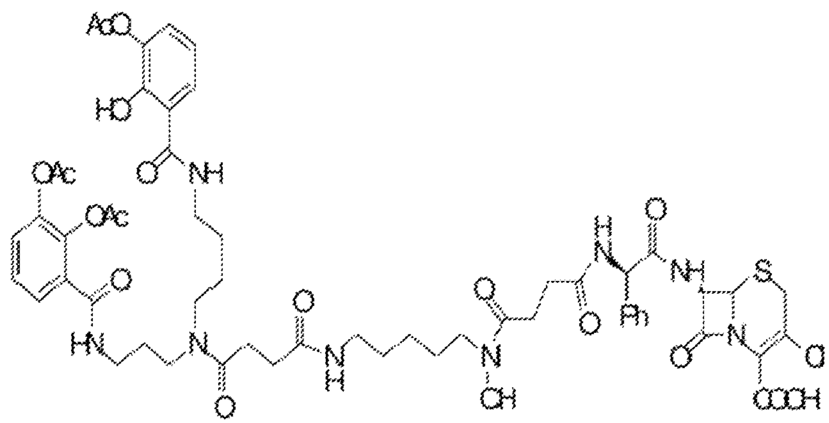 | >50μM | 0.39μM | |

FIG. 12AAAAAAF

| Compound | Cpd Type | Structure | Pa01 | Pa KW799/wt | Pa KW799/61 |
|---|---|---|---|---|---|
| MG-227 | free acid | 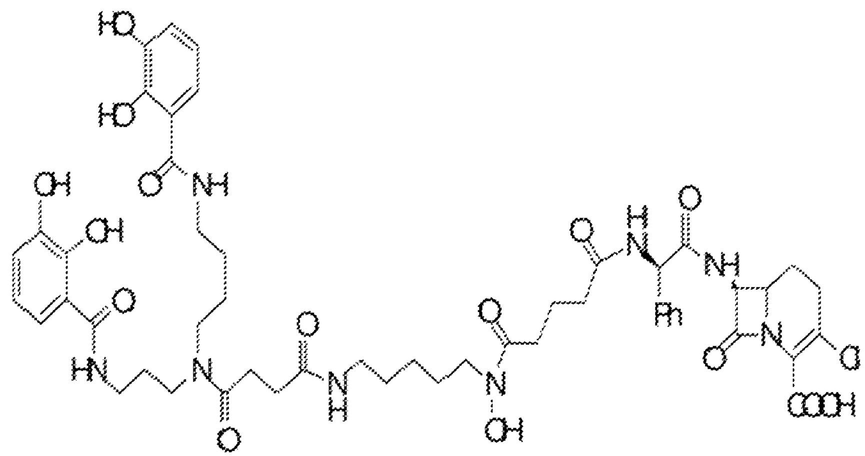 | >50µM | 0.2µM | |
| MG-228 | | 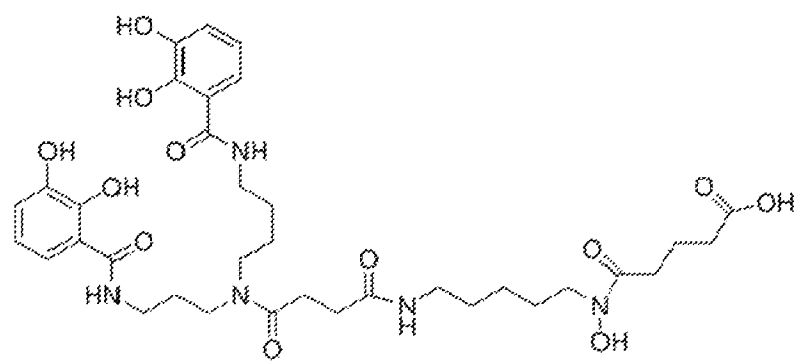 | | | |

FIG. 12AAAAAAG
| Compound | Cpd Type | Structure | PaO1 | Pa KW799/wt | Pa KW799/61 |
|---|---|---|---|---|---|
| MG-233B | Na salt | 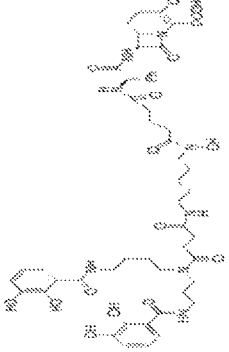 | >50µM | >50µM | |
| MG-237B | Na salt of MG-227 | 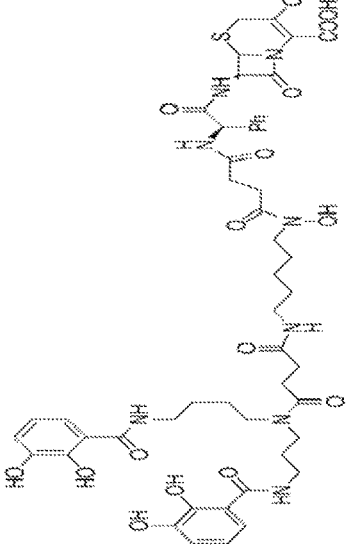 | >50µM | >50µM | |
| MG-121 (pure) | | | 0.2µM | .05µM | |

FIG. 12AAAAAAH

| Compound | Cpd Type | Structure | PaO1 | Pa KW799/wt | Pa KW799/61 |
|---|---|---|---|---|---|
| MG-1-251 MG-2-13 MG-2-18 | mixed ligand glutaryl ampicillin conjugate | MG-1-251, MG-2-13, MG-2-18<br>Chemical Formula: $C_{51}H_{66}N_8O_{15}S$<br>Exact Mass: 1062.44 | | | |

FIG. 12AAAAAAI

| Compound | Cpd Type | Structure | PaO1 | Pa KW799/wt | Pa KW799/61 |
|---|---|---|---|---|---|
| MG-255 | | 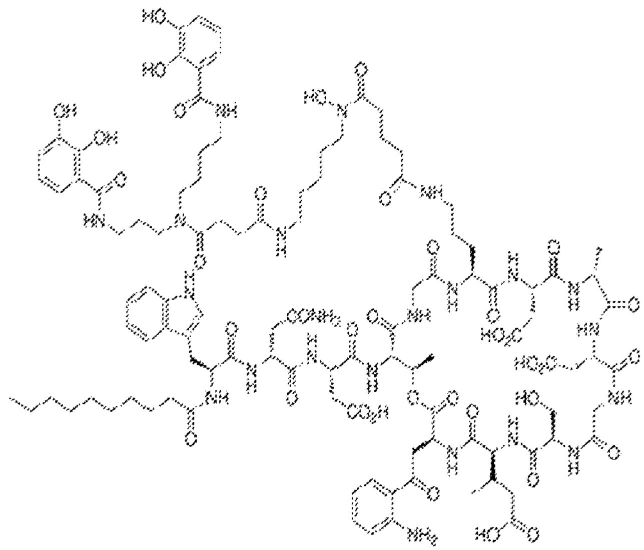 | | >100µM | |
| MG-281 (MG-189-iotB) | | | | | |

FIG. 12AAAAAAJ
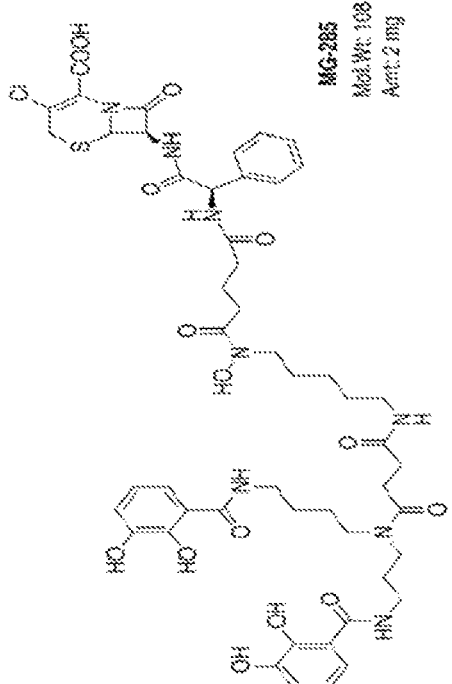

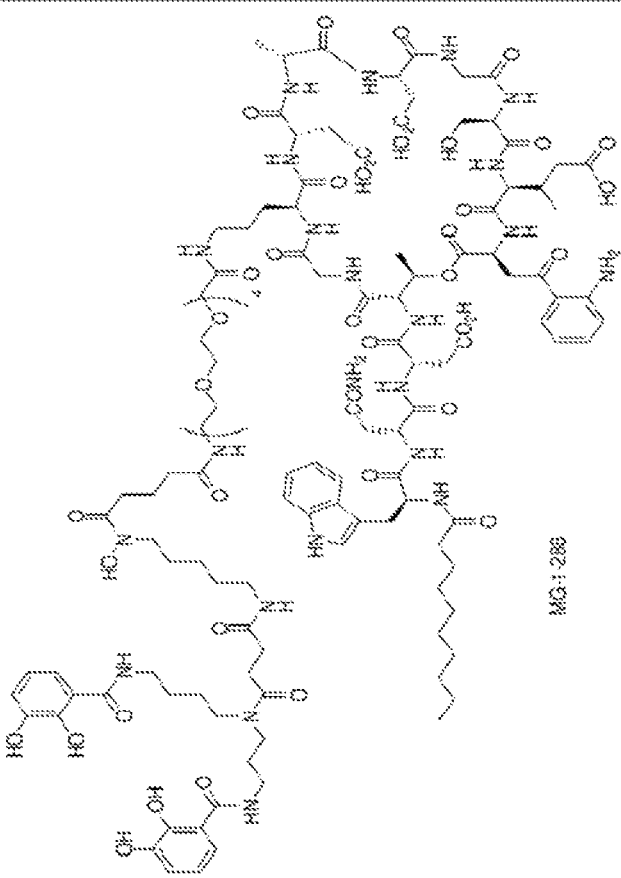
FIG. 12AAAAAAK

FIG. 12AAAAAAL

| Compound | Cpd Type | Structure | PaO1 | Pa KW799/wt | Pa KW799/61 |
|---|---|---|---|---|---|
| MG-1-294 | | MG-1-294 | | | |
| MG-2-27 | mixed ligand glutaryl cefaclor conjugate | MG-2-27 Chemical Formula: C₅₀H₆₀ClN₉Na₃O₁₅S Exact Mass: 1102.35 | | | |

FIG. 12AAAAAAM

| Compound | Cpd Type | Structure | PaO1 | Pa KW799/wt | Pa KW799/61 |
|---|---|---|---|---|---|
| MG-1-299 MG-2-27a | mixed ligand glutaryl cefaclor conjugate | Chemical Formula: C50H61ClN8O15S<br>Exact Mass: 1080.37 | | | |
| Sulbactam | | | | | |

FIG. 12AAAAAAN

| Compound | Cpd Type | Structure | PaO1 | Pa KW799/wt. |
|---|---|---|---|---|
| YML-I-18 | Acetylated BisCatechol-Ampicillin | 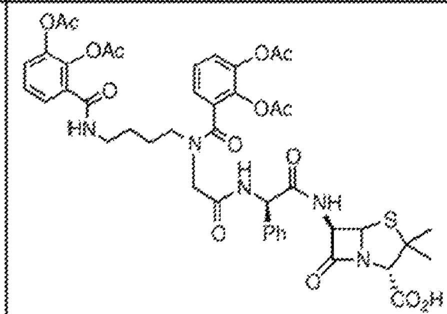 | .004μM .0156μM | 0.0313μM 0.0156μM .0156μM |
| YML-I-18cr | Acetylated BisCatechol-Ampicillin | 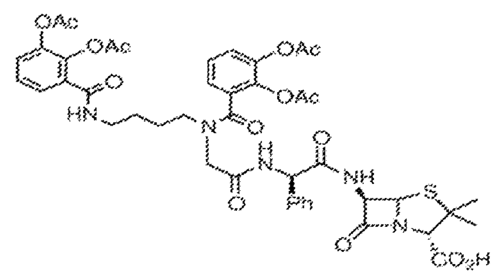 | | |
| YML-I-27 | Boc5 AminoHydroxyl aminoSuccinate Ampicillin | 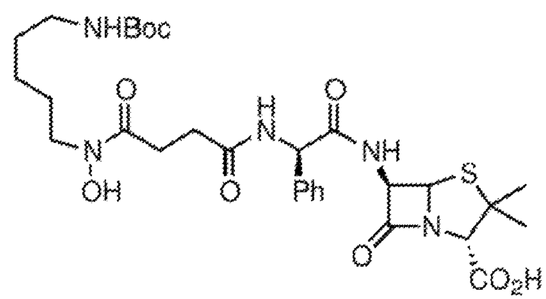 | | AD=0mm AD=16mm |

FIG. 12AAAAAAO
| Compound | Cpd Type | Structure | Pa01 | Pa KW799/wt |
|---|---|---|---|---|
| YML-1-34cr | | 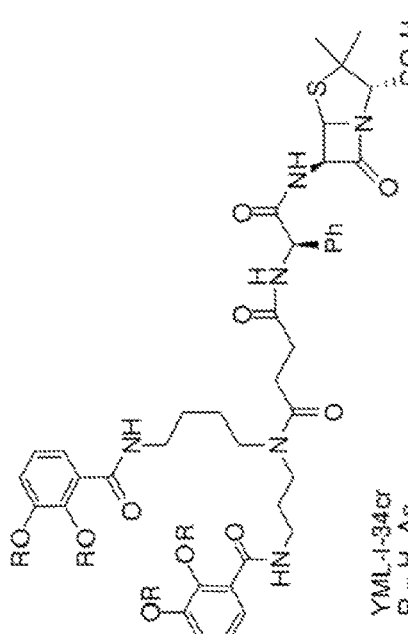 YML-1-34cr R = H, Ac | | .39μM |
| YML-1-45cr | | 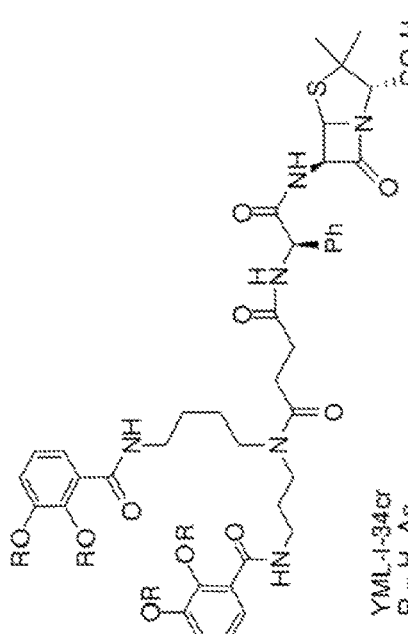 | | AD=18/26Pmm |

FIG. 12AAAAAAP

| Compound | Cpd Type | Structure | PaO1 | Pa KW799/wt |
|---|---|---|---|---|
| YML-1-47 | BisCatechol-Benzylethers free acid | 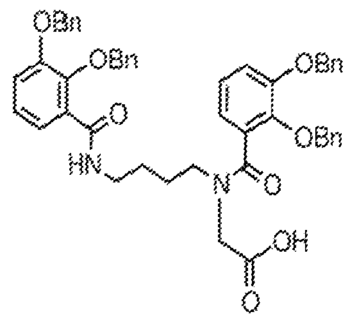 | >200µM | >200µM |
| YML-1-50cr | | 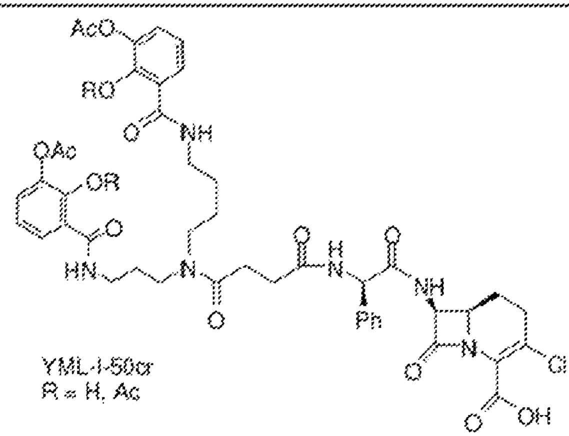 | | >200µM |

FIG. 12AAAAAAQ

| Compound | Cpd Type | Structure | Pa01 | Pa KW799/wt |
|---|---|---|---|---|
| YML-1-54 | BisCatechol-t-Butyl ester | 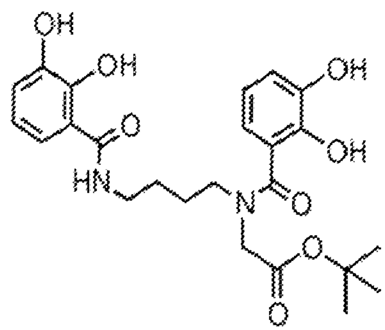 | | |
| YML-1-57 cr | | | >200μM | >200μM |
| YML-1-57 | Acetylated BisCatechol-loracarbef | 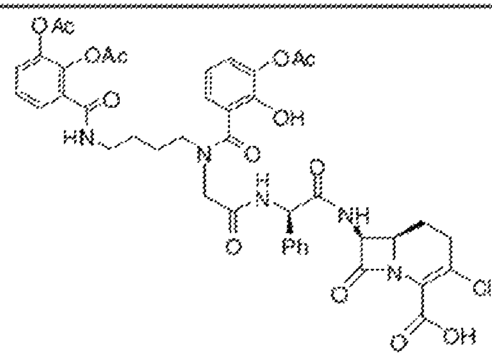 | .78μM<br>1.0μM | .025μM  .033 |

FIG. 12AAAAAAR

| Compound | Cpd Type | Structure | PaO1 | Pa KW799/wt |
|---|---|---|---|---|
| YML-1-58 | BisCatechol free acid | 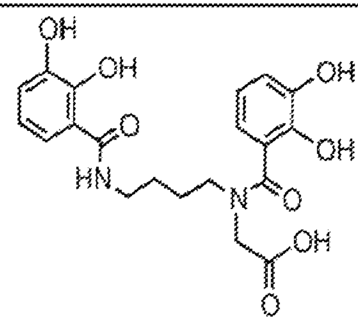 | >200μM | >200μM |
| YML-1-60 | BisCatechol-loracarbef | 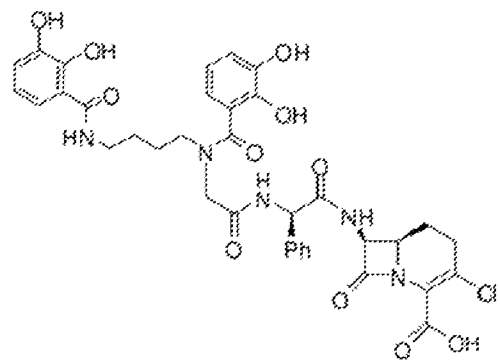 | 1.5μM | .025μM |

FIG. 12AAAAAAS

| Compound | Cpd Type | Structure | PaO1 | Pa KW799/wt |
|---|---|---|---|---|
| YML-1-62 | BisCatechol-Ampicillin | 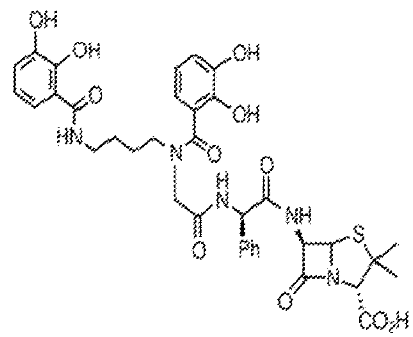 | .0156μM | .0156μM 0.025μM |
| YML-1-77 | BisCatechol-aztreonam Hunig's Base salt | 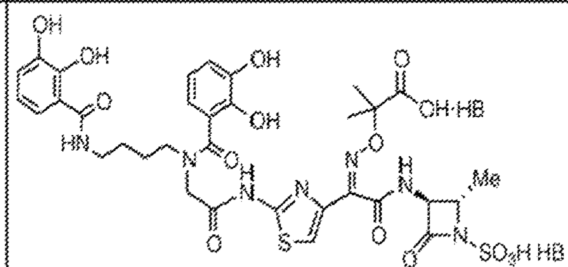 | 1.56μM | 0.2μM |
| Aztreonam | antibiotic | 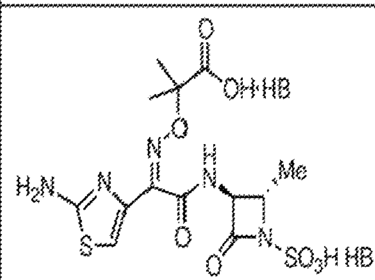 | 6.25μM | 1.56μM |

FIG. 12AAAAAAT

| Compound | Cpd Type | Structure | Pa01 | Pa KW799/wt |
|---|---|---|---|---|
| YML-1-78 | BisCatechol-aztreonam K salt | 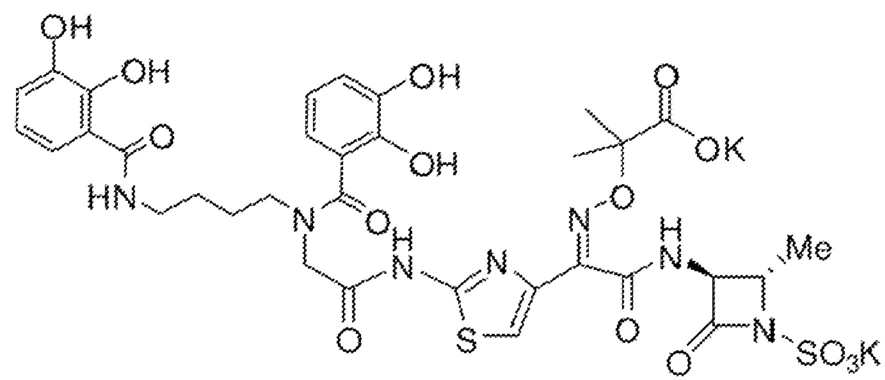 | >50μM | 0.78μM |
| YML-1-80 | BisCatechol-pleuromutlin | 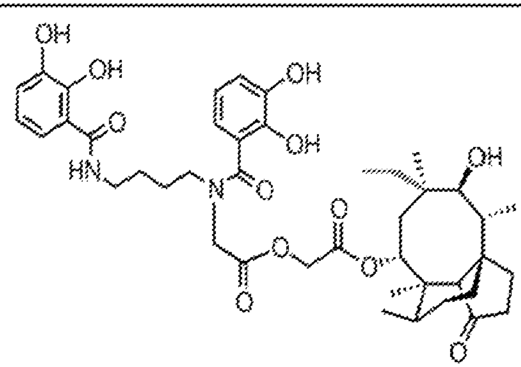 | | |

FIG. 12AAAAAU

| Compound | Cpd Type | Structure | Pa01 | Pa KW799/wt |
|---|---|---|---|---|
| Pleuromutilin | antibiotic | 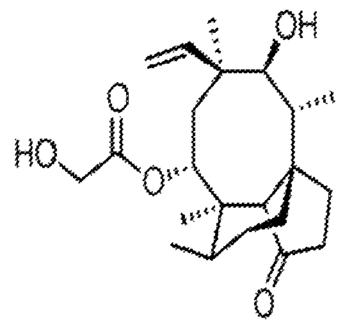 | | 200µM |
| YML-1-91 | | 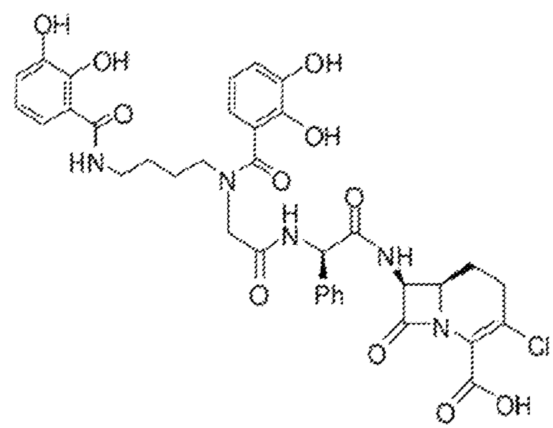 | .25µM | 0.05µM |

FIG. 12AAAAAAV

| Compound | Cpd Type | Structure | paO1 | Pa KW799/wt |
|---|---|---|---|---|
| YML-1-93 | | 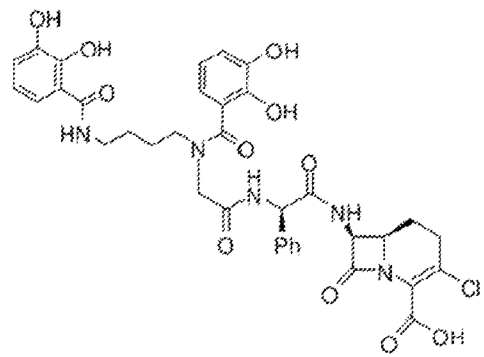 | .25-.5µM | 0.05µM |
| YML-1-96 | | 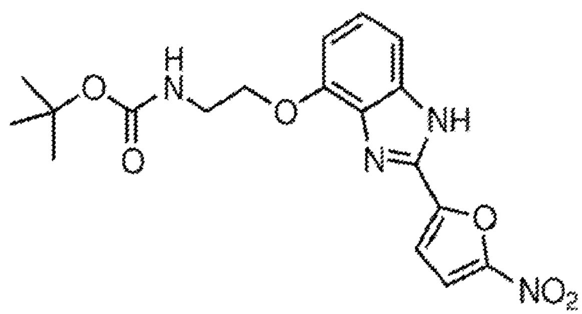 | | |
| loracarbef | antibiotic | | >200µM | >200µM |
| Ampicillin | antibiotic | | >200µM | >200µM |

FIG. 12AAAAAAW

| Compound | Cpd Type | Structure | Pa01 | Pa KW799/wt |
|---|---|---|---|---|
| cefaclor | antibiotic | | | >50μM |
| YML-1-104 | | 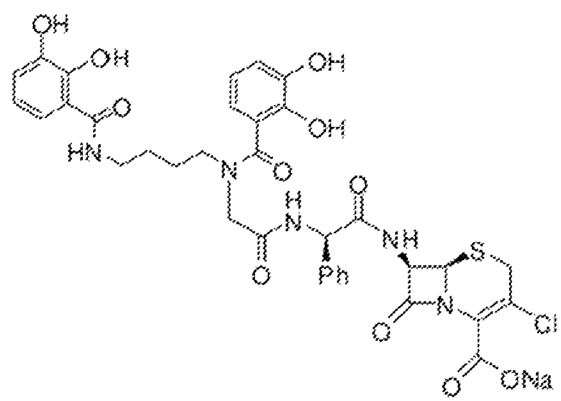 | | |
| YML-1-105 Sulbactam | | | 6.25μM >80ug/ml | 0.78μM-1.56μM >80ug/ml |

FIG. 12AAAAAAX
| Compound | Cpd Type | Structure | PaO1 | Pa KW799/wt |
|---|---|---|---|---|
| YML-1-96 | | 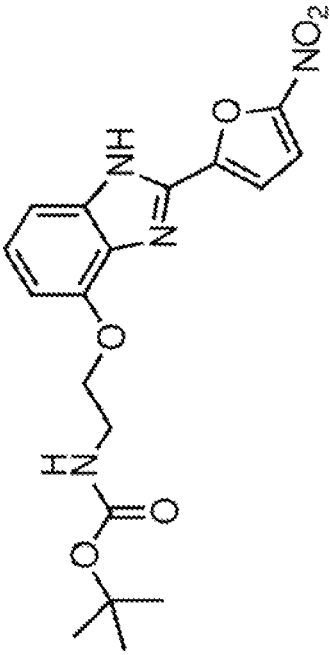 | | zone @ .5mM=17.5P |
| YML-1-104 (not pure) | | 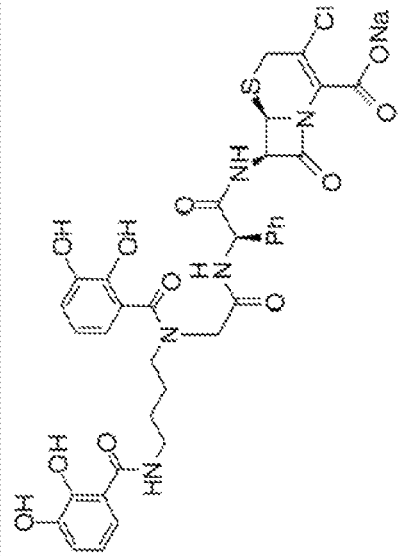 | 1.56μM | 0.233μM |

FIG. 12AAAAAAY
| Compound | Cpd Type | Structure | PaO1 | Pa KW799/wt |
|---|---|---|---|---|
| YML-1-105 (not pure) | | 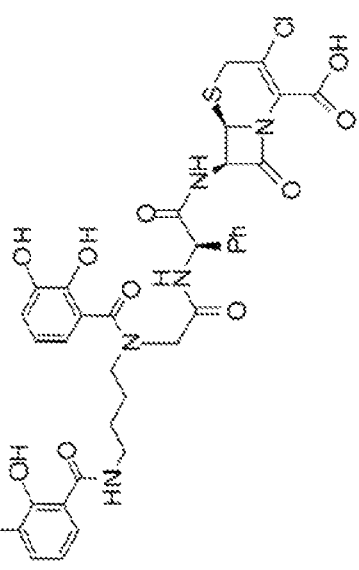 | 3.13μM 6.25μM | .78-1.56μM |
| cefaclor | | | >50μM | >50μM |
| YML-1-109 | | 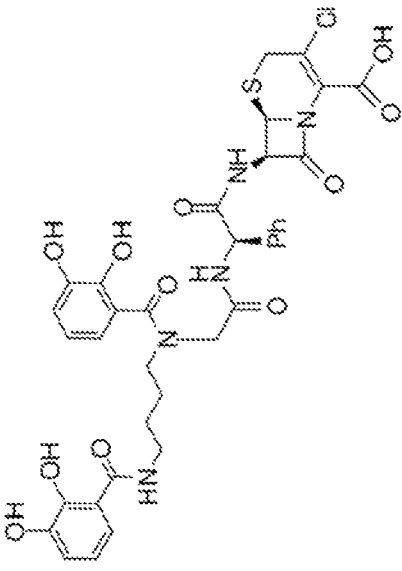 | 1.56μM | 0.05μM |

FIG. 12AAAAAAZ

| Compound | Cpd Type | Structure | PaO1 | Pa KW799/wt |
|---|---|---|---|---|
| YML-1-115 (sodium salt of YML-1-60) | | 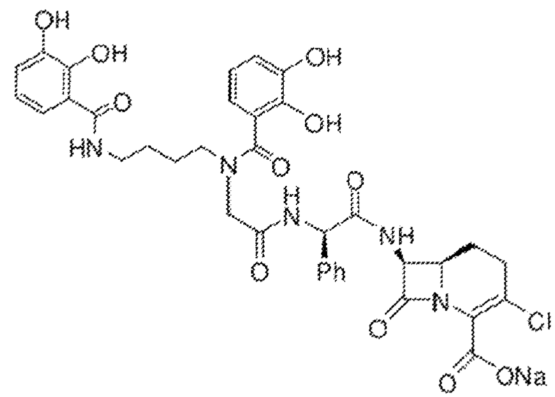 | | |
| YML-1-117 | | 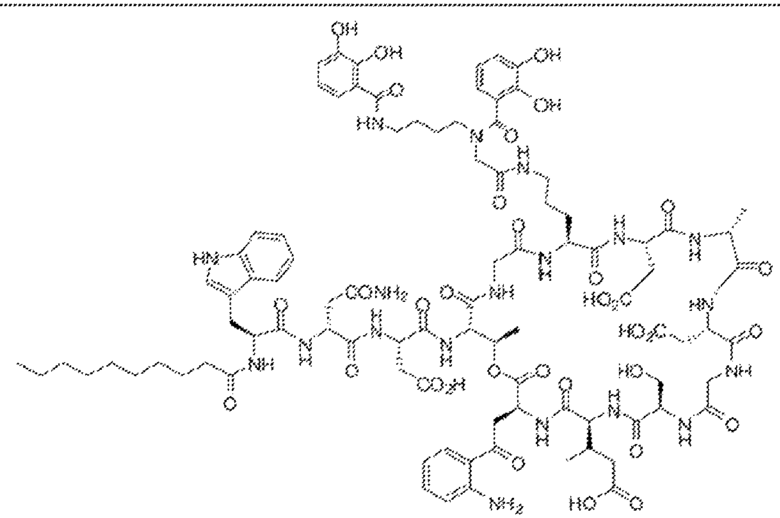 | | >100µM |

FIG. 12AAAAAAAA

| Compound | Cpd Type | Structure | Pa01 | Pa KW799/wt. |
|---|---|---|---|---|
| YML-1-119 (crude) | | 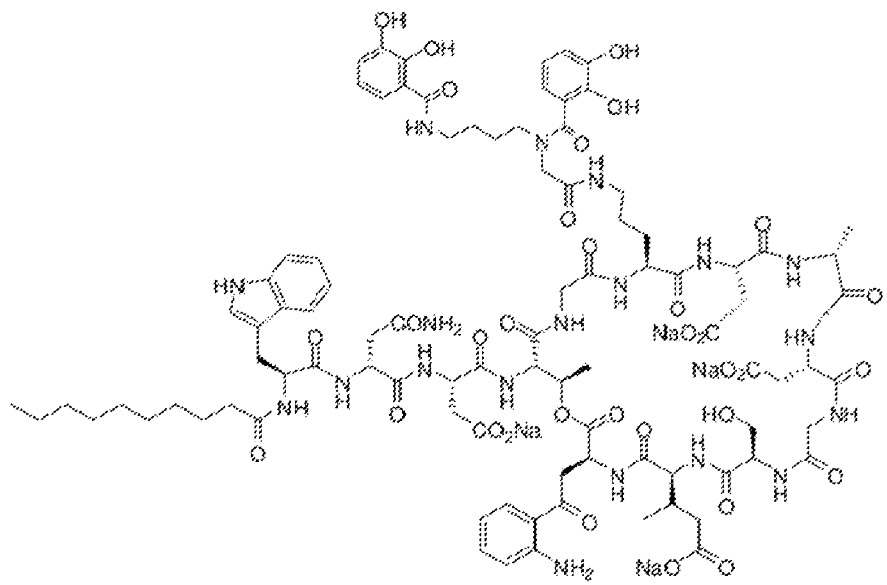 | | >200µM |

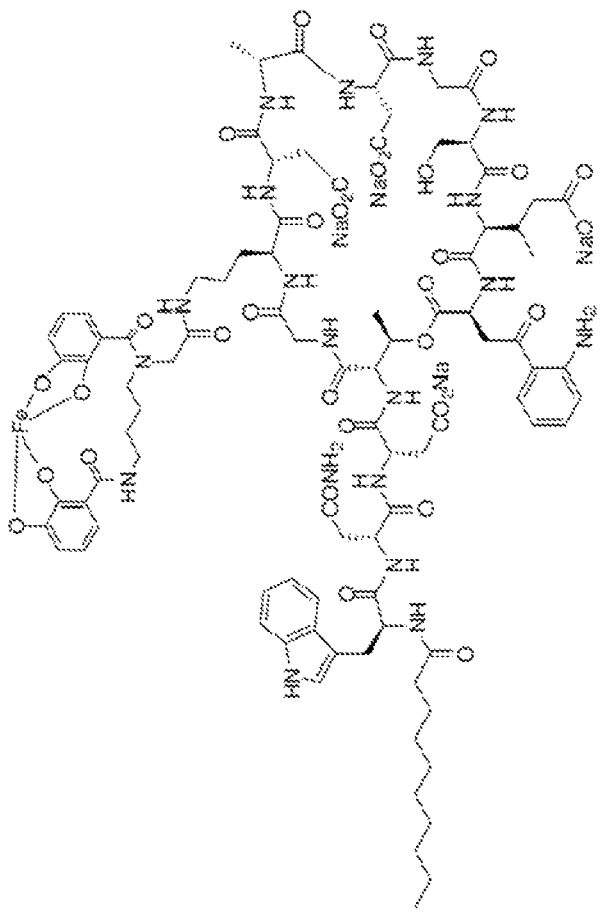
FIG. 12AAAAAAAB

REDUCTION-TRIGGERED ANTIBACTERIAL SIDEROMYCINS

CROSS-REFERENCE TO RELATED APPLICATIONS

This application claims priority to U.S. Provisional Application No. 61/894,770, filed Oct. 23, 2013, the entire contents of which are hereby incorporated by reference.

STATEMENT OF FEDERALLY SPONSORED RESEARCH AND DEVELOPMENT

This research was supported in part by grant 2R01 AI054193 from the National Institutes of Health. The United States government has certain rights in this invention.

FIELD OF THE INVENTION

The present application relates to compounds and compositions having antibacterial activity, and methods of making and using.

BACKGROUND

The ever-growing bacterial resistance to antibiotics is emerging as a serious problem that poses great threat to public health. Not only is the situation worsened by the lack of new antibiotics being created, the increasing use and misuse of existing antibiotics are also significant contributors that promote resistance. Of several modes of resistance mechanisms, the inability of some antibiotics to enter the cell via size-restricted porins is especially significant. Thus, there is always a dire need for improved drug-delivery processes to overcome this permeability problem.

The idea of conjugation antibiotics to bacterial iron chelators, known as siderophores, to facilitate transport of antibiotics into the bacterial cell has attracted much attention in the past decades. Under iron-limited conditions, bacteria synthesize and excrete siderophores for extracellular solubilization of otherwise insoluble iron. The siderophore-Fe (III) complexes are recognized by specific bacterial membrane receptors, and then translocated across the cell membrane in the presence of certain ATP-dependent active transporters. Once inside the cell, the iron is released from the siderophore-Fe(III) complex, usually via a reductive mechanism, to give Fe(II) to which siderophores bind much weaker for further usage. Since bacterial iron acquisition largely relies on the siderophore pathway, especially under iron-limited growth conditions during invasion of a host, the use of siderophore-drug conjugates has become an attractive way to bypass the bacterial permeability barrier and thus improve the efficacy of the drug and reduce the chances of resistance development. Several naturally occurring siderophore-antibiotic conjugates, such as albomycins and salmycins, have been proven to use the iron transport system to enter the targeted bacteria, and consequently are very effective antibacterial agents (FIG. 1). Extensive studies of albomycins have revealed, however, that the toxic thionucleoside is enzymatically released after the conjugate is transported. Salmycins, albeit less studied, are proposed to release the aminoglycoside antibiotic via an intramolecular cyclization process triggered by iron reduction. In both cases, an intracellular drug release process is believed to play a key role for the activity of the conjugates.

A series of synthetic siderophore-drug conjugates with potential drug release linkers have been reported. For example, pyoverdin and pyochelin, the two native siderophores of *Pseudomonas aeruginosa*, were conjugated to fluoroquinolones with both stable and hydrolysable linkers to target the corresponding siderophore producing strain. Biological assays revealed that conjugates with a labile linker which could release the drug displayed greatest activities. However, the methylenedioxy linker was non-specifically hydrolysable, which undesirably led to premature release of the antibiotic in the extracellular media.

In another approach, a so-called "trimethyl lock"-induced lactonization, which is triggered by the action of enzymes such as esterases/phosphatases, has been used for the drug release process in siderophore-drug conjugates. The chemical nature of trimethyl lock 1 (shown in FIG. 2) is an o-hydroxycinnamic acid derivative in which unfavorable steric interactions between three methyl groups encourage rapid lactonization to form a hydrocoumarin. However, like the pyoverdin/pyochelin-fluoroquinolone examples mentioned above, the esterase/phosphatase triggered linkers also have the disadvantage of being hydrolyzed by some extracellular hydrolases secreted into the culture medium by bacteria.

BRIEF DESCRIPTION OF THE DRAWINGS

FIG. 8 shows cyclic votammograms of 11Fe (FIG. 8A) and 11Ga (FIG. 8B).

DETAILED DESCRIPTION OF THE SEVERAL EMBODIMENTS

In one embodiment, siderophore-antibiotic sideromycin conjugates that include a potential reduction triggered linker for drug release are provided. In another embodiment, the "trimethyl lock" based linker incorporated in the conjugates may be activated through the reductive pathway of bacterial iron metabolism. In another embodiment, a sideromycin conjugate is provided in which the reduction triggered linker is thermodynamically reducible by common biological reductants, which further is believed to give rise to lactonization within a short time range and with concomitant release of the drug or antibiotic. In another embodiment, sideromycin antibacterial conjugates with the reduction triggered linker are provided, which are more potent than their counterparts having a stable (non-reduction-triggered) linker. In one embodiment, novel reduction triggered linkers are provided, which have a drug release function that can be selectively triggered inside microbial cells.

In contrast to the extracellular esterases/phosphatases which are commonly seen, ferric reductases, the enzymes responsible for iron release from siderophore-Fe(III) complexes, are found predominantly inside bacteria cells with few exceptions. Moreover, most ferric reductases lack substrate specificity, and the inventors have found that they may be suitable targets for the development of drug release linkers for use in siderophore-drug conjugates. The inventors have also found that the "trimethyl lock" 1 may provide an attractive mechanism through which a reduction triggered linker can release antibiotics in a controlled manner. In the present application, a quinone derivative, shown in FIG. 2 in the conjugate 2, is used as the precursor to the "trimethyl lock" structure, and the to-be-released drug is condensed with the carboxyl group. As seen in Scheme 1 in FIG. 2, the quinone derivative includes a reduction triggered linker having the following formula Q:

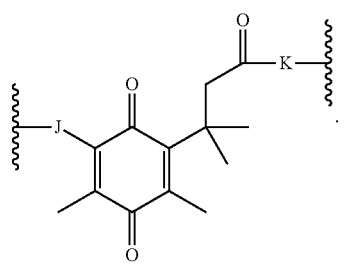

Figure 1:
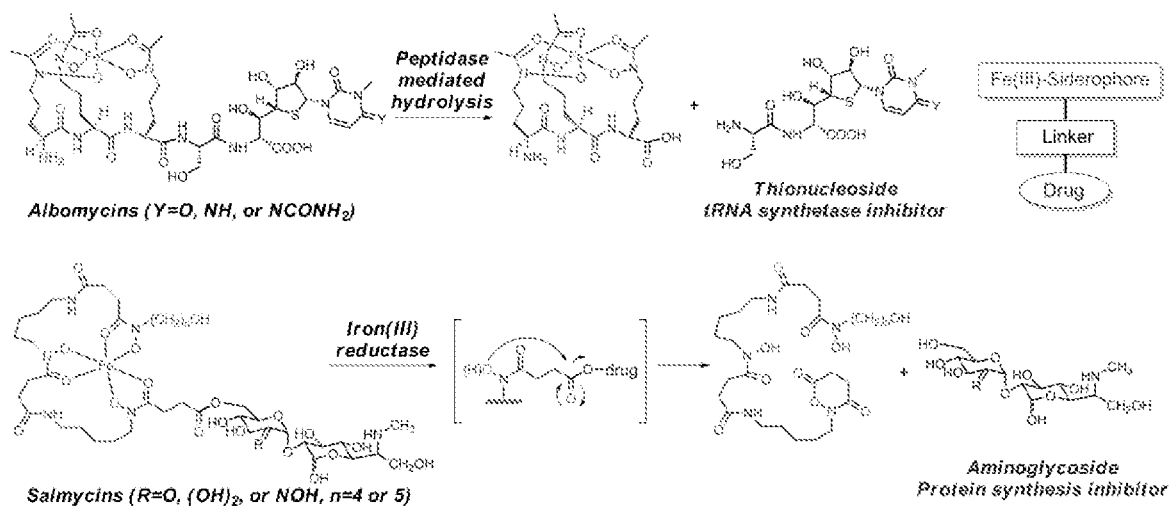
FIG. 1 illustrates an example of conventional siderophore drug conjugates and two naturally occurring examples, albomycin and salmycin.
Figure 2:
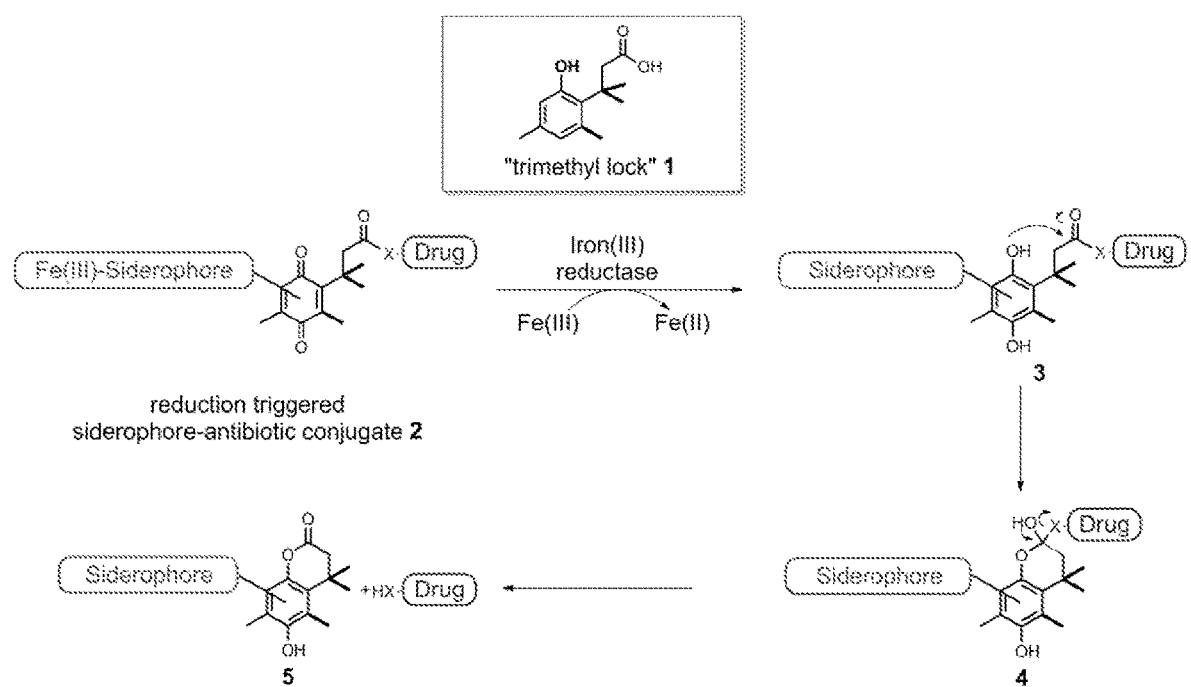
FIG. 2 shows Scheme 1, in which one embodiment of a "trimethyl lock" derived siderophore-antibiotic conjugate is illustrated.

Once or as the conjugate 2 having the reduction triggered linker Q (J and K are defined hereinbelow) is transported into the microbe, it is believed that during the reduction of Fe(III) to Fe(II), the quinone linker in close proximity is also reduced by hydride donors used to reduce Fe(III), for example, flavin, NAD(P)H, and others. The resulting hydroquinone 3 with the "trimethyl lock" structure has only a transient lifetime, which is believed to rapidly cyclize to form lactone 5 with concomitant release of the drug. In one embodiment, the "x" in Scheme 1 of FIG. 2 is the "K" in the reduction triggered linker Q.

In one embodiment, a compound is provided, comprising:
an Fe(III)-binding siderophore;
one or more optional linker covalently bound to the siderophore;
a drug; and
an Fe(III) to Fe(II) reduction triggered linker having the following formula Q bound to the drug and the linker or, if no linker is present, then bound to the drug and the siderophore:

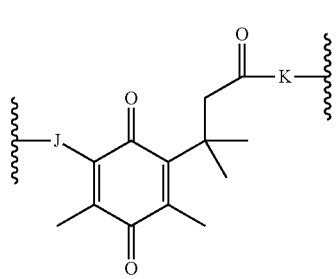

wherein J is a covalent bond or group having the formula —(CO)NR'— or —NR'—, J being bound to the linker or, if no linker is present, then to the siderophore;
wherein K is a covalent bond, —O—, or —NR'—, K being bound to the drug; and
R' is independently H or alkyl;
or pharmaceutically acceptable salt or solvate thereof.

In one embodiment, a compound is provided, comprising:
an Fe(III)-bound siderophore;
one or more optional linker covalently bound to the siderophore;
a drug; and
an Fe(III) to Fe(II) reduction triggered linker having the following formula Q bound to the drug and the linker or, if no linker is present, then bound to the drug and the siderophore:

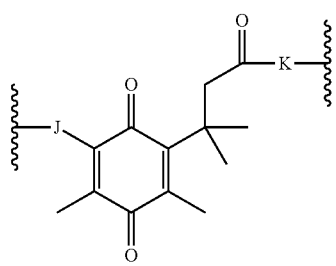

wherein J is a covalent bond or group having the formula —(CO)NR'— or —NR'—, J being bound to the linker or, if no linker is present, then to the siderophore;
wherein K is a covalent bond, —O—, or —NR'—, K being bound to the drug; and
R' is independently H or alkyl;
or pharmaceutically acceptable salt or solvate thereof.

In one embodiment, J is a covalent bond. In another embodiment, J is a group having the formula —(CO)NR'— or —NR'—. In another embodiment, J is a group having the formula —(CO)NH— or —NH—.

In one embodiment, wherein the optional linker is present, J is bound to the linker. In another embodiment, wherein the optional linker is not present, J is bound to the siderophore.

In one embodiment, K is a covalent bond. In another embodiment, K is —O— or —NR'—. In another embodiment K is —NH—.

In one embodiment, a pharmaceutical composition is provided, comprising one or more of the aforementioned compounds, or mixture thereof and a pharmaceutically acceptable diluent or carrier.

In one embodiment, a method is provided for treating a bacterial infection in a subject, comprising administering one or more of the aforementioned compounds, or mixture thereof to the subject.

In one embodiment, a method is provided for treating a bacterial infection in a subject, comprising administering the aforementioned pharmaceutical composition to the subject.

In one embodiment, a method is provided for killing or inhibiting the growth of a bacterium, comprising contacting the bacterium with one or more of the aforementioned compounds, or a mixture thereof.

In one embodiment, a method is provided for killing or inhibiting the growth of a bacterium, comprising contacting the bacterium with the aforementioned pharmaceutical composition.

In one embodiment, the siderophore is a natural siderophore, semi-synthetic siderophore, synthetic siderophore, or combination thereof. In one embodiment, the siderophore is a natural siderophore In one embodiment, the siderophore is a semi-synthetic siderophore. In one embodiment, the siderophore is a synthetic siderophore.

Natural siderophores are known, and are not particularly limiting. Any natural siderophore with pendant functionality (amine, alcohol, carboxylic acid) may be suitably used. Non-limiting examples of natural siderophores include Desferrioxamine A1, Desferrioxamine A2, Desferrioxamine B, Desferrioxamine D1, Desferrioxamine D2, Desferrioxamine E, Desferrioxamine G1, Desferrioxamine G2A, Desferrioxamine G2B, Desferrioxamine G2C, Desferrioxamine H, Desferrioxamine T1, Desferrioxamine T2, Desferrioxamine T3, Desferrioxamine T7, Desferrioxamine T8, Desferrioxamine X1, Desferrioxamine X2, Desferrioxamine X3, Desferrioxamine X4, Desferrioxamine Et1, Desferrioxamine Et2, Desferrioxamine Et3, Desferrioxamine Te1, Desferrioxamine Te2, Desferrioxamine Te3, Desferrioxamine P1, Ferrichrome, Ferrichrome C, Ferricrocin, Sake Colorant A, Ferrichrysin, Ferrichrome A, Ferrirubin, Ferrirhodin, Malonichrome, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Tetraglycine ferrichrome, Des(diserylglycyl)-ferrirhodin, Basidiochrome, Triacetylfusarinine, Fusarinine C, Fusarinine B, Neurosporin, Coprogen, Coprogen B (Desacetylcoprogen), Triornicin (Isoneocoprogen I), Isotriornicin (Neocoprogen I), Neocoprogen II, Dimethylcoprogen, Dimethylneocoprogen I, Dimethyltriornicin, Hydroxycopropen, Hydroxy-neocoprogen I, Hydroxyisoneocoprogen I, Palmitoylcoprogen, Amphibactin B, Amphibactin C, Amphibactin D, Amphibactin E, Amphibactin F, Amphibactin G, Amphibactin H, Amphibactin I, Ferrocin A, Coelichelin, Exochelin MS, Vicibactin, Enterobactin (Enterochelin), Agrobactin, Parabactin, Fluvibactin, Agrobactin A, Parabactin A, Vibriobactin, Vulnibactin, Protochelin, Corynebactin, Bacillibactin, Salmochelin S4, Salmochelin S2, Rhizoferrin, Rhizoferrin analogues, Enantio Rhizoferrin, Staphyloferrin A, Vibrioferrin, Achromobactin, Mycobactin P, Mycobactin A, Mycobactin F, Mycobactin H, Mycobactin M, Mycobactin N, Mycobactin R, Mycobactin S, Mycobactin T, Mycobactin Av, Mycobactin NA (Nocobactin), Mycobactin J, Formobactin, Nocobactin NA, Carboxymycobactin, Carboxymycobactin 1, Carboxymycobactin 2, Carboxymycobactin 3, Carboxymycobactin 4, Pyoverdin 6.1 (Pseudobactin), Pyoverdin 6.2, Pyoverdin 6.3 (Pyoverdin Thai), Pyoverdin 6.4 (Pyoverdin 9AW), Pyoverdin 6.5, Pyoverdin 6.6, Isopyoverdin 6.7, (Isopyoverdin BTP1), Pyoverdin 6.8, Pyoverdin 7.1, Pyoverdin 7.2, (Pyoverdin BTP2), Pyoverdin 7.3, (Pyoverdin G+R), Pyoverdin 7.4, (Pyoverdin PVD), Pyoverdin 7.5, (Pyoverdin TII), Pyoverdin 7.6, Pyoverdin 7.7, Pyoverdin 7.8, (Pyoverdin PL8), Pyoverdin 7.9, (Pyoverdin 11370), Pyoverdin, Pyoverdin 7.11, (Pyoverdin 19310), Pyoverdin 7.12, (Pyoverdin 13525), Isopyoverdin 7.13, (Isopyoverdin 90-33), Pyoverdin 7.14, (Pyoverdin R'), Pyoverdin 7.15, Pyoverdin 7.16, (Pyoverdin 96-312), Pyoverdin 7.17, Pyoverdin 7.18, Pyoverdin 7.19, Pyoverdin 8.1, (Pyoverdin A214), Pyoverdin 8.2, (Pyoverdin P19), Pyoverdin 8.3, (Pyoverdin D-TR133), Pyoverdin 8.4, (Pyoverdin 90-51), Pyoverdin 8.5, Pyoverdin 8.6, (Pyoverdin 96-318), Pyoverdin 8.7, (Pyoverdin I-III), Pyoverdin 8.8, (Pyoverdin CHAO), Pyoverdin 8.9, (Pyoverdin E), Pyoverdin 9.1, Pyoverdin 9.2, (Pyoverdin Pau), Pyoverdin 9.3, Pyoverdin 9.4, Pyoverdin 9.5, (Pyoverdin 2392), Pyoverdin 9.6, Pyoverdin 9.7, (Pseudobactin 589A), Pyoverdin 9.8, (Pyoverdin 2461), Pyoverdin 9.9, Pyoverdin 9.10, (Pyoverdin 95-275), Pyoverdin 9.11, (Pyoverdin C), Pyoverdin 9.12, Pyoverdin 10.1, (Pyoverdin 2798), Pyoverdin 10.2, Pyoverdin 10.3, (Pyoverdin 17400), Pyoverdin 10.4, Pyoverdin 10.5, (Pyoverdin 18-1), Pyoverdin 10.6, (Pyoverdin 1, 2), Isopyoverdin 10.7, (Isopyoverdin 90-44), Pyoverdin 10.8, Pyoverdin 10.9, (Pyoverdin 2192), Pyoverdin 10.10, Pyoverdin 11.1, (Pyoverdin 51W), Pyoverdin 11.2, (pyoverdin 12), Pyoverdin 12.1, (Pyoverdin GM), Pyoverdin 12.2, (Pyoverdin 1547), Azoverdin, Azotobactin 87, Azotobactin D, Heterobactin A, Ornibactin—C4, Ornibactin—C6, Ornibactin—C8, Aquachelin A, Aquachelin B, Aquachelin C, Aquachelin D, Marinobactin A, Marinobactin B, Marinobactin C, Marinobactin D1, Marinobactin D2, Marinobactin E, Loihichelin A, Loihichelin B, Loihichelin C, Loihichelin D, Loihichelin E, Loihichelin F, Schizokinen, Aerobactin, Arthrobactin, Rhizobactin 1021, Nannochelin A, Nannochelin B, Nannochelin C, Acinetoferrin, Ochrobactin A, Ochrobactin B, Ochrobactin C, Snychobactin A, Snychobactin B, nychobactin C, Mugineic acid, 3-Hydroxymugineic acid, 2'-Deoxymugineic acid, Avenic acid, Distichonic acid, Deoxydistichonic acid, Rhizobactin, Staphyloferrin B, Alterobactin A, Alterobactin B, Pseudoalterobactin A, Pseudoalterobactin B, Petrobactin, Petrobactin sulphonate, Petrobactin disulphonate, Fusarinine A, Exochelin MN, Ornicorrugatin, Maduraferrin, Alcaligin, Putrebactin, Bisucaberin, Rhodotrulic acid, Dimerum acid, Amycolachrome, Azotochelin, (Azotobactin), Myxochelin, Amonabactin T789, Amonabactin P750, Amonabactin T732, Amonabactin P693, Salmochelin S1, Serratiochelin, Anachelin 1, Anachelin 2, Pistillarin, Anguibactin, Acinetobactin, Yersiniabactin, Micacocidin, Deoxyschizokinen, Heterobactin B, Desferrithiocin, Pyochelin, Thiazostatin, Enantio-Pyochelin, 2,3-Dihydroxybenzoylserine, Salmochelin SX, Citrate, Chrysobactin, Aminochelin, Siderochelin A, Aspergillic acid, Itoic acid, Cepabactin, Pyridoxatin, Quinolobactin, Ferrimycin A, Salmycin A, Albomycin, or combination thereof.

Other natural siderophores may be found in Robert C. Hider and Xiaole Kong *Nat. Prod. Rep.*, 2010, 27, 637-657, and the appendices thereof, the entire contents of which are hereby incorporated by reference.

In one embodiment, the siderophore is a semi-synthetic or synthetic siderophore. Non-limiting examples of these siderophores may be found in the table in FIG. 12. In the figure, some siderophores have linkers and/or antibiotics attached, which linkers and/or antibiotics in some embodiments are not to be considered part of the siderophore. In such embodiments, the siderophore—without the linker and/or antibiotic shown in the table—may be suitably used in the compounds described herein.

In one embodiment, the siderophore comprises one or more iron(III)-binding ligand.

In one embodiment, the siderophore comprises one or more iron(III)-binding catechol, hydroxamic acid, beta-hydroxy acid, heteroaromatic ligand, or combination thereof.

In one embodiment, the compound has one of the following formulas:

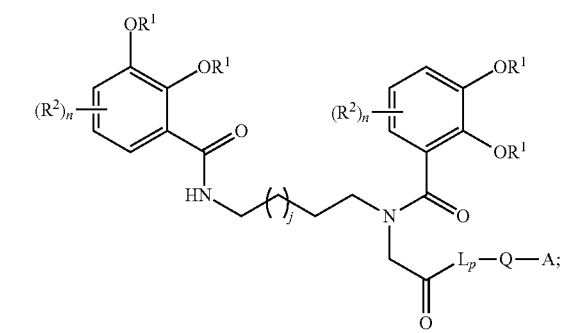

(Ia)

(IIa)

(IIIa)

(IVa)

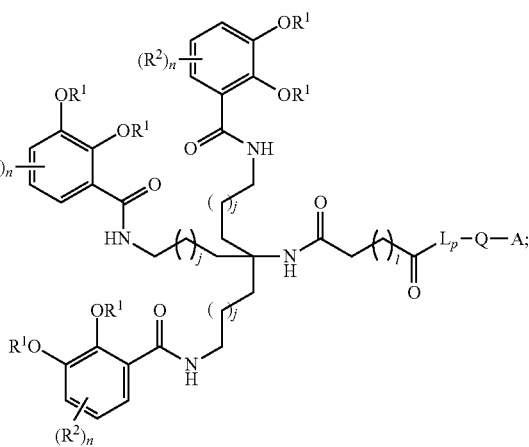

(Va)

wherein

A is drug;

each L is independently a linker;

each $R^1$ is independently H, —C(═O)alkyl, —C(═O)aryl, or —C(═O)O-alkyl;

each $R^2$ is independently H, alkyl, alkoxy, hydroxy, carboxy, halo, nitro, amino, or cyano;

each n is independently 1, 2, or 3;

each p is independently 0-11;

each j is independently 0-11;

each k is independently 1-11;

each l is independently 1-11;

each o is independently 0-11; and each m is independently 0-11;

Fe(III)-bound form thereof, pharmaceutically acceptable salt thereof, solvate thereof, or combination thereof.

In one embodiment, the compound has one of the following formulas:

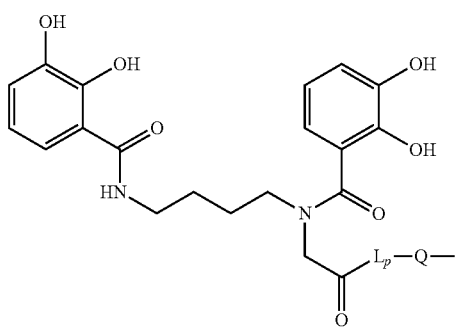

(Ib)

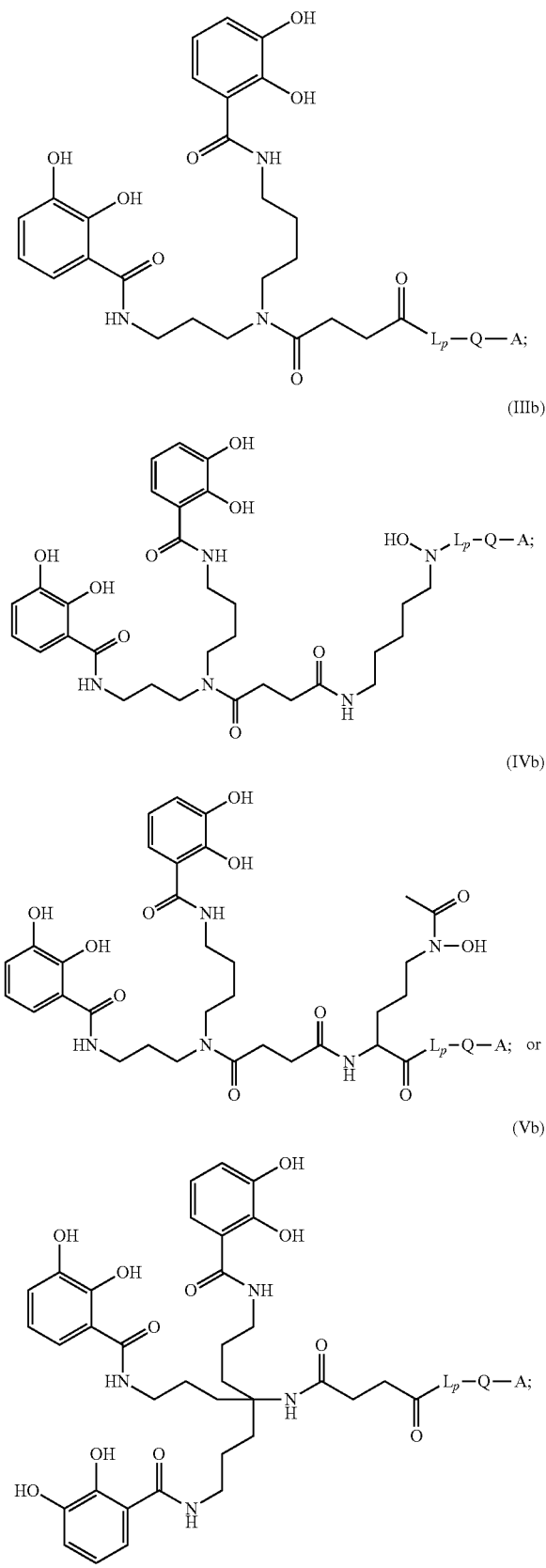

wherein
A is a drug;
each L is independently a linker; and
each p is independently 0-11;

Fe(III)-bound form thereof, pharmaceutically acceptable salt thereof, solvate thereof, or combination thereof.

In the formulas herein, each n is independently 1, 2, or 3.

In the formulas herein, each p is independently 0-11, which independently includes all values and subranges therebetween, including 0, 1, 2, 3, 4, 5, 6, 7, 8, 9, 10, and 11.

In the formulas herein, each j is independently 0-11, which independently includes all values and subranges therebetween, including 0, 1, 2, 3, 4, 5, 6, 7, 8, 9, 10, and 11.

In the formulas herein, each k is independently 1-11, which independently includes all values and subranges therebetween, including 0, 1, 2, 3, 4, 5, 6, 7, 8, 9, 10, and 11.

In the formulas herein, each l is independently 1-11, which independently includes all values and subranges therebetween, including 0, 1, 2, 3, 4, 5, 6, 7, 8, 9, 10, and 11.

In the formulas herein, each o is independently 0-11, which independently includes all values and subranges therebetween, including 0, 1, 2, 3, 4, 5, 6, 7, 8, 9, 10, and 11.

In the formulas herein, each m is independently 0-11, which independently includes all values and subranges therebetween, including 0, 1, 2, 3, 4, 5, 6, 7, 8, 9, 10, and 11.

In one embodiment, one or more than one (optional) linker is present. In one embodiment, more than one type of linker is present. In one embodiment, one linker is present. In one embodiment, no linker is present.

In one embodiment, a pharmaceutical composition is provided, which comprises the compound or mixture thereof and a pharmaceutically acceptable diluent or carrier.

In one embodiment, the pharmaceutical composition contains a mixture of different siderophore—optional linker—reduction triggered linker—drug conjugates. In another embodiment, the pharmaceutical composition contains one type of siderophore—optional linker—reduction triggered linker—drug conjugate. In one embodiment, the pharmaceutical composition contains both Fe(III)-bound and Fe(III)-binding (i.e., the siderophore is not bound to Fe(III)) conjugates. In another embodiment, the pharmaceutical composition contains only one or more Fe(III)-bound conjugates. In another embodiment, the pharmaceutical composition contains only one or more Fe(III)-binding conjugates.

In one embodiment, the diluent or carrier comprises a pharmaceutically acceptable hydrogel.

In one embodiment, the bacterial infection is caused by an antibiotic-resistant bacterium.

In one embodiment, the bacterial infection is caused by a Gram-positive or Gram-negative bacterium.

One embodiment provides a siderophore—optional linker—reduction triggered linker—drug conjugate in which the siderophore includes one or more bi-dentate, tetra-dentate or hexadentate iron binding groups (catechols, ortho-hydroxy phenyl oxazolines, oxazoles, thiazolines, thiazoles, hydroxamic acids, alpha-hydroxy carboxylic acids or amides, pyridines, hydroxyl pyridones and combinations thereof). In one embodiment, the linker may include direct attachment of the siderophore component to the reduction triggered linker either through a carboxylic acid of the siderophore attached to one or more amine components of the reduction triggered linker. Alternatively, the optional linker may include spacer groups commonly used in bioconjugation chemistry, including PEGylated groups of various lengths. Other attachment methods may suitably include "click chemistry", carbohydrate linkages or other ligation.

Other non-limiting examples of siderophores include bis-catechols, tris-catechols, or derivatives of natural siderophores including entrobactin and derivatives, and mixed ligand siderophores, and natural siderophores including mycobactins.

In some embodiments, formulations of the sideromycins conjugate include those compatible with injection using common vehicles, including those commonly used for antibiotics in systemic infections due to Gram-positive and Gram-negative bacteria and formulation in creams and gels, including hydrogels, for treatment of topical infections due to Gram-positive and Gram-negative bacteria.

In one embodiment, conjugates of siderophores, optional linkers, reduction triggered linker, and various antibiotics are provided. The conjugates can demonstrate selectively potent anti-bacterial activity, including anti-pseudomonal activity, while the parent antibiotics, themselves, are inactive. In one embodiment, iron transport-mediated drug delivery systems comprising the compounds described herein are provided.

In one embodiment, conjugates described herein exhibit significantly enhanced antibacterial activities against Gram-negative species compared to the parent drugs, especially against *P. aeruginosa*. The conjugates can be assimilated by an induced bacterial iron transport process and their activities may be inversely related to iron concentration, or the conjugates may be administered as the iron(III)-bound complex. In one embodiment, the easily synthesized siderophore conjugates can be used to target antibiotic-resistant Gram-negative bacteria.

In one embodiment, each $R^1$ is acetyl, propanoyl, or benzoyl. In one embodiment, each $R^1$ is acetyl. In another specific embodiment, each $R^1$ is H.

In one embodiment, each $R^2$ is H, alkyl, alkoxy, or hydroxy. In one specific embodiment, each $R^2$ is H. $R^2$ can also be a substituent as described herein.

In some embodiments, each $R^1$ is the same, while in other embodiments, $R^1$ groups can be different. Likewise, in various embodiments, each $R^2$ can be the same, while in other embodiments, $R^2$ groups can be different from each other, for example, depending on the starting material selected to prepare the compounds.

In one embodiment, methods of treating a Gram-negative bacterial infection are provided. The methods can include administering to a subject in need thereof an effective therapeutic amount of a compound described herein, thereby treating the bacterial infection. Another embodiment provides a method of killing or inhibiting the growth of a Gram-negative bacterium where the method includes contacting the bacterium with an effective lethal or inhibitory amount of a compound described herein. The bacterial infection can be caused by an antibiotic-resistant bacterium. In some embodiments, the bacterial infection is caused by a Pseudomonal bacterium. In some specific embodiments, the bacterial infection can be caused by *Pseudomonas aeruginosa, Escherichia coli, Acinetobacter baumannii,* or *Salmonella typhimurium*.

In one embodiment, methods of treating a Gram-positive bacterial infection are provided. The methods can include administering to a subject in need thereof an effective therapeutic amount of a compound described herein, thereby treating the bacterial infection. Another embodiment provides a method of killing or inhibiting the growth of a Gram-positive bacterium where the method includes contacting the bacterium with an effective lethal or inhibitory amount of a compound described herein. The bacterial infection can be caused by an antibiotic-resistant bacterium. In some embodiments, the bacterial infection is caused by a Bacillis bacterium. In some specific embodiments, the bacterial infection can be caused by *B. subtilis, S. aureus,* or *M. luteus*.

In one embodiment, a method is provided for increasing the permeability of a Gram-negative bacterium cell membrane to an antibiotic comprising conjugating an antibiotic to the siderophore, reduction triggered linker, and/or linker described herein and administering the compound to the bacterium cell membrane, thereby increasing the permeability of the Gram-negative bacterium cell membrane to the antibiotic as a result of its conjugation to the siderophore.

In one embodiment, a method is provided for increasing the permeability of a Gram-positive bacterium cell membrane to an antibiotic comprising conjugating an antibiotic to the siderophore, reduction triggered linker, and/or linker described herein and administering the compound to the bacterium cell membrane, thereby increasing the permeability of the Gram-positive bacterium cell membrane to the antibiotic as a result of its conjugation to the siderophore.

In one embodiment, compounds of the formula described herein are provided, as are intermediates for the synthesis of the compounds, as well as methods of preparing the compounds. In one embodiment, the compounds having the formulas described herein may be useful as intermediates for the synthesis of other useful compounds.

Terms and phrases used in this specification have their ordinary meanings as one of skill in the art would understand. Where appropriate, such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched, unbranched, saturated or unsaturated, linear or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3- pentyl, 2-methyl-3-pentyl, 2,3-dimethyl-2-butyl, 3,3-dimethyl-2-butyl, hexyl, octyl, decyl, dodecyl, cyclopropyl, cyclobutyl, cyclopentyl, cyclohexyl, cycloheptyl, and the like. The alkyl can be unsubstituted or optionally substituted, for example, with a substituent described herein. The alkyl can also be optionally partially or fully unsaturated. As such, the recitation of an alkyl group can optionally include both alkenyl or alkynyl groups, linear or cyclic, in certain embodiments. The alkyl can be a monovalent hydrocarbon radical, as described herein, or it can be a divalent hydrocarbon radical (i.e., an alkylene), depending on the context of its use. In one embodiment, one or more carbons in the alkyl group may be replaced with one or more heteroatoms, e.g., O, N, S, P, combination thereof, and the like.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups. In one embodiment, one or more carbons in the aryl group may be replaced with one or more heteroatoms, e.g., O, N, S, P, combination thereof, and the like.

The term "amino acid" refers to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, divalent radicals thereof, salts thereof, or combination thereof.

The term "carboxy" group refers to a univalent —CR"(=O) radical or a —CR"(=O)-containing substituent group. In one embodiment, the carboxy group suitably includes carboxylic acids, aldehydes, ketones, and combinations thereof. The R" group is suitably chosen from any of the substituent groups. In one embodiment, the carboxy group may be attached to the parent structure through one or more independent divalent intervening substituent groups.

The term "amino" group refers to a univalent —NR"R" radical or an —NR"R"-containing substituent group. The R" groups may be the same or different and are suitably and independently chosen from any of the substituent groups. In one embodiment, the amino group may be attached to the parent structure through one or more independent divalent intervening substituent groups.

The term "nitro" group refers to a univalent —NO$_2$ radical or an —NO$_2$-containing substituent group. In one embodiment, the amino group may be attached to the parent structure through one or more independent divalent intervening substituent groups.

The term "cyano" group refers to a univalent —CN radical or a —CN-containing substituent group. In one embodiment, the cyano group may be attached to the parent structure through one or more independent divalent intervening substituent groups.

The term "peptide" refers to polypeptide, protein, oligopeptide, monopeptide, dipeptide, tripeptide, tetrapeptide, pentapeptide, hexapeptide, heptapentide, octapeptide, nonapeptide, decapeptide, undecapeptide, divalent radicals thereof, salts thereof, or combination thereof. In some embodiments, the term peptide may refer to a peptide bond, amide bond, or the like. For example, a peptide or amide bond is a covalent chemical bond formed between two molecules when the carboxyl group of one molecule reacts with the amino group of the other molecule forming a —C(O)NH— bond or peptide link.

A "linker" or "linking group" refers to an organic or inorganic chain or moiety that optionally connects the siderophore to reduction triggered linker Q. The optional linker may be a molecule having end groups respectively tailored to covalently bond with the siderophore and the reduction triggered linker Q. In one embodiment, the optional linker may be covalently attached to the siderophore and reduction triggered linker Q by an ester or amide bond. Nonlimiting examples of the optional linker include a group L where L is or is derived from one or more optionally substituted amino acid, peptide, alkylene, alkenylene, arylene, polyethylene glycol, polypropylene glycol, or combination thereof. Other nonlimiting examples of linkers include a group L where L is or is derived from a divalent radical of the formula —(W)$_a$—(Z)$_b$—(W)$_c$—; wherein a, b, and c are each independently 0-11; wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CR'$_2$)$_x$—, —(CX$_2$)$_y$—, —(CR'$_2$)$_x$—(CX$_2$)$_y$—, —(CR'$_2$CR'$_2$O)$_x$—, —(OCR'$_2$CR'$_2$)$_x$—, —N$^+$(R')$_2$(CR'$_2$)$_y$—, (C$_1$-C$_{12}$)alkylene, (C$_2$-C$_{12}$)alkenylene, (C$_2$-C$_{12}$)alkynylene, combination thereof, or a direct bond; and Z is a divalent moiety selected from (C$_1$-C$_{12}$)alkylene, (C$_2$-C$_{12}$)alkenylene, (C$_2$-C$_{12}$)alkynylene, (C$_3$-C$_8$)cycloalkylene, (C$_6$-C$_{10}$)arylene, —N(R')C(=O)—, —C(=O)N(R')—, —OC(=O)—, —C(=O)O—, —N(R')—, —C(=O)—, —(CY$_2$)—, —(CR'$_2$)$_x$—(CY$_2$)$_y$—, —(OCR'$_2$—CR'$_2$)$_x$—, —(CR'$_2$CR'$_2$O)$_x$—, —C(O)NR' (CR'$_2$)$_y$—, —OP(O)(OR')O—, —OP(O)(OR')O (CR'$_2$)$_y$—, —OP(O)(OR')OCR'$_2$CR' (OR')CR'$_2$—, —N$^+$(R')$_2$(CR'$_2$)$_x$—, or (C$_1$-C$_{12}$)alkylene, (C$_2$-C$_{12}$)alkenylene, or (C$_2$-C$_{12}$)alkynylene, optionally interrupted between two carbons, or between a carbon and an oxygen, with a (C$_3$-C$_8$)cycloalkyl, heteroaryl, heterocycle, or (C$_6$-C$_{10}$)aryl group, divalent amino acid, divalent peptide, combination thereof, or Z is a direct bond; wherein x and y are each independently 0-11; wherein each X is independently a halogen ("halo"): F, Cl, Br, or I; and each R' is independently H, alkyl, aryl, (aryl)alkyl (e.g., benzyl), heteroaryl, (heteroaryl)alkyl, heterocycle, heterocycle(alkyl), or a protecting group; wherein each of W, Z and R' may be optionally substituted with one or more substituent groups; and each of W, Z, and R' may have one or more carbons replaced with one or more heteroatoms, e.g., N, O, S, P, and the like.

In one embodiment, one or more of the W and/or Z groups can independently form or originate from a part of the siderophore and/or -J- of the reduction triggered linker. In another embodiment, one or more parts of the -J- in the reduction triggered linker can independently form or originate from a part of the siderophore or optional linker.

In one embodiment, one or more parts of the —K— in the reduction triggered linker can independently form or originate from a part of the drug.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Nonlimiting examples of substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Other nonlimiting examples of the substituent group include, e.g., —X, —R", —O$^-$, —OR", —SR, —S$^-$, —NR"$_2$, —NR"$_3^+$, =NR", —CX$_3$, —CN, —OCN, —SCN, —N=C=O, —NCS, —NO, —NO$_2$, =N$_2$, —N$_3$, —NC(=O)R", —C(=O)R", —C(=O)NR"R", —S(=O)$_2$O$^-$, —S(=O)$_2$OH, —S(=O)$_2$R", —OS(=O)$_2$OR", —S(=O)$_2$NHR", —S(=O)R", —OP(=O)(OR")$_2$, —P(=O)(OR")$_2$, —OP(=O)(OH)(OR"), —P(=O)(OH)(OR"), —P(=O)(O$^-$)$_2$, —P(=O)(OH)$_2$, —C(=O)R", —C(=O)X, —C(S)R", —C(O)OR", —C(O)O$^-$, —C(S)OR", —C(O)SR", —C(S)SR", —C(O)NR"R", —C(=S)NR"R", —C(=NR")NR"R", wherein each X is independently a halogen ("halo"): F, Cl, Br, or I; and each R" is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

In one embodiment, the drug is an antibiotic. The antibiotic may be suitably bound to the reduction triggered linker Q. In one embodiment, the antibiotic is covalently bound to the reduction triggered linker Q. Generally, any antibiotic having a free amine or hydroxyl or similar functional group may be attached to the reduction triggered linker Q.

In one embodiment, the antibiotic inhibits bacterial or fungal growth or kills bacteria or fungi. Nonlimiting examples of antibiotics that may be useful include but are not limited to those found in http://en.wikipedia.org/wiki/Antibacterial, the entire contents of which are hereby incorporated by reference. Other examples of suitable antibiotics include those found in http://www.sigmaaldrich.com/life-science/biochemicals/biochemical-products.html, the entire contents of which are hereby incorporated by reference. Other examples include lincomycins, beta-lactams, macrolides, ketolides, tetracyclines, sulfur-based antibiotics, oxazolidinones, peptide antibiotics, quinolones, fluoroquinolones, and rifamycins. Other nonlimiting examples of suitable antibiotics include amikacin, aminoglycoside, amoxicillin, amphotericin, ampicillin, ansamycin, azithromycin, aztreonam, bacillomycin, BAL30072, beta-lactam, biapenem, carbacephalosporins, carbapenem, carbomycin, carbomycin A, carumonam, cefaclor, cefalotin, cephalosporin, cethromycin, chloramphenicol, chlortetracycline, ciprofloxacin, clarithromycin, clindamycin, cycloserine, daptomycin, demeclocycline, dirithromycin, doripenem, doxorubicin, doxycycline, ertapeneme, erythromycin, ethambutol, fluoroquinolone, gentamicin, imipenem, isoniazid, josamycin, kanamycin, kitasamycin, lincomycin, linezolid, loracarbef, macrolide, meropenem, methacycline, midecamycin, monobactam, mupirocin, neomycin, nystatin, oleandomycin, oleandomycin, oxazolidinones, oxytetracycline, panipenem, penem, penicillin, peptide antibiotic, polymixin, pyrrolnitrin, quinolone, rifampin, rifamycins, rolitetracycline, roxithromycin, solithromycin, spiramycin, streptomycin, sulfabenzamide, sulfacetamide, sulfadiazine, sulfadoxine, sulfamerazine, sulfamethazine, sulfamethizole, sulfamethoxazole, sulfisoxazole, sulfonamide, telithromycin, tetracycline, tigimonam, troleandomycin, tylosin, tylocine, vancomycin, or zyvox.

All of the compounds described herein can be easily prepared according to the methods in the Examples herein, or may be prepared according to known techniques in the art of organic synthesis. Many linking groups for conjugating antibiotics to the siderophore and/or linker are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Useful linkers and conjugation techniques that can be used to link antibiotics to Formula (A) are further described by Roosenberg et al.,

*Curr. Med. Chem.* 2000, 7, 159; Wittmann et al., *Bioorg. Med. Chem.* 2002, 10, 1659; and Heinisch et al., *J. Med. Chem.* 2002, 45, 3032. Additional useful reactions well known to those of skill in the art are referenced in March's *Advanced Organic Chemistry Reactions, Mechanisms, and Structure*, 5$^{th}$ Ed. by Michael B. Smith and Jerry March, John Wiley & Sons, Publishers; and Wuts et al. (1999), *Protective Groups in Organic Synthesis*, 3$^{rd}$ Ed., John Wiley & Sons, Publishers. The entire contents of each of these references are hereby incorporated by reference.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and eta-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% by weight of active compound, e.g., the conjugate and/or antibiotic as appropriate. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in water, DMSO, methanol, ethanol, saline, glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, methanol, DMSO, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it may be desirable to administer the active agent to the skin as a composition or formulation, for example, in combination with a dermatologically acceptable carrier, which may be a solid, a liquid, a gel, hydrogel (e.g., keratin hydrogel), mixtures thereof, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Other examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.), the contents of which are hereby incorporated by reference. Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.) the contents of which are hereby incorporated by reference. The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 1 ng/ml to 5 g/ml, which may include 1, 2, 3, 4, 5, 6, 7, 8, 9, 10, 50, 100, 500 ng, 1, 2, 3, 4, 5, 6, 7, 8, 9, 10, 50, 100, 500 m, 1, 2, 3, 4, 5, 6, 7, 8, 9, 10, 50, 100, 500 mg, 1, 2, 3, 4, 5, 6, 7, 8, 9, 10, 50, 100, 500 cg, 1, 2, 3, 4, 5, 6, 7, 8, 9, 10, 50, 100, 500 dg, 1, 2, 3, 4, and 5 g/ml or any combination thereof as appropriate.

Alternatively, the compound may be conveniently administered in a unit dosage form, foe example, containing 5 to 1000 mg/m$^2$, conveniently 10 to 750 mg/m$^2$, most conveniently, 50 to 500 mg/m$^2$ of active ingredient per unit dosage form.

Alternatively, the unit dosage may range from 0.1 mg/kg to 1000 mg/kg, which may include 0.1, 0.5, 1, 2, 3, 4, 5, 10, 20, 50, 75, 100, 200, 250, 300, 350, 400, 500, 700, and 1000 mg/kg, or any combination thereof.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like. The infection can be a bacterial infection, for example, one caused by a bacterium described herein.

The ability of the compound or composition described herein to treat a bacterial infection may be determined by using assays well known to the art. For example, the design of treatment protocols, toxicity evaluation, data analysis, quantification of cell kill, and the biological significance of the use of antibacterial screens are known. In addition, ability of a compound to treat a bacterial infection or kill or inhibit bacteria may be determined using the assays as described herein.

EXAMPLES

In the examples, two different siderophores, desferrioxamine B and a previously reported mixed-ligand siderophore were selected (Scheme 2). Desferrioxamine B, a hydroxamate-containing siderophore, is utilized by a variety of Gram-positive and Gram-negative bacteria and some fungi. The artificial mixed-ligand siderophore containing both catecholate and hydroxamate was designed to use multiple siderophore recognition processes to initiate active transport through the outer membrane of various Gram-negative species. The drug linked to the siderophores was ciprofloxacin, a broad-spectrum fluoroquinolone antibiotic targeting bacterial DNA gyrases and topoisomerases. The syntheses of two siderophore-ciprofloxacin conjugates with the reduction triggered linker is described, together with a study of their biological activity. To assess the feasibility of using the linker in siderophore-drug conjugates, electrochemical and LC-MS studies on linker activation are also reported.

Figure 3:
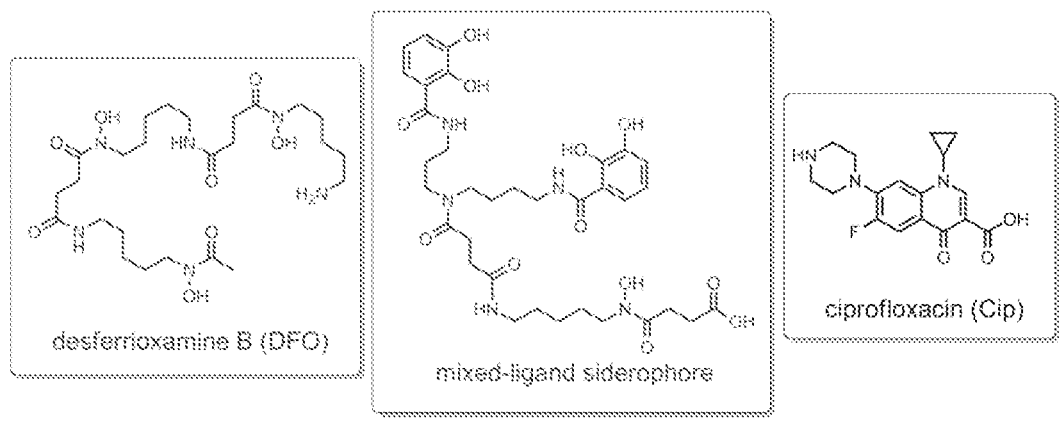
FIG. 3 shows Scheme 2, in which the structures of desferrioxamine B, mixed-ligand siderophore and ciprofloxacin are illustrated.
Figure 4:
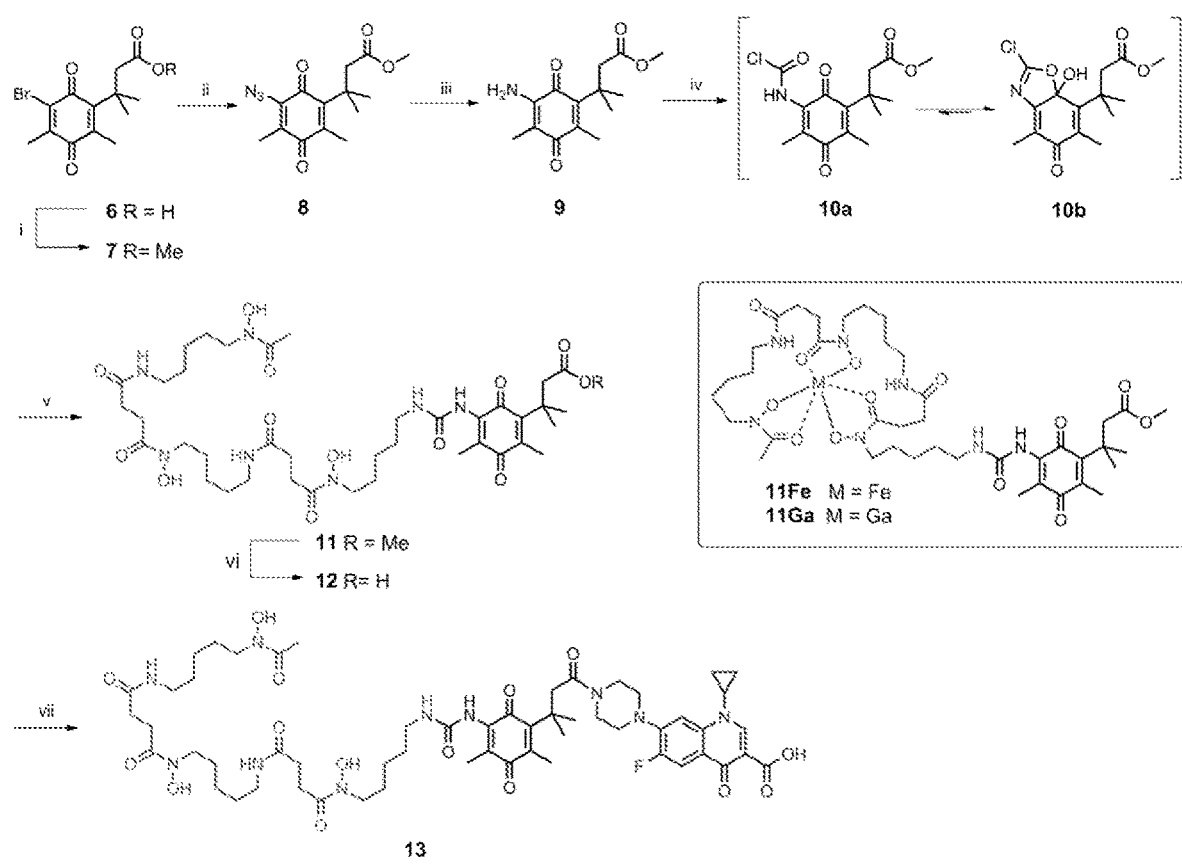
FIG. 4 shows Scheme 3, in which one embodiment of a synthesis of reduction triggered desferrioxamine-ciprofloxacin conjugate 13 is illustrated.
Figure 5:
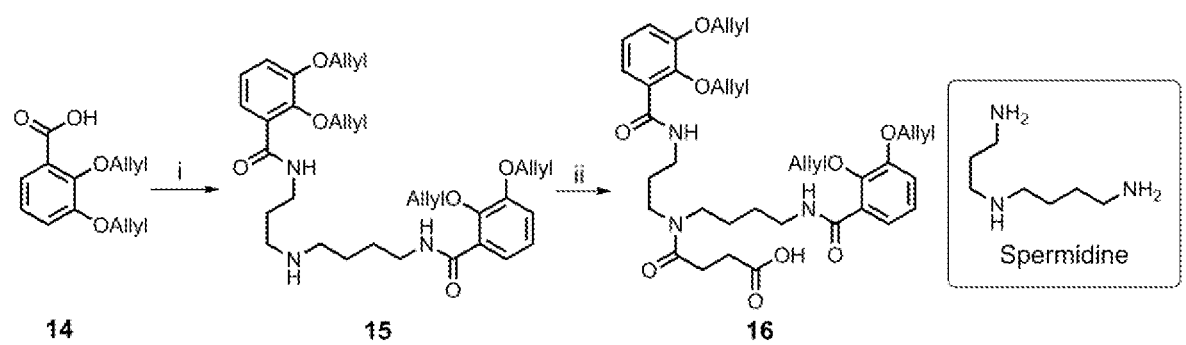
FIG. 5 shows Scheme 4, in which one embodiment of a synthesis of the protected biscatechol siderophore fragment 16 is illustrated.
Figure 6:
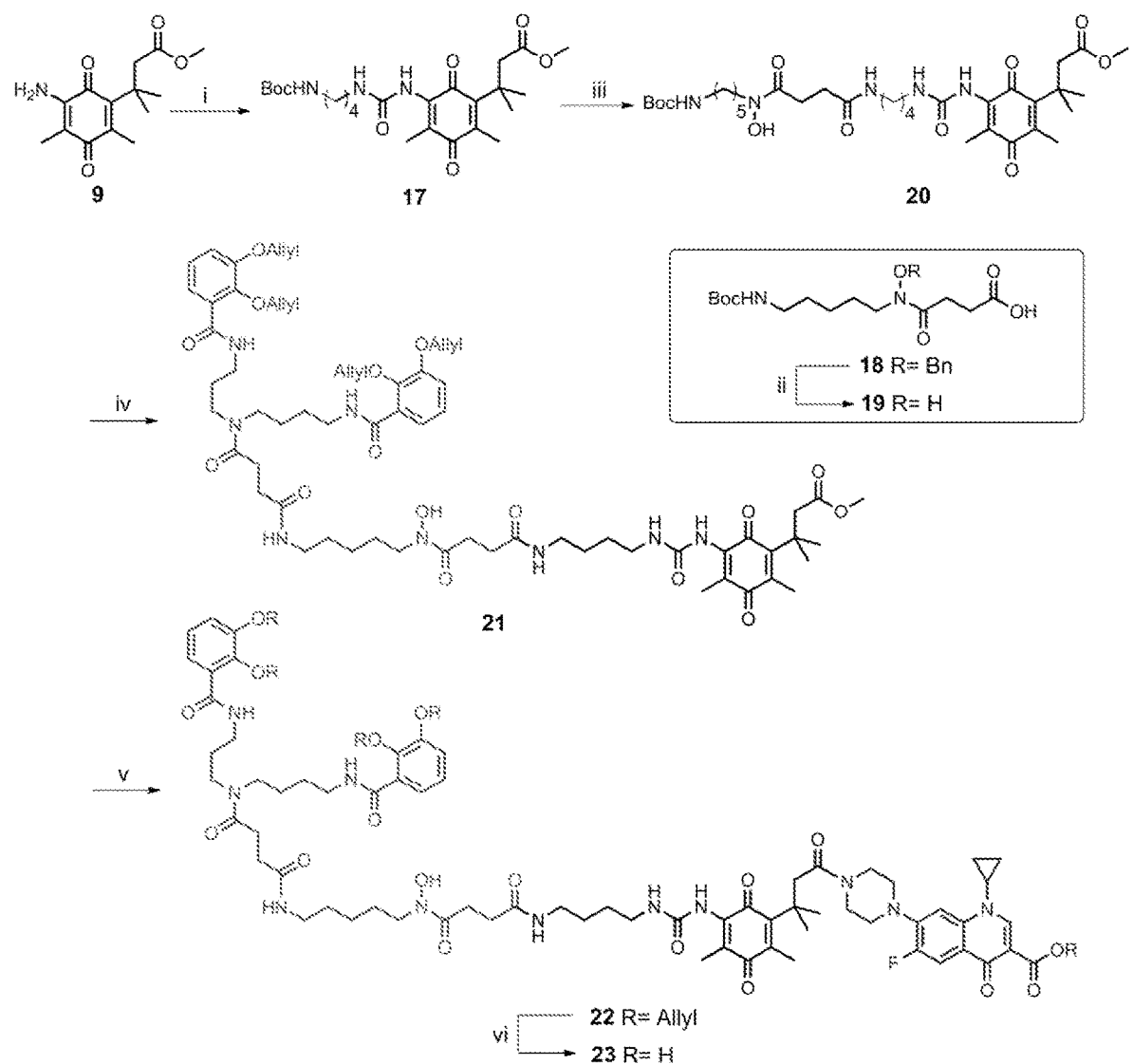
FIG. 6 shows Scheme 5, in which one embodiment of a synthesis of mixed-ligand siderophore-ciprofloxacin conjugate 23 is illustrated.
Figure 7:
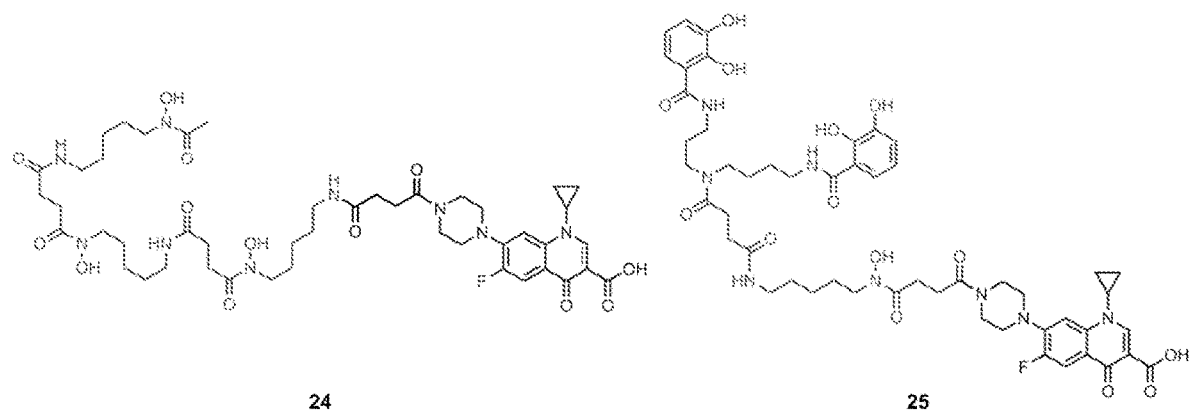
FIG. 7 shows Scheme 6, in which the structures of conventional siderophore-ciprofloxacin conjugates (Desferrioxamine 24 and mixed-ligand siderophore 25) with a stable linker are illustrated.

FIG. 3 shows Scheme 2, with the structures of desferrioxamine B, mixed-ligand siderophore and ciprofloxacin.

Design and Synthesis of Conjugates

To initiate the syntheses of the conjugates, an effective linking strategy to attach siderophores to the reduction triggered linker is shown. A urea linkage was chosen for its appreciable stability and synthetic accessibility. Therefore, synthesis of the desferrioxamine conjugate (Scheme 3) started with bromo acid 6 which was conveniently converted to its methyl ester 7 using thionyl chloride in methanol. Nucleophilic substitution of 7 with $NaN_3$ in aqueous methanol provided azide 8 in excellent yield. The azide was converted to vinylogous amide 9 in 66% yield by a triphenylphosphine-mediated reduction. Treatment of 9 with excess phosgene in toluene afforded an unstable intermediate with a proposed carbamoyl chloride structure 10a. Interestingly, proton and carbon NMR suggest that the intermediate predominantly existed in a chloro oxazoline structure 10b, probably due to the electron deficiency of the quinone unit which induces the intramolecular addition. Addition of desferrioxamine to intermediate 10 in the presence of triethylamine gave ester 11 with a urea linkage between the siderophore and the linker. Subsequent hydrolysis of the ester and coupling the resulting acid 12 with ciprofloxacin using EDC and HOBt produced the desferrioxamine-ciprofloxacin conjugate 13 in moderate yield.

Scheme 3. Synthesis of reduction triggered desferrioxamine-ciprofloxacin conjugate 13. Reagents and conditions: (i) $SOCl_2$, MeOH, reflux, 77%; (ii) $NaN_3$, MeOH—$H_2O$, rt, 91%; (iii) 1. $PPh_3$, $CH_2Cl_2$, rt; 2. AcOH, THF-$H_2O$, reflux, 66%; (iv) 1. $COCl_2$, toluene, rt; (v) Desferrioxamine mesylate, $Et_3N$, DMF, 0° C.-rt, 74% for 2 steps; (vi) LiOH, MeOH—$H_2O$, rt, 90%; (vii) ciprofloxacin, EDC, HOBt, $Et_3N$, DMAP, $CH_2Cl_2$, 0° C.-rt, 60%

Synthesis of the mixed-ligand siderophore-ciprofloxacin conjugate started with preparation of the biscatechol fragment 16 (Scheme 4). Selective acylation of the primary amino groups of spermidine with 2,3-diallyloxybenzoic acid 14 was achieved by using N,N'-carbonyldiimidazole (CDI) as the activating reagent to give bis-acylated spermidine 15 in 87% yield. Treatment of amine 16 with succinic anhydride and catalytic amount DMAP generated acid 16 in 74% yield.

Scheme 4. Synthesis of the protected biscatechol siderophore fragment 16. Reagents and conditions: (i) CDI, spermidine, $CH_2Cl_2$, 0° C.-rt, 87%; (ii) Succinic anhydride, DMAP, pyridine, 95° C., 74%

Since the carboxylic acid terminus in the mixed-ligand siderophore is not compatible with the chemistry of forming the urea linkage, an additional diamine spacer is needed. Therefore, using the same methodology, N-Boc-1,4-butanediamine was connected with vinylogous amide 9 via a urea linkage, providing compound 16 in 91% yield (Scheme 5). After removal of the Boc protecting group using trifluoroacetic acid, the resulting amine was coupled with acid 18, which is the part of the mixed-ligand siderophore, to afford compound 19 in 50% yield. Using similar procedure, the Boc protecting group in compound 19 was cleaved and the resulting amine was coupled with acid 15, to yield methyl ester 20. Subsequent hydrolysis of the ester and coupling the resulting acid with O-allylciprofloxacin afforded the fully protected conjugate 21. Pd(O)-mediated global deallylation of 21 furnished the mixed-ligand siderophore-ciprofloxacin conjugate 22 in moderate yield.

Scheme 5. Synthesis of mixed-ligand siderophore-ciprofloxacin conjugate 23. Reagents and conditions: (i) 1. $COCl_2$, toluene, rt; 2. N-Boc-1,4-butanediamine, $Et_3N$, $CH_2Cl_2$, 0° C.-rt, 91%; (ii) $H_2$, Pd/C, MeOH, rt, 99%; (iii) 1. TFA, $CH_2Cl_2$, 0° C.-rt; 2. Acid 19, EDC, HOBt, $Et_3N$, DMAP, $CH_2Cl_2$, 0° C.-rt, 50%; (iv) 1. TFA, $CH_2Cl_2$, 0° C.-rt; 2. Acid 16, EDC, HOBt, $Et_3N$, DMAP, $CH_2Cl_2$, 0° C.-rt, 43%; (v) 1. LiOH, MeOH—$H_2O$, 0° C.-rt; 2. O-Allylciprofloxacin, EDC, HOBt, $Et_3N$, DMAP, $CH_2Cl_2$, 0° C.-rt, 55%; (vi) $Pd(PPh_3)_4$, sodium benzenesulfinate, AcOH, THF-MeOH, rt, 48%.

In parallel, we also synthesized desferrioxamine and mixed-ligand siderophore ciprofloxacin conjugates (Desferrioxamine 24 and mixed-ligand siderophore 25) with a stable succinic linker as two controls to be included in the biological assays (Scheme 6).

Electrochemical and LC-MS studies

FIG. 8. Cyclic votammograms of 11Fe (FIG. 8A, 2 mM) and 11Ga (FIG. 8B, 2 mM). Conditions: platinum working electrode; platinum wire auxiliary electrode; saturated calomel electrode (SCE) reference electrode; 0.1 M KCl as the background electrolyte in 0.05 M phosphate buffer pH 7.0 at ambient temperature; scan rate=100 mV $s^{-1}$.

To assess whether the quinone "trimethyl lock" linker in conjugates 13 and 23 is activated by reduction, the reduction potential of the quinone "trimethyl lock" linker was studied. Two model compounds 11Fe and 11Ga were synthesized from compound 11 with the corresponding metal salts and subjected to cyclic voltammetry study. The voltammograms of both complexes (FIG. 8) show only one irreversible reduction peak, consistent with the literature report for other quinone "trimethyl lock" analogs.[30-31] At pH 7, 11Fe and 11Ga display identical reduction peak potential ($E_p$=-412 mV vs. SCE or -168 mV vs. NHE), demonstrating that they are thermodynamically reducible by common biological reductants such as NAD(P)H.[10] 11Ga, of which the metal center is redox-inert within the experimental potential window, has the same reduction potential as 10Fe, suggesting that the measured potential attributes to quinone reduction solely. The absence of an Fe(III) reduction wave of 10Fe also indicates that the reduction of the quinone unit is thermodynamically easier than the siderophore-chelated Fe(III).

Figure 9:
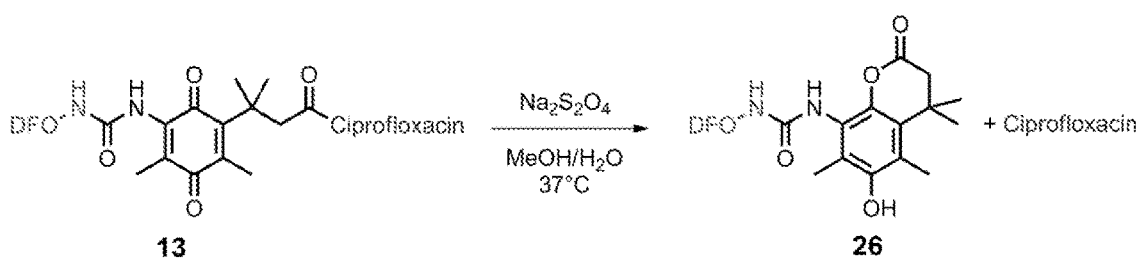
FIG. 9 shows LC-MS data of the chemical reduction of conjugate 13.
Figure 9:
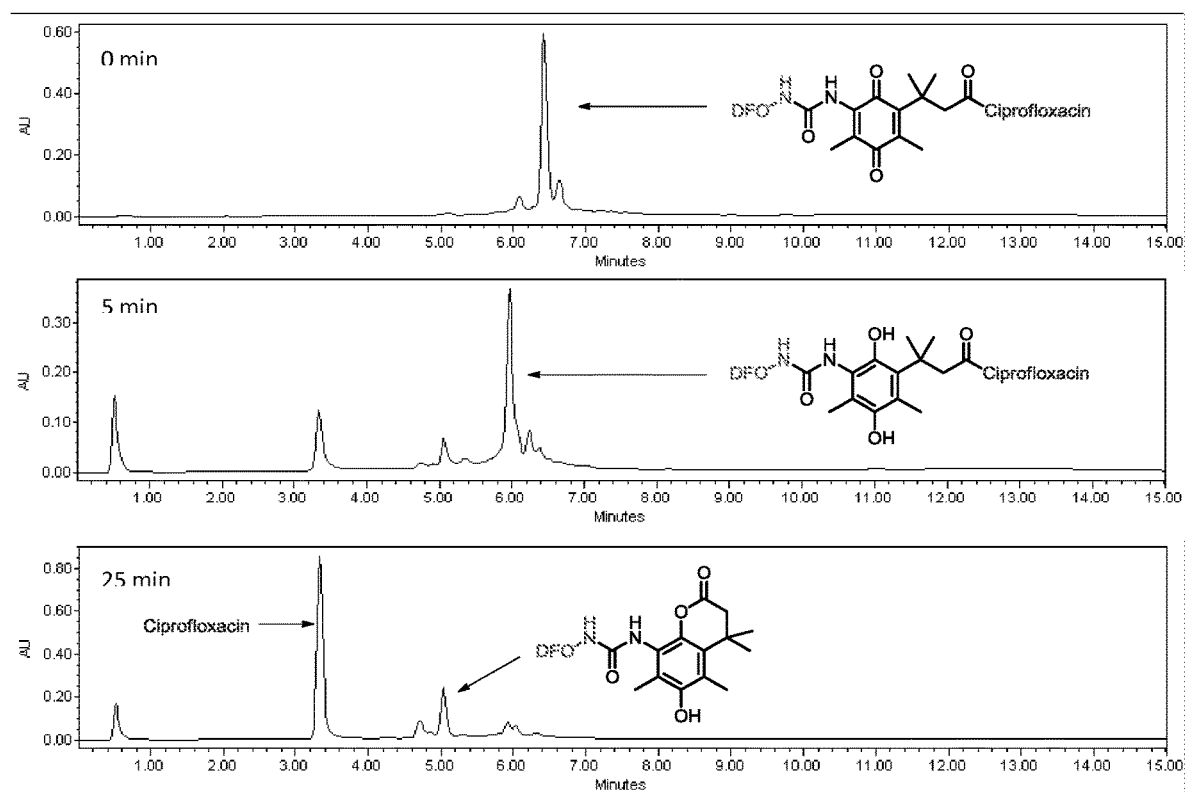

In order to examine whether the quinone "trimethyl lock" in the synthesized conjugates would release the antibiotic under mild reduction conditions, conjugate 13 was treated with ~20-fold excess of sodium dithionite ($Na_2S_2O_4$) and the mixture was incubated at 37° C. The reaction progress was monitored by LC-MS (FIG. 9). HPLC chromatograph and ESI-MS analysis showed that after 5 min the peak of the conjugate [$(M+H)^+$=1152.37] was largely diminished while the hydroquinone intermediate [$(M+H)^+$=1154.22] which has some life-time was the predominant species. Meanwhile the lactone 26 [$(M+H)^+$=822.85] as proposed and the released ciprofloxacin [$(M+H)^+$=332.18] also started to appear and complete release of the ciprofloxacin was achieved after 25 min. This result clearly showed that ciprofloxacin can be cleaved within a short time range after the linker is activated by reduction. The results of electrochemical study and chemical reduction in combination demonstrated the feasibility of using quinone "trimethyl lock" as a reduction triggered drug release linker in siderophore-antibiotic conjugates.

Biological Studies

The siderophore-ciprofloxacin conjugates 13 and 23 were first evaluated for their ability to inhibit the growth of bacteria using the agar well diffusion test. Representative Gram-positive strains included *Bacillus subtilis, Staphylococcus aureus* and *Micrococcus luteus*. The Gram-negative strains studied included *Pseudomonas aeruginosa* (a wild type K799/wt and a penetration mutant strain K799/61), *Escherichia coli*, and *Acinetobacter baumannii*. The parent drug ciprofloxacin and conjugate 24 and 25 with a stable succinic linker were also included in the assay as controls.

The results of assays for antibacterial activity of the four conjugates are summarized in Table 1. At the same concentration (0.2 mM), conjugates with the quinone "trimethyl pared the parent drug ciprofloxacin. This is possibly due to 1) bacterial recognition of the chemically modified siderophore is affected; 2) activation efficiency of the linker is low inside the bacteria. Further investigation by attaching siderophores with better recognition to the linker could provide conjugate with stronger activities. An artificial triscatecholate sideophore with linker attachment site remote from the site of iron binding is a promising candidate. Improvement of the linker's activation efficiency might be achieved by introducing electron-withdrawing groups to the quinone moiety (e.g. replacing $-CH_3$ with $-CF_3$) to further increase its electron deficiency although it could be more synthetic challenging. Accordingly, in one embodiment, one or more methyl groups on the Q may be replaced with trifluoromethyl groups.

TABLE 1

Diameter of growth inhibition zones (mm) in the agar diffusion antibacterial susceptibility assay.

| | Gram-positive bacteria | | | Gram-negative bacteria | | | |
|---|---|---|---|---|---|---|---|
| | B. subtilis | S. aureus | M. luteus | P. aeruginosa | | E. coli | A. baumannii |
| Compds | ATCC 6633 | SG 511 | ATCC 10240 | K799/wt | K799/61 | X580 | ATCC 17961[a] |
| Ciprofloxacin | 28[c] | 28[b] | 12P[b] | 21[c] | 24/32p[c] | 31[d] | 15p[b] |
| 13 | 34 | 25 | 14 | 27/31P | 31/46P | 34/38P | NT |
| 24 | 26 | 22 | 0 | 18P | 19/26P | 32/39P | NT |
| 23 | 20/26p | 13P | 0 | 19 | 19/26p | 27 | 20 |
| 25 | 0 | 0 | 0 | 14 | 0 | 21 | 18 | p, partially clear inhibition zone/colonies in the inhibition zone;

P, unclear inhibition zone/many colonies in the inhibition zone;

NT, not tested

Exactly 50 μL of a 0.2 mM solution of each compound dissolved in 1:9 DMSO/MeOH was filled in 9 mm wells in agar media (Standard I Nutrient Agar, Serva or Mueller Hinton II Agar, Becton, Dickinson and Company). Inhibition zones read after incubation at 37° C. for 24 h.

[a]*A. baumannii* was tested in the presence of 100 μM of 2,2'-bipyridine.

Figure 11:
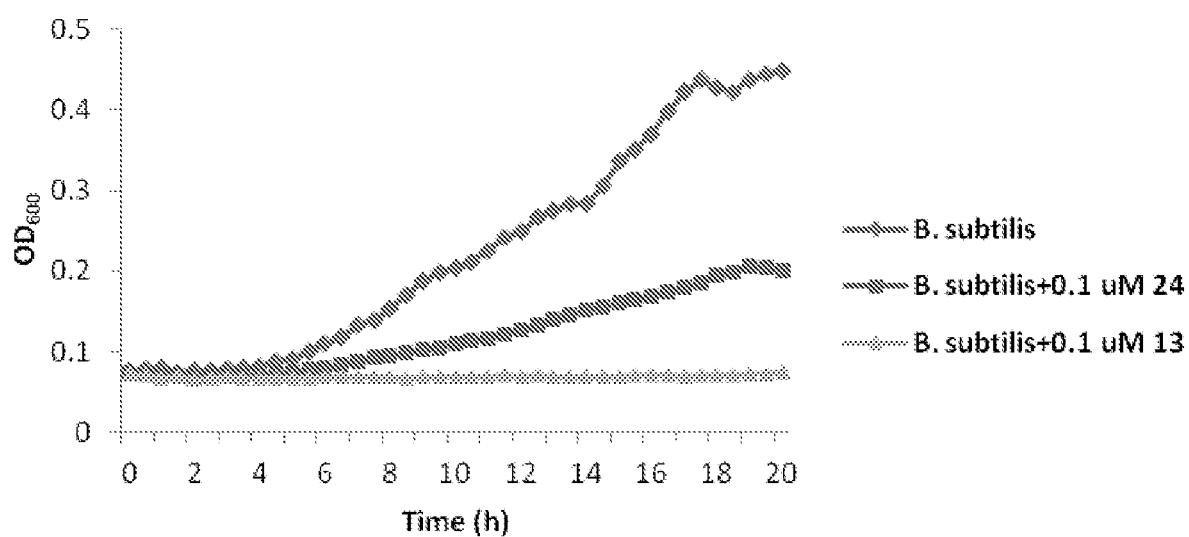
FIG. 11 shows a growth curve of *B. subtilis* in the presence of conjugates 13 and 24 under iron deficient condition.
Figure 12C:
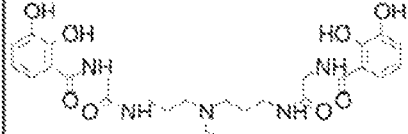
FIG. 12 shows a list of embodiments of siderophores.
Figure 12C:
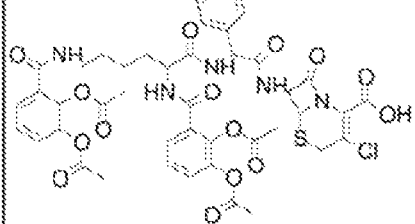
Figure 12C:
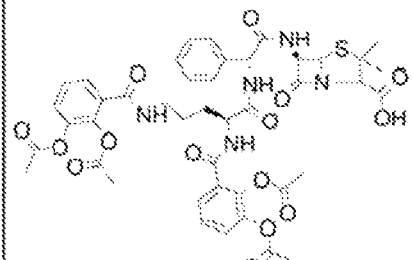
Figure 12C:
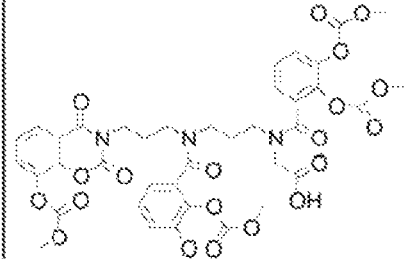
Figure 12D:
Figure 12D:
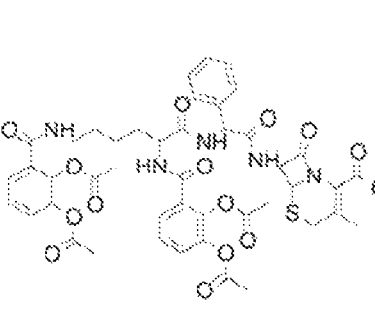
Figure 12D:
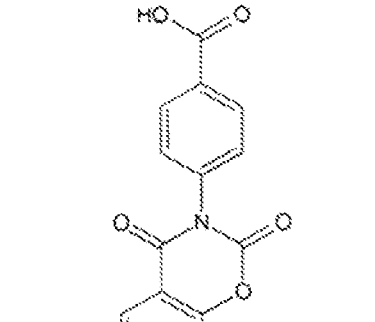
Figure 12D:
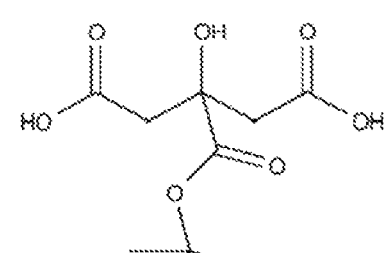
Figure 12G:
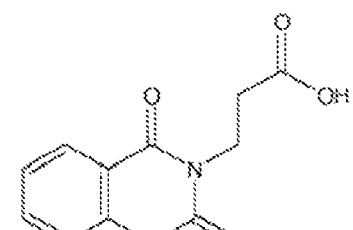
Figure 12G:
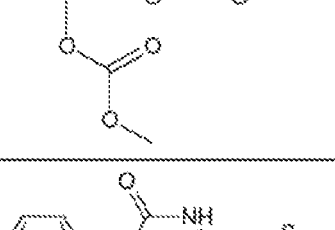
Figure 12G:
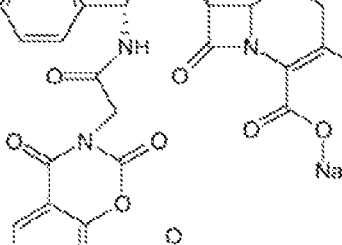
Figure 12G:
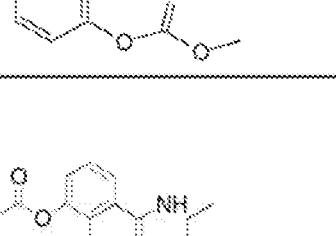
Figure 12H:
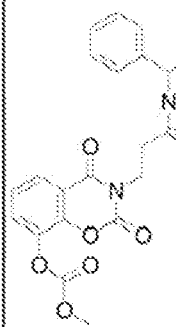
Figure 12H:
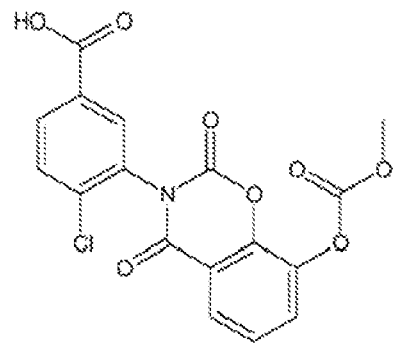
Figure 12H:
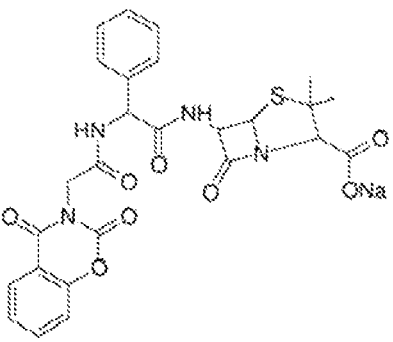
Figure 12H:
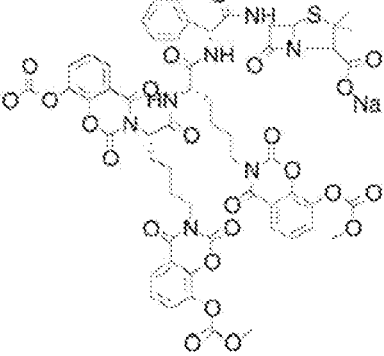
Figure 12I:
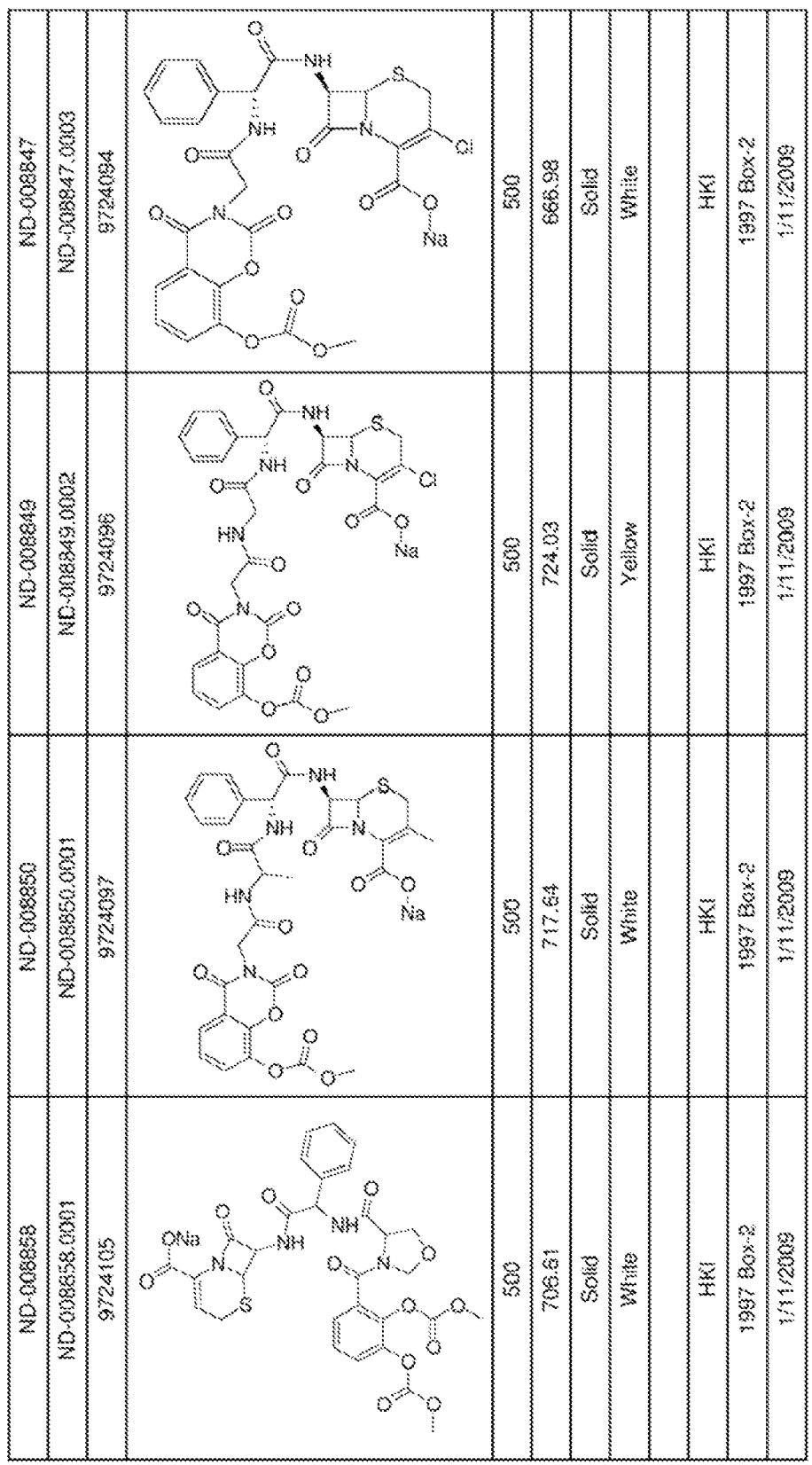
Figure 12J:
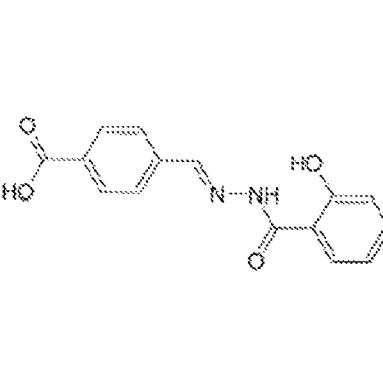
Figure 12J:
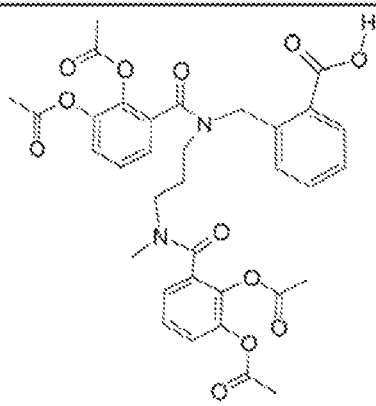
Figure 12J:
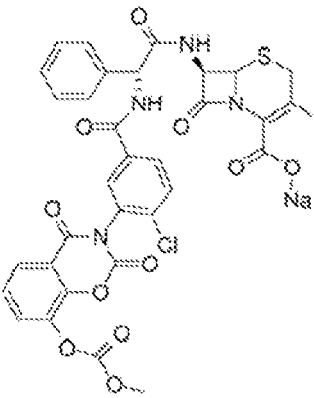
Figure 12J:
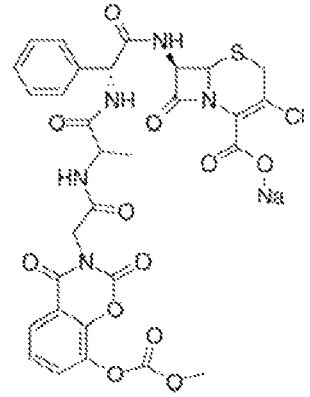
Figure 12K:
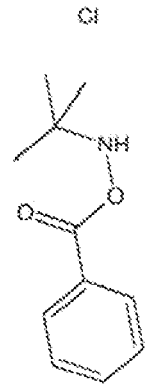
Figure 12K:
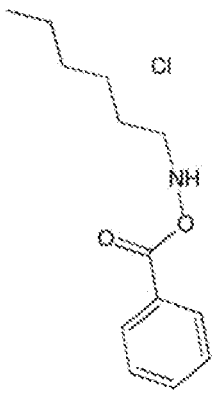
Figure 12K:
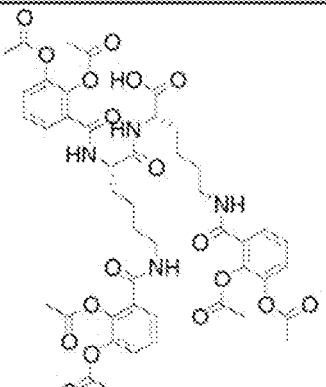
Figure 12K:
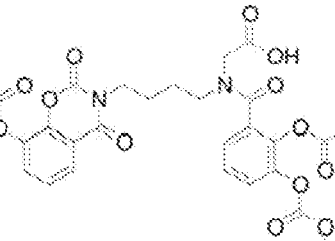
Figure 12M:
Figure 12M:
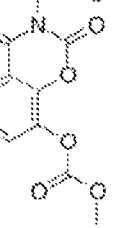
Figure 12M:
Figure 12M:
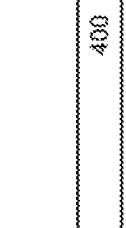
Figure 12N:
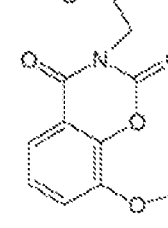
Figure 12N:
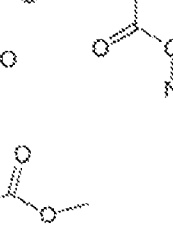
Figure 12N:
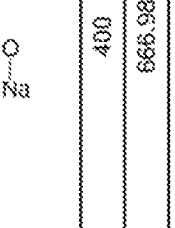
Figure 12N:
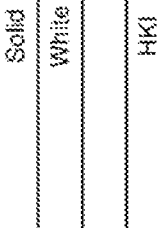
Figure 12P:
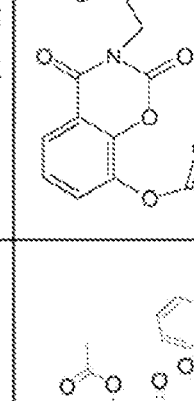
Figure 12P:
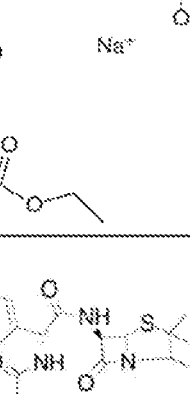
Figure 12P:
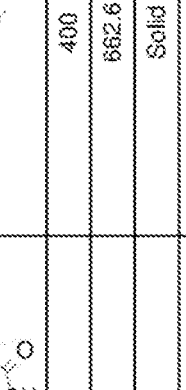
Figure 12P:
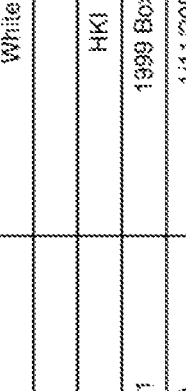
Figure 12R:
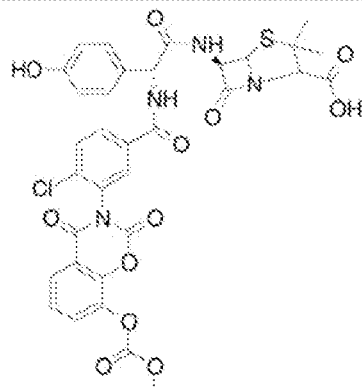
Figure 12R:
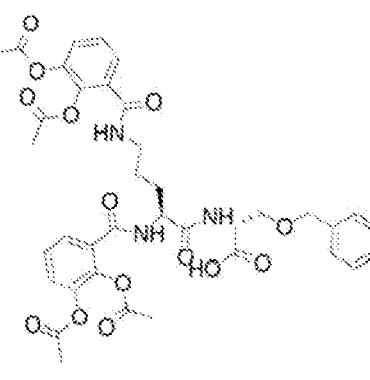
Figure 12R:
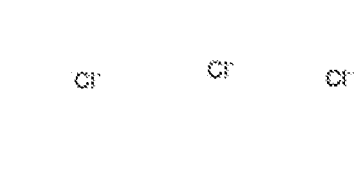
Figure 12R:
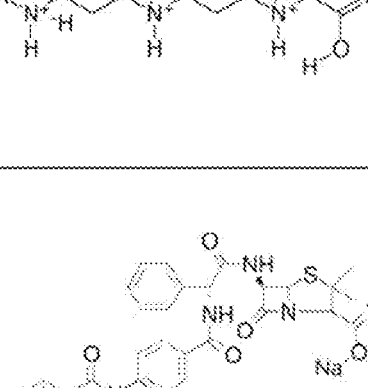
Figure 12T:
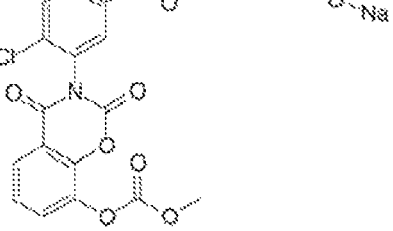
Figure 12T:
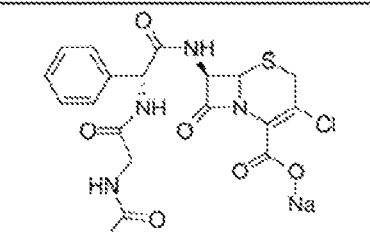
Figure 12T:
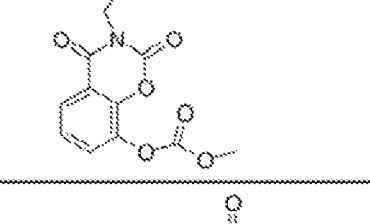
Figure 12T:
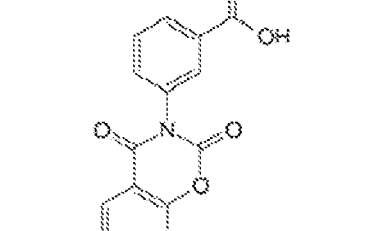
Figure 12V:
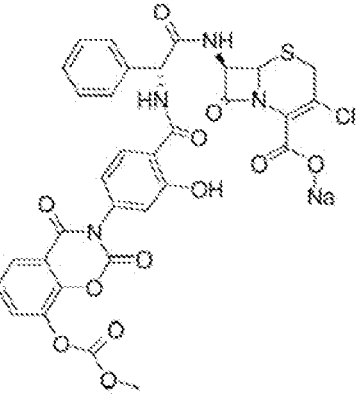
Figure 12V:
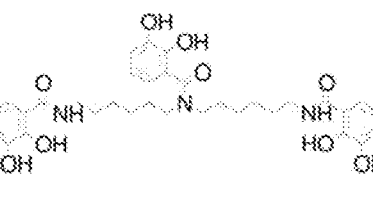
Figure 12V:
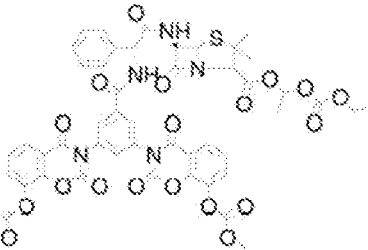
Figure 12V:
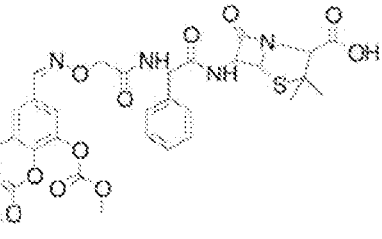
Figure 12X:
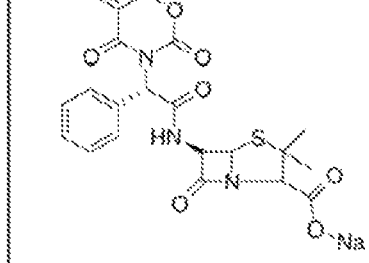
Figure 12X:
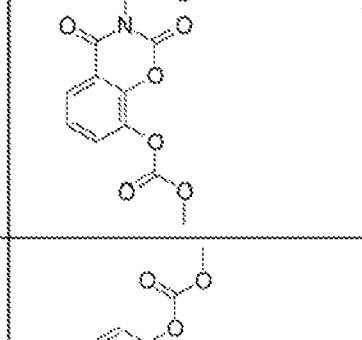
Figure 12X:

Figure 12X:

Figure 12Y:
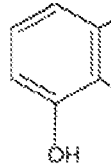
Figure 12Y:
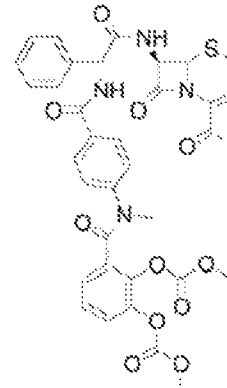
Figure 12Y:
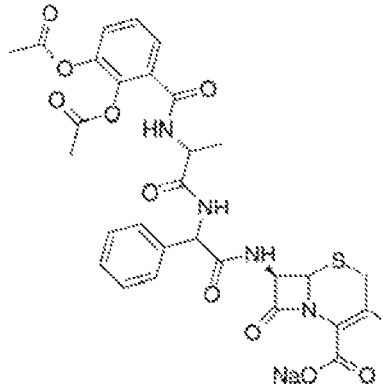
Figure 12Y:
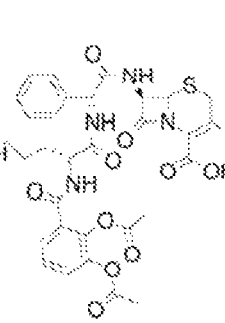
Figure 12Z:
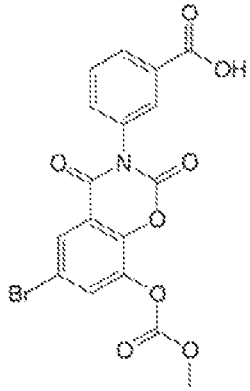
Figure 12Z:
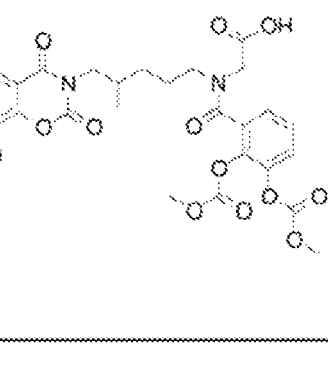
Figure 12Z:
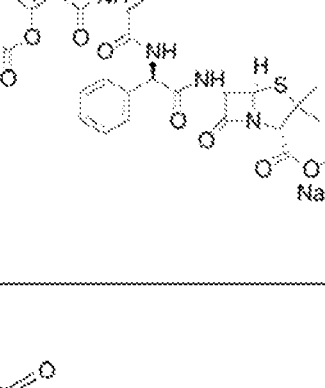
Figure 12Z:
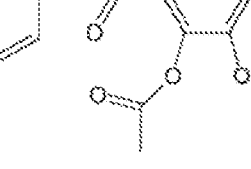
Figure 12A:
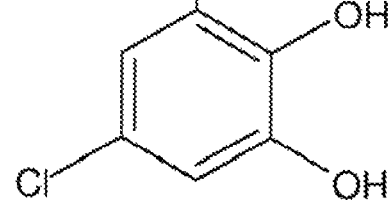
Figure 12A:
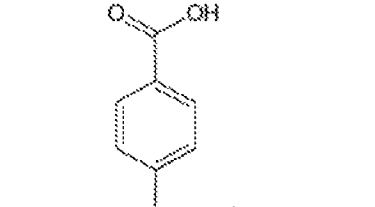
Figure 12A:
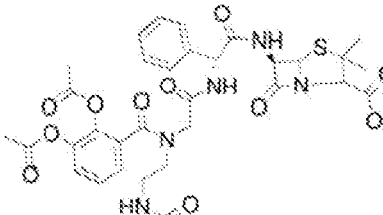
Figure 12A:
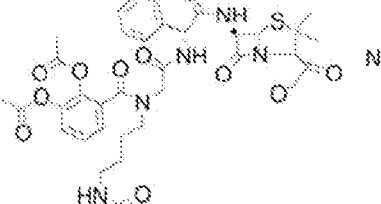
Figure 12A:
Figure 12A:
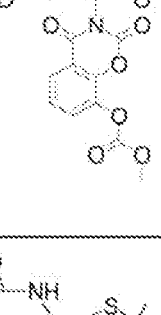
Figure 12A:
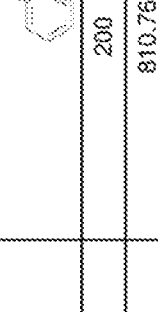
Figure 12A:
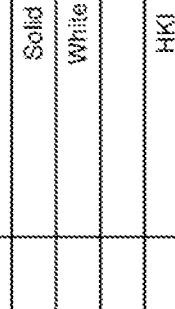
Figure 12A:
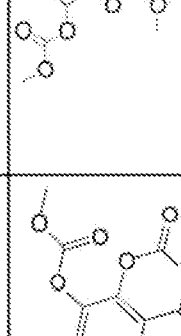
Figure 12A:
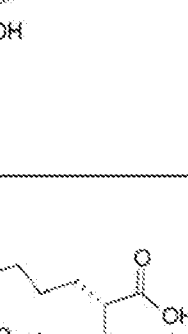
Figure 12A:
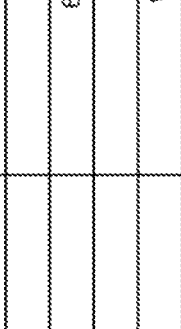
Figure 12A:
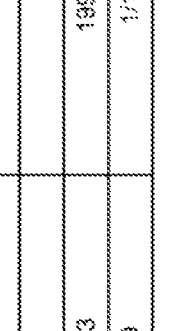
Figure 12A:
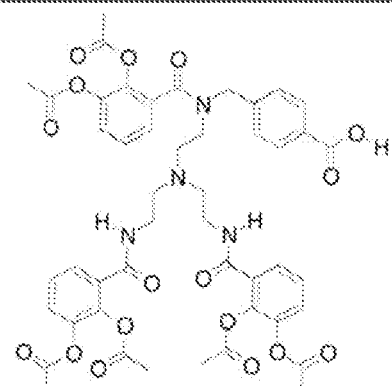
Figure 12A:

Figure 12A:

Figure 12A:

Figure 12A:

Figure 12A:

Figure 12A:
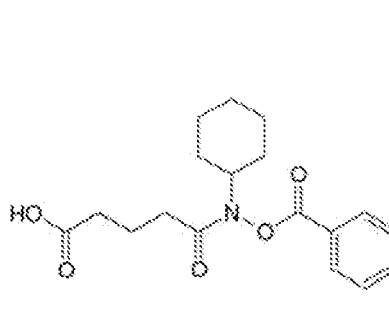
Figure 12A:
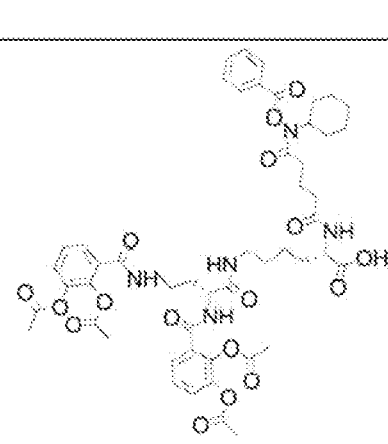
Figure 12A:
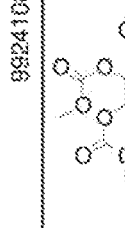
Figure 12A:
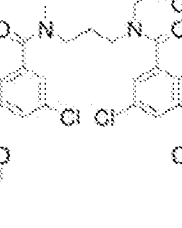
Figure 12A:

Figure 12A:

Figure 12A:
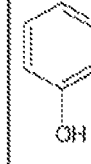
Figure 12A:

Figure 12A:

Figure 12A:

Figure 12A:
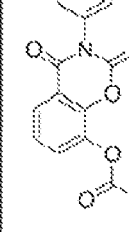
Figure 12A:
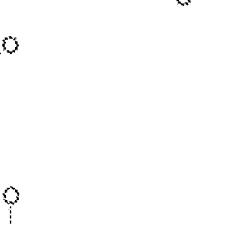
Figure 12A:
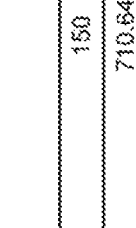
Figure 12A:
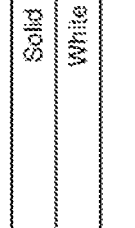
Figure 12A:
Figure 12A:
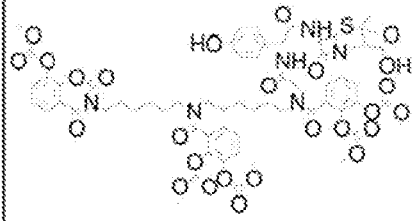
Figure 12A:
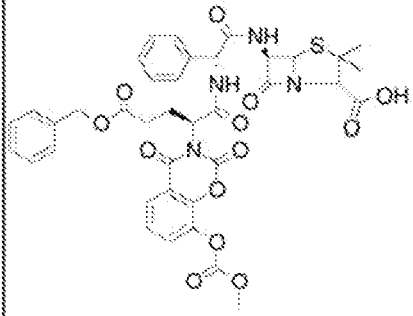
Figure 12A:
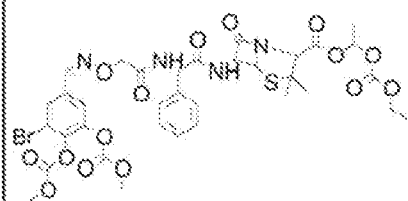
Figure 12A:
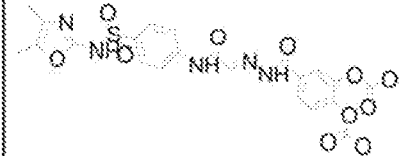
Figure 12A:
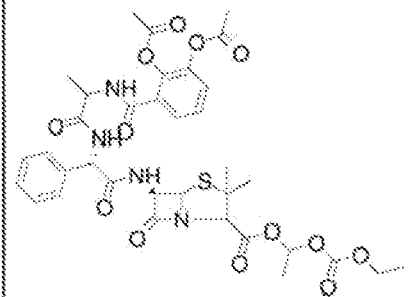
Figure 12A:
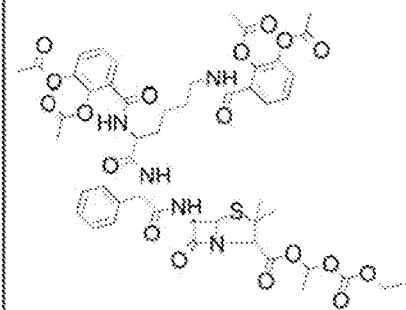
Figure 12A:
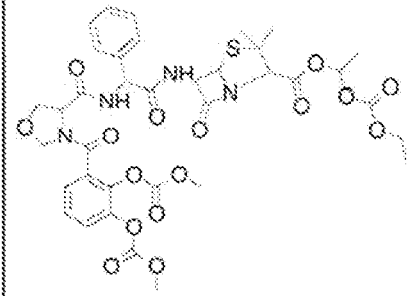

[b, c, d]Ciprofloxacin was tested at (a) 5 μg/mL, (b) 1.66 μg/mL, (c) 0.33 μg/mL in $H_2O$.

lock" linker (13 and 23) displayed stronger activity than their counterparts (24 and 25, respectively) with a non-releasable succinic linker in all cases, as indicated by the larger inhibition zones. A further kinetic study also showed that conjugate 13 was more potent than 24 at the same concentration (0.1 μM) in inhibiting growth of *B. subtilis* (FIG. 11). It is reasonable to assume that, if recognized by the microbial siderophore receptor, 13 and 24, 23 and 25 are transported at similar rates as they possess similar molecular shape and topology. The results therefore suggest that the "trimethyl lock" facilitated drug release process occurred after the conjugate being transported. Also notable is that mixed-ligand conjugates 23 and 25 showed a narrower spectrum of activity (Gram-negative) relative to the desferrioxamine conjugates, which is consistent with previous observations.[26-28] Although the anticipated drug release process might happen, all four conjugates are less active com- FIG. 11 shows a growth curve of *B. subtilis* in the presence of conjugates 13 and 24 under iron deficient conditions.

Desferrioxamine conjugate 13 was also tested for its antibacterial activity against a panel of ESKAPEE[2] bacteria by determining their minimum inhibitory concentrations (MIC) using the broth microdilution assay (Table 2). Conjugate 13 displayed moderate to good antibacterial activity (0.5-32 μM) against all the strains except *E. faecium*, against which ciprofloxacin is only moderately active (8 μM). In all the strains tested, conjugate 13 showed reduced activities compared to the free drug ciprofloxacin, which is consistent with the trend observed in the agar diffusion assay. The reduced activity of conjugate compared to the parent drug again suggests that the siderophore recognition after incorporation of linker and linker activation efficiency needs further optimization.

TABLE 2

MIC values of conjugate 13 and ciprofloxacin against ESKAPEE panel of bacteria.

| | MIC(μM) Against ESKAPEE Test Organisms[a, b] | | | | | | |
|---|---|---|---|---|---|---|---|
| Compds | E. faecium NCTC 7171 | S. aureus ATCC 29213 | K. pneunonia ATCC 700603 | A. baumanii ATCC 17961 | P. aeruginosa ATCC 27853 | E. aerogenes ATCC 35029 | E. coli ATCC 25922 |
| 13 | 32-128 | 4 | 32 | 8 | 4 | 2 | 0.5 |
| Ciprofloxacin | 8 | NT | 0.25 | 0.25 | 0.125 | <0.015 | <0.015 |

[a]MIC values (μM) were determined using the broth microdilution method in Müller-Hinton broth No. 2 (MHII) with visual end point analysis according to the CLSI guidelines.[33]
[b]Each compound was tested in triplicate.
NT, not tested.

Comparative Data

Figure 10:
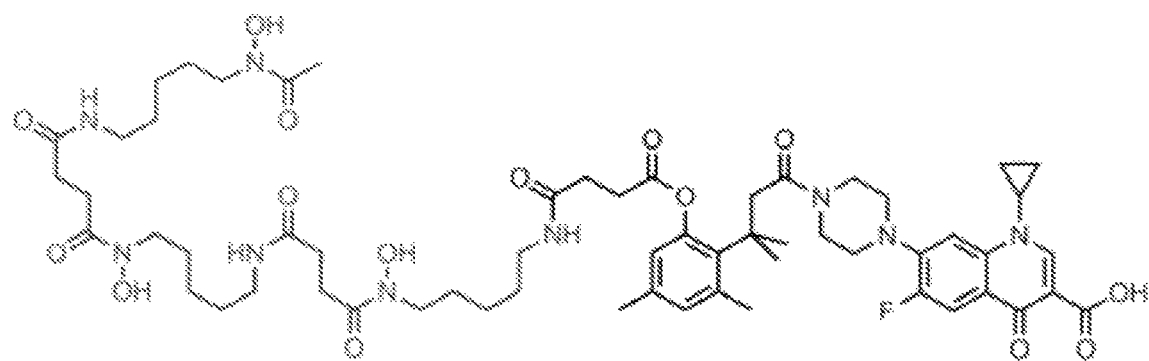
FIG. 10 shows comparative compounds 1 (potential esterase triggered desferrioxamine-ciprofloxacin conjugate) and 2 (potential phosphatase triggered desferrioxamine-ciprofloxacin conjugate).
Figure 10:
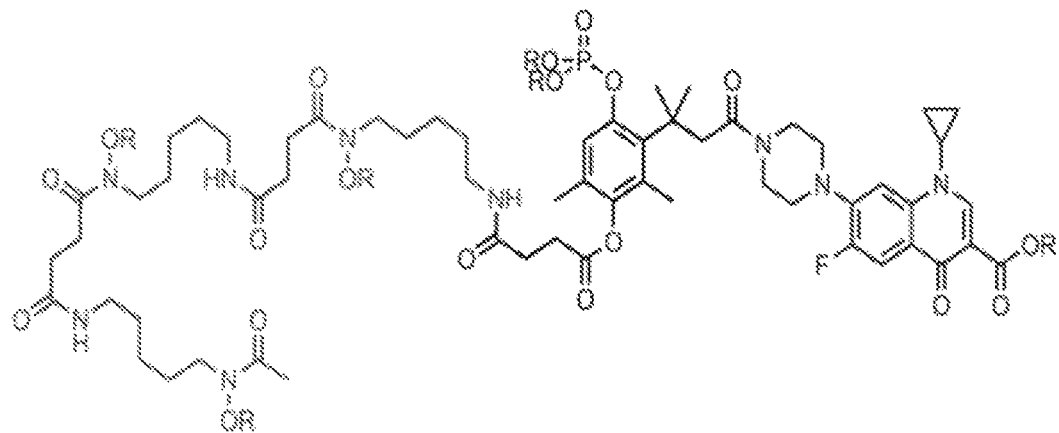

Comparative data was obtained using comparative compounds, Comp 1 and Comp 2, which are shown in FIG. 10. The comparative data is shown in Tables 3 and 4.

TABLE 3

Comparative Data
Diameter of growth inhibition zones (mm) in the agar diffusion antibacterial susceptibility assay for comparative compounds Comp 1 and Comp 2.

| | Gram-positive bacteria | | | Gram-negative bacteria | | |
|---|---|---|---|---|---|---|
| | Bacillus subtilis | Staphylococcus aureus | Micrococcus luteus ATCC | Pseudomonas aeruginosa | | Escherichia coli |
| Compds | ATCC 6633 | SG 511 | 10240 | K799/wt | K799/61 | X580 |
| Comp 1 | 26 | 16 | 0 | 26 | 27/37p | 29 |
| Comp 2 | 0 | 0 | 0 | 0 | 0 | 21 | p, partially clear inhibition zone/colonies in the inhibition zone
Exactly 50 μL, of a 0.2 mM solution of each compound dissolved in 1:9 DMSO/MeOH was filled in 9 mm wells in agar media (Standard I Nutrient Agar, Serva or Mueller Hinton II Agar, Becton, Dickinson and Company). Inhibition zones read after incubation at 37° C. for 24 h.

TABLE 4

Comparative Data
MIC values of comparative compound Comp 1 against ESKAPEE panel of bacteria.

| | MIC (μM) Against ESKAPEE Test Organisms[a, b] | | | | | | |
|---|---|---|---|---|---|---|---|
| Compds | E. faecium NCTC 7171 | S. aureus ATCC 29213 | K. pneunonia ATCC 700603 | A. baumanii ATCC 17961 | P. aeruginosa ATCC 27853 | E. aerogenes ATCC 35029 | E. coli ATCC 25922 |
| Comp 1 | >128 | 32 | 16 | 8 | 8 | 1 | 1 |

[a]MIC$_{90}$ values (μM) were determined using the broth microdilution method in Mueller-Hinton broth No. 2 (MHII) with visual end point analysis according to the CLSI guidelines.
[b]Each compound was tested in triplicate.

Two siderophore-ciprofloxacin conjugates with a potential reduction triggered linker for drug release were synthesized. The linker incorporated in the conjugates was designed to be activated by taking advantage of the reductive pathway of bacterial iron metabolism. Upon reduction, a rapid "trimethyl lock" facilitated lactonization would release the antibiotic in the conjugate. Electrochemical studies indicated that the quinone moiety in the linker is thermodynamically reducible by common biological reductants and the expected lactonization happens within a short time range with concomitant release of the drug as supported by LC-MS analysis. Furthermore, conjugates with the reduction triggered linker were more potent in antibacterial assays compared to their counterparts with the stable linker, which suggests the drug release occurs inside the bacterial cells. However, the activity of conjugates 13 and 23 was weaker than that of the parent drug ciprofloxacin, suggesting that either the siderophore recognition or linker activation efficiency or both factors requires further optimization. Once optimized, the efficient synthetic strategy developed for attaching siderophores to the quinone "trimethyl lock" linker via a urea linkage can and will be used in the development of new generation of siderohpore-drug conjugates with a drug release linker.

The entire contents of each of the following references are incorporated herein by reference.

Spellberg, B., Guidos, R., Gilbert, D., Bradley, J., Boucher, H. W., Scheld, W. M., Bartlett, J. G., and Edwards, J. (2008) The epidemic of antibiotic-resistant infections: a call to action for the medical community from the Infectious Diseases Society of America, Clin. Infect. Dis. 46, 155-164.

Boucher, H. W., Talbot, G. H., Bradley, J. S., Edwards, J. E., Gilbert, D., Rice, L. B., Scheld, M., Spellberg, B., and Bartlett, J. (2009) Bad bugs, no drugs: no ESKAPE! An update from the Infectious Diseases Society of America, Clin. Infect. Dis. 48, 1-12.

Projan, S. J. (2003) Why is big Pharma getting out of antibacterial drug discovery?, Curr. Opin. Microbiol. 6, 427-430.

Levy, S. B., and Marshall, B. (2004) Antibacterial resistance worldwide: causes, challenges and responses, Nat. Med. 10, S122-S129.

Pages, J. M., James, C. E., and Winterhalter, M. (2008) The porin and the permeating antibiotic: a selective diffusion barrier in Gram-negative bacteria, Nat. Rev. Microbiol. 6, 893-903.

Fernandez, L., and Hancock, R. E. W. (2012) Adaptive and mutational resistance: role of porins and efflux pumps in drug resistance, Clin. Microbiol. Rev. 25, 661-681.

Möllmann, U., Heinisch, L., Bauernfeind, A., Köhler, T., and Ankel-Fuchs, D. (2009) Siderophores as drug delivery agents: application of the "Trojan Horse" strategy, Biometals 22, 615-624.

Ji, C., Juárez-Hernández, R. E., and Miller, M. J. (2012) Exploiting bacterial iron acquisition: siderophore conjugates, Future Med. Chem. 4, 297-313.

Budzikiewicz, H. (2001) Siderophore-antibiotic conjugates used as trojan horses against Pseudomonas aeruginosa, Curr. Top. Med. Chem. 1, 73-82.

Harrington, J. M., and Crumbliss, A. L. (2009) The redox hypothesis in siderophore-mediated iron uptake, Biometals 22, 679-689.

Braun, V., Günthner, K., Hantke, K., and Zimmermann, L. (1983) Intracellular activation of albomycin in Escherichia coli and Salmonella typhimurium, J. Bacteria 156, 308-315.

Braun, V., Pramanik, A., Gwinner, T., Koberle, M., and Bohn, E. (2009) Sideromycins: tools and antibiotics, Biometals 22, 3-13.

Möllmann, U., Dong, L., Vértesy, L., and Miller, M. J. (2004) Salmycins—natural siderophore-drug conjugates: prospects for modification and investigation based on successful total synthesis. Paper presented at the 2nd international Biometals symposium, Garmisch-Partenkirchen, Germany.

Vértesy, L., Aretz, W., Fehlhaber, H. W., and Kogler, H. (1995) Salmycin A-D, antibiotics from Streptomyces violaceus, DSM 8286, having a siderophore aminoglycoside structure, Helv. Chim. Acta 78, 46-60.

Wencewicz, T. A., Möllmann, U., Long, T. E., and Miller, M. J. (2009) Is drug release necessary for antimicrobial activity of siderophore-drug conjugates? Syntheses and biological studies of the naturally occurring salmycin "Trojan Horse" antibiotics and synthetic desferridanoxamine-antibiotic conjugates, Biometals 22, 633-648.

Wencewicz, T. A., Long, T. E., Möllmann, U., and Miller, M. J. (2013) Trihydroxamate siderophore-fluoroquinolone conjugates are selective sideromycin antibiotics that target Staphylococcus aureus, Bioconjugate Chem. 24, 473-486.

Roosenberg, J. M., and Miller, M. J. (2000) Total synthesis of the siderophore danoxamine, J. Org. Chem. 65, 4833-4838.

Hennard, C., Truong, Q. C., Desnottes, J. F., Paris, J. M., Moreau, N. J., and Abdallah, M. A. (2001) Synthesis and activities of pyoverdin-quinolone adducts: a prospective approach to a specific therapy against Pseudomonas aeruginosa, J. Med. Chem. 44, 2139-2151.

Rivault, F., Liebert, C., Burger, A., Hoegy, F., Abdallah, M. A., Schalk, I. J., and Mislin, G. L. (2007) Synthesis of pyochelin-norfloxacin conjugates, Bioorg. Med. Chem. Lett. 17, 640-644.

Noël, S., Gasser, V., Pesset, B., Hoegy, F., Rognan, D., Schalk, I. J., and Mislin, G. L. (2011) Synthesis and biological properties of conjugates between fluoroquinolones and a N3"-functionalized pyochelin, Org. Biomol. Chem. 9, 8288-8300.

Ji, C., and Miller, M. J. (2012) Chemical syntheses and in vitro antibacterial activity of two desferrioxamine B-ciprofloxacin conjugates with potential esterase and phosphatase triggered drug release linkers, Bioorg. Med. Chem. 20, 3828-3836.

Levine, M. N., and Raines, R. T. (2012) Trimethyl lock: a trigger for molecular release in chemistry, biology, and pharmacology, Chem. Sci. 3, 2412-2420.

Schröder, I., Johnson, E., and de Vries, S. (2003) Microbial ferric iron reductases, FEMS Microbiol. Rev. 27, 427-447.

Miethke, M., and Marahiel, M. A. (2007) Siderophore-based iron acquisition and pathogen control, Microbiol. Mol. Biol. Rev. 71, 413-451.

Müller, G., and Raymond, K. N. (1984) Specificity and mechanism of ferrioxamine-mediated iron transport in Streptomyces pilosus, J. Bacteriol. 160, 304-312.

Ghosh, A., Ghosh, M., Niu, C., Malouin, F., Möllmann, U., and Miller, M. J. (1996) Iron transport-mediated drug delivery using mixed-ligand siderophore-⁻-lactam conjugates, Chem. Biol. 3, 1011-1019.

Wencewicz, T. A., and Miller, M. J. (2013) Biscatecholate-monohydroxamate mixed ligand siderophore-carbacephalosporin conjugates are selective sideromycin antibiotics that target Acinetobacter baumannii, J. Med. Chem. 56, 4044-4052.

Diarra, M. S., Lavoie, M. C., Jacques, M., Darwish, I., Dolence, E. K., Dolence, J. A., Ghosh, A., Ghosh, M., Miller, M. J., and Malouin, F. (1996) Species selectivity of new siderophore-drug conjugates that use specific iron uptake for entry into bacteria, Antimicrob. Agents Chemother. 40, 2610-2617.

Mitscher, L. A. (2005) Bacterial topoIsomerase inhibitors: quinolone and pyridone antibacterial agents, Chem. Rev. 105, 559-592.

Ong, W., Yang, Y. M., Cruciano, A. C., and McCarley, R. L. (2008) Redox-triggered contents release from liposomes, J. Am. Chem. Soc. 130, 14739-14744.

Mendoza, M. F., Hollabaugh, N. M., Hettiarachchi, S. U., and McCarley, R. L. (2012) Human NAD(P)H:quinone xxidoreductase type I (hNQO1) zctivation of quinone propionic acid trigger groups, Biochemistry 51, 8014-8026.

Ji, C., Miller, P. A., and Miller, M. J. (2012) Iron transport-mediated drug delivery: practical syntheses and in vitro antibacterial studies of tris-catecholate siderophore-aminopenicillin conjugates reveals selectively potent antipseudomonal activity, J. Am. Chem. Soc. 134, 9898-9901.

Clinical and Laboratory Standards Institute (CLSI). (2009) Methods for dilution antimicrobial susceptibility tests for bacteria that grow aerobically, 8th ed., approved standard document M07-A7, Villanova, Pa., USA.

The invention claimed is:

1. A compound, comprising:
an Fe(III)-binding siderophore, or an Fe(III)-bound siderophore;
one or more optional linkers covalently bound to the siderophore;
a drug; and
an Fe(III) to Fe(II) reduction triggered linker having the following formula Q bound to the drug and the linker or, if no linker is present, then bound to the drug and the siderophore:

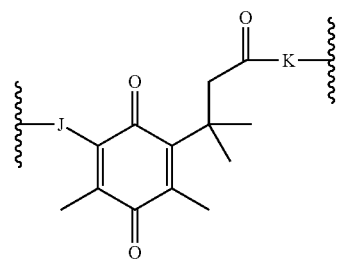

(Q)

wherein J is a covalent bond or group having the formula —(CO)NR'— or —NR'—, J being bound to the linker or, if no linker is present, then to the siderophore;
wherein K is a covalent bond, —O—, or —NR'—, K being bound to the drug; and
R' is independently H or alkyl;
or pharmaceutically acceptable salt or solvate thereof;
wherein the drug is an antibiotic selected from the group consisting of amikacin, aminoglycoside, amoxicillin, amphotericin, ampicillin, ansamycin, azithromycin, aztreonam, bacillomycin, BAL30072, beta-lactam, biapenem, carbacephalosporins, carbapenem, carbomycin, carbomycin A, carumonam, cefaclor, cefalotin, cephalosporin, cethromycin, chloramphenicol, chlortetracycline, clarithromycin, clindamycin, daptomycin, demeclocycline, dirithromycin, doripenem, doxorubicin, doxycycline, ertapeneme, erythromycin, ethambutol, fluoroquinolone, gentamicin, imipenem, isoniazid, josamycin, kanamycin, kitasamycin, lincomycin, linezolid, loracarbef, macrolide, meropenem, methacycline, midecamycin, monobactam, mupirocin, neomycin, nystatin, oleandomycin, oleandomycin, oxazolidinones, oxytetracycline, panipenem, penem, penicillin, peptide antibiotic, polymixin, pyrrolnitrin, quinolone, rifampin, rifamycins, rolitetracycline, roxithromycin, solithromycin, spiramycin, cstreptomycin, sulfabenzamide, sulfacetamide, sulfadiazine, sulfadoxine, sulfamerazine, sulfamethazine, sulfamethizole, sulfisoxazole, telithromycin, tetracycline, tigimonam, troleandomycin, tylosin, tylocine, vancomycin, zyvox, or combination thereof.

2. The compound of claim 1, wherein the siderophore comprises a natural siderophore, semi-synthetic siderophore, synthetic siderophore, or combination thereof.

3. The compound of claim 1, wherein the siderophore comprises one or more iron(III)-binding ligands.

4. The compound of claim 1, the siderophore comprises one or more iron(III)-binding catechols, hydroxamic acids, beta-hydroxy acids, heteroaromatic ligands, or combination thereof.

5. The compound of claim 1, having one of the following formulas:

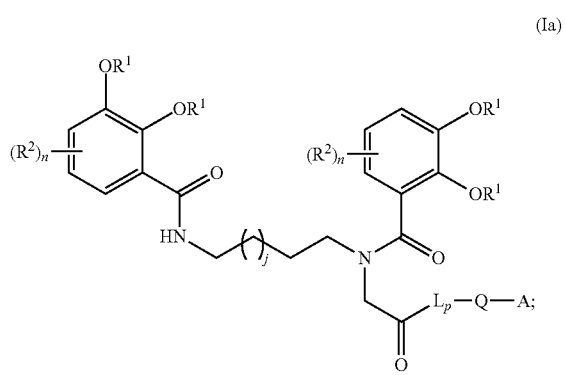

(Ia)

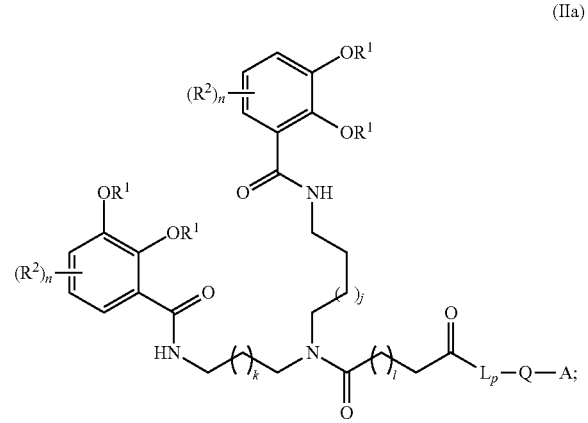

(IIa)

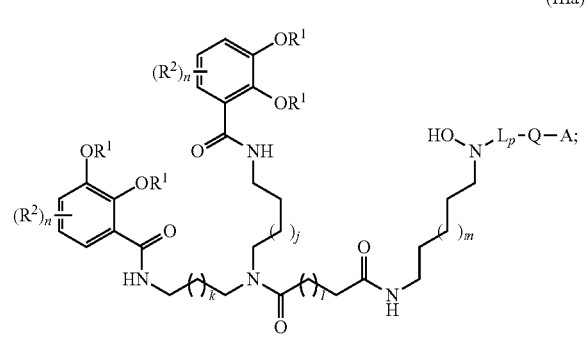

(IIIa)

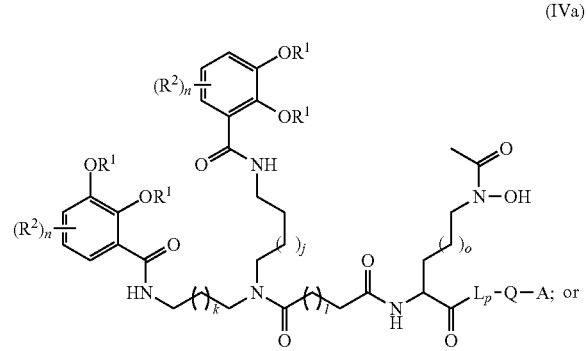

(IVa)

-continued

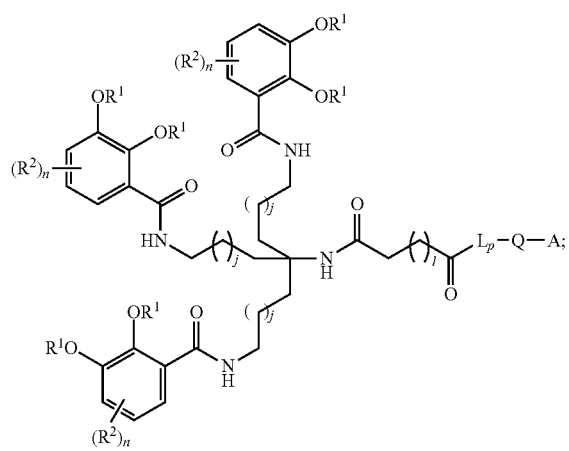
(Va)

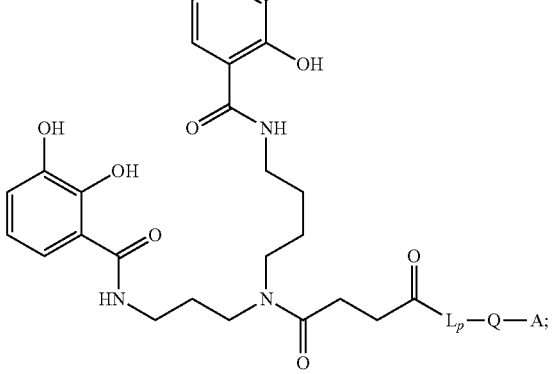
(IIb)

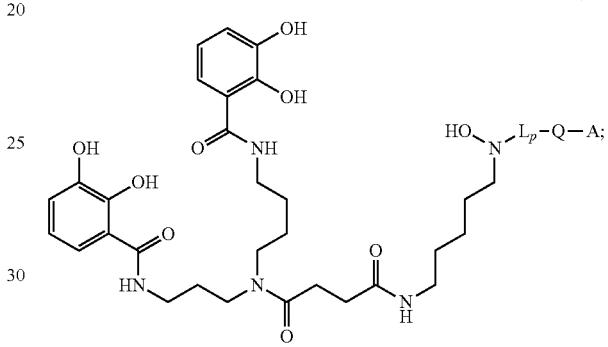
(IIIb)

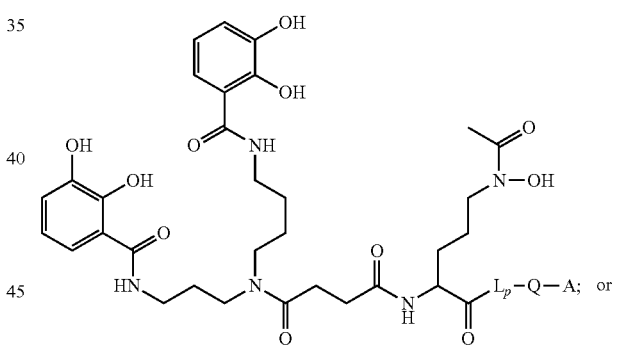
(IVb)

wherein

A is drug;

each L is independently a linker;

each $R^1$ is independently H, —C(=O)alkyl, —C(=O)aryl, or —C(=O)O-alkyl;

each $R^2$ is independently H, alkyl, alkoxy, hydroxy, carboxy, halo, nitro, amino, or cyano;

each n is independently 1, 2, or 3;

each p is independently 0-11;

each j is independently 0-11;

each k is independently 1-11;

each l is independently 1-11;

each o is independently 0-11; and each m is independently 0-11;

Fe(III)-bound form thereof, pharmaceutically acceptable salt thereof, solvate thereof, or combination thereof.

6. The compound of claim 1, wherein the compound has one of the following formulas:

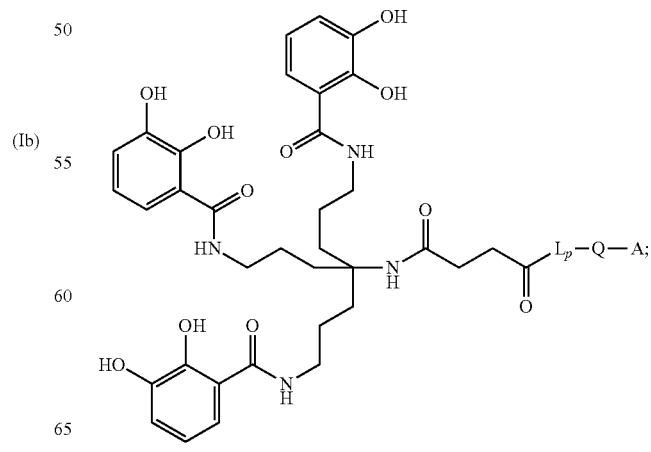
(Ib)

(Vb)

wherein

A is a drug;

each L is independently a linker; and each p is independently 0-11;

Fe(III)-bound form thereof, pharmaceutically acceptable salt thereof, solvate thereof, or combination thereof.

7. The compound of claim 1, wherein one or more than one linker is present.

8. The compound of claim 1, wherein more than one linker is present.

9. The compound of claim 1, wherein no linker is present.

10. A pharmaceutical composition, comprising the compound of claim 1, or mixture thereof, and a pharmaceutically acceptable diluent or carrier.

11. The pharmaceutical composition of claim 10, wherein the diluent or carrier comprises a pharmaceutically acceptable hydrogel.

12. A method for treating a bacterial infection in a subject suffering from said bacterial infection, comprising administering the compound of claim 1 to the subject.

13. A method for treating a bacterial infection in a subject suffering from said bacterial infection, comprising administering the composition of claim 10 to the subject.

14. The method of claim 12, wherein the bacterial infection is caused by an antibiotic-resistant bacterium, Gram-positive bacterium, or Gram-negative bacterium.

15. The method of claim 13, wherein the bacterial infection is caused by an antibiotic-resistant bacterium, Gram-positive bacterium, or Gram-negative bacterium.

16. A method for killing or inhibiting the growth of a bacterium, comprising contacting the bacterium with the compound of claim 1.

17. A method for killing or inhibiting the growth of a bacterium, comprising contacting the bacterium with the composition of claim 10.

* * * * *

UNITED STATES PATENT AND TRADEMARK OFFICE
CERTIFICATE OF CORRECTION

| | |
|---|---|
| PATENT NO. | : 11,014,891 B2 |
| APPLICATION NO. | : 15/031736 |
| DATED | : May 25, 2021 |
| INVENTOR(S) | : Marvin J. Miller et al. |

It is certified that error appears in the above-identified patent and that said Letters Patent is hereby corrected as shown below:

In the Specification

Column 1, Lines 14-16, delete:
"This research was supported in part by grant 2R01 AI054193 from the National Institutes of Health. The United States government has certain rights in this invention."
And insert therefor the following text:
-- This invention was made with government support under grant R01 AI054193 awarded by the National Institutes of Health. The government has certain rights in the invention. --

Column 9, Line 62, should be changed as follows:
"The alkylfurans (e.g., the compounds of formula (I')), the furan compounds (e.g., the compounds of formula (A)), the catalysts, the acids, the hydrogen, the amine and urea reagents and the solvents, as well as the reaction conditions to produce the compounds of formula (I') are each described in further detail below."
-- The alkylfurans (e.g., the compounds of formula (I')), the furan compounds (e.g., the compounds of formula (A)), the catalysts, the acids, the hydrogen, the amide and urea reagents and the solvents, as well as the reaction conditions to produce the compounds of formula (I') are each described in further detail below. --

Column 103, Line 31, should be changed as follows:
"This Example demonstrates the production of 2,5-dimethylfuran (DMF) from 5-(chloromethyl)furfural (CMF) using various catalysts, reagents and reaction temperatures. Reactions 1, 2, 7 and 8 below were performed according to the protocol set forth in Example 4 above. Reactions 3-6 were performed according to the protocol below. The catalysts, CMF loading, aromatic reagent and amount, amine/urea reagent and amount and temperature are set forth in Table 6 below."
-- This Example demonstrates the production of 2,5-dimethylfuran (DMF) from 5-(chloromethyl)furfural (CMF) using various catalysts, reagents and reaction temperatures. Reactions 1, 2, 7 and 8 below were performed according to the protocol set forth in Example 4 above. Reactions 3-6 were performed according to the protocol below. The catalysts, CMF loading, aromatic reagent and amount, amide/urea reagent and amount and temperature are set forth in Table 6 below. --

Signed and Sealed this
Eighteenth Day of April, 2023

Katherine Kelly Vidal
*Director of the United States Patent and Trademark Office*